(12) United States Patent
Brown et al.

(10) Patent No.: US 10,106,847 B1
(45) Date of Patent: Oct. 23, 2018

(54) ELECTROCHEMICAL DETECTION OF BACTERIAL AND/OR FUNGAL INFECTIONS

(71) Applicant: Clinical Micro Sensors, Inc., Carlsbad, CA (US)

(72) Inventors: Bradley Adam Brown, San Marcos, CA (US); Milena Iacobelli Martinez, Vista, CA (US); Lisa Lynn Freeman-Cook, Carlsbad, CA (US); John Jay Harvey, San Marcos, CA (US); Christine J. Shaw, San Diego, CA (US); Anna Maria Al-Khouri, San Diego, CA (US)

(73) Assignee: Clinical Micro Sensors, Inc., Carlsbad, CA (US)

( * ) Notice: Subject to any disclaimer, the term of this patent is extended or adjusted under 35 U.S.C. 154(b) by 0 days.

(21) Appl. No.: 15/828,074

(22) Filed: Nov. 30, 2017

Related U.S. Application Data

(63) Continuation of application No. 15/686,001, filed on Aug. 24, 2017.

(51) Int. Cl.
| | |
|---|---|
| *C12Q 1/68* | (2018.01) |
| *C12Q 1/686* | (2018.01) |
| *C12Q 1/6853* | (2018.01) |
| *B01L 3/00* | (2006.01) |

(52) U.S. Cl.
CPC ............ *C12Q 1/686* (2013.01); *B01L 3/5023* (2013.01); *B01L 3/5027* (2013.01); *C12Q 1/6853* (2013.01); *B01L 2300/0819* (2013.01); *C12Q 2600/16* (2013.01)

(58) Field of Classification Search
None
See application file for complete search history.

(56) References Cited

U.S. PATENT DOCUMENTS

| | | | |
|---|---|---|---|
| 4,887,455 A | 12/1989 | Payne et al. | |
| 5,173,418 A | 12/1992 | Molin et al. | |
| 5,591,578 A | 1/1997 | Meade et al. | |
| 5,705,348 A | 1/1998 | Meade et al. | |
| 5,770,365 A | 6/1998 | Lane et al. | |
| 5,770,369 A | 6/1998 | Meade et al. | |
| 5,807,701 A | 9/1998 | Payne et al. | |
| 5,824,473 A | 10/1998 | Meade et al. | |
| 5,882,497 A | 3/1999 | Persaud et al. | |
| 6,013,170 A | 1/2000 | Meade | |
| 6,013,459 A | 1/2000 | Meade | |
| 6,033,601 A | 3/2000 | Persaud et al. | |
| 6,063,573 A | 5/2000 | Kayyem | |
| 6,090,933 A | 7/2000 | Kayyem et al. | |
| 6,096,273 A | 8/2000 | Kayyem et al. | |
| 6,180,064 B1 | 1/2001 | Persaud et al. | |
| 6,190,858 B1 | 2/2001 | Persaud et al. | |
| 6,192,351 B1 | 2/2001 | Persaud | |
| 6,221,583 B1 | 4/2001 | Kayyem et al. | |
| 6,232,062 B1 | 5/2001 | Kayyem et al. | |
| 6,236,951 B1 | 5/2001 | Payne et al. | |
| 6,248,299 B1 | 6/2001 | Meade | |
| 6,264,825 B1 | 7/2001 | Blackburn et al. | |
| 6,265,155 B1 | 7/2001 | Meade et al. | |
| 6,290,839 B1 | 9/2001 | Kayyem et al. | |
| 6,361,958 B1 | 3/2002 | Shieh et al. | |
| 6,376,232 B1 | 4/2002 | Payne et al. | |
| 6,431,016 B1 | 8/2002 | Payne | |
| 6,432,723 B1 | 8/2002 | Plaxco et al. | |
| 6,479,240 B1 | 11/2002 | Kayyem et al. | |
| 6,495,323 B1 | 12/2002 | Kayyem et al. | |
| 6,518,024 B2 | 2/2003 | Choong et al. | |
| 6,541,617 B1 | 4/2003 | Bamdad et al. | |
| 6,596,483 B1 | 7/2003 | Choong et al. | |
| 6,600,026 B1 | 7/2003 | Yu | |
| 6,602,400 B1 | 8/2003 | Choong et al. | |
| 6,627,412 B1 | 9/2003 | Manning et al. | |
| 6,642,046 B1 | 11/2003 | McGarry et al. | |

(Continued)

FOREIGN PATENT DOCUMENTS

| | | |
|---|---|---|
| WO | WO 98/20162 A2 | 5/1998 |
| WO | WO 2001/006016 A2 | 2/2001 |

(Continued)

OTHER PUBLICATIONS

Gosiewski et al. (2014) BMC 14:144.*
Martic et al. (2011) Dalton Trans. 40: 7264-7290.*
Ribosolutions Inc Cyanase TM Inactivation cartridge product sheet 2014.*
Roux, Optimization and troubleshooting in PCR, Cold Spring Harb Protoc. Apr. 2009;2009(4):pdb.ip66.*
Liao et al., Use of Electrochemical DNA Biosensors for Rapid Molecular Identification of Uropathogens in Clinical Urine Specimens, J Clin Microbiol. Feb. 2006;44(2):561-70.*
"Benzonase Nuclease" *Merck Biosciences* brochure, pp. 1-16.
Babady and Kayyem, *AMP 2016 Workshop*, pp. 1-12.
Gosiewski et al. "A novel, nested, multiplex, real-time PCR for detection of bacteria and fungi in blood ," *BMC Microbiology* 14:144, pp. 1-7 (2014).

(Continued)

*Primary Examiner* — Aaron A Priest
(74) *Attorney, Agent, or Firm* — Klarquist Sparkman, LLP

(57) ABSTRACT

The present disclosure relates to methods and devices for amplifying a plurality of targets in a single PCR run while distinguishing between clinically relevant amplification and amplification from other sources such as from background contamination. The methods and devices further enable discrimination between gram-positive, gram-negative and fungal infections as wells as identify antimicrobial resistance genes. When applying the methods and devices of the invention, the species or genus of an infection(s), and genus of a fungal co-infection(s) or category of bacterial (gram-positive or negative) co-infection(s) are identified. Species identification of co-infections can also be achieved. Further, when applying the methods and devices of the invention, organisms which are likely to be contaminating organisms from a blood draw are identified.

20 Claims, 23 Drawing Sheets
(17 of 23 Drawing Sheet(s) Filed in Color)
Specification includes a Sequence Listing.

(56) References Cited

U.S. PATENT DOCUMENTS

| | | |
|---|---|---|
| 6,655,010 B1 | 12/2003 | Hatfield et al. |
| 6,686,150 B1 | 2/2004 | Blackburn et al. |
| 6,740,518 B1 | 5/2004 | Duong et al. |
| 6,753,143 B2 | 6/2004 | Tao et al. |
| 6,761,816 B1 | 7/2004 | Blackburn et al. |
| 6,824,669 B1 | 11/2004 | Li et al. |
| 6,833,267 B1 | 12/2004 | Kayyem |
| 6,875,619 B2 | 4/2005 | Blackburn |
| 6,942,771 B1 | 9/2005 | Kayyem |
| 6,951,759 B2 | 10/2005 | Travers et al. |
| 6,960,467 B2 | 11/2005 | Shieh et al. |
| 6,977,151 B2 | 12/2005 | Kayyem et al. |
| 7,014,992 B1 | 3/2006 | Kayyem et al. |
| 7,018,523 B2 | 3/2006 | Meade |
| 7,045,285 B1 | 5/2006 | Kayyem et al. |
| 7,056,669 B2 | 6/2006 | Kayyem et al. |
| 7,087,148 B1 | 8/2006 | Blackburn et al. |
| 7,090,804 B2 | 8/2006 | Kayyem et al. |
| 7,125,668 B2 | 10/2006 | Kayyem et al. |
| 7,160,678 B1 | 1/2007 | Kayyem et al. |
| 7,172,897 B2 | 2/2007 | Blackburn et al. |
| 7,267,939 B2 | 9/2007 | Meade |
| 7,312,087 B2 | 12/2007 | Duong et al. |
| 7,381,525 B1 | 6/2008 | Kayyem et al. |
| 7,381,533 B2 | 6/2008 | Kayyem et al. |
| 7,384,749 B2 | 6/2008 | Kayyem et al. |
| 7,393,645 B2 | 7/2008 | Kayyem et al. |
| 7,514,228 B2 | 4/2009 | Meade |
| 7,534,331 B2 | 5/2009 | Kayyem |
| 7,560,237 B2 | 7/2009 | O'Connor et al. |
| 7,566,534 B2 | 7/2009 | Meade |
| 7,579,145 B2 | 8/2009 | Meade |
| 7,582,419 B2 | 9/2009 | Meade |
| 7,595,153 B2 | 9/2009 | Meade |
| 7,601,507 B2 | 10/2009 | O'Connor et al. |
| 7,655,129 B2 | 2/2010 | Blackburn et al. |
| 7,713,711 B2 | 5/2010 | O'Connor et al. |
| 7,759,073 B2 | 7/2010 | O'Connor et al. |
| 7,820,391 B2 | 10/2010 | Chunlin |
| 7,863,035 B2 | 1/2011 | Clemens et al. |
| 7,935,481 B1 | 5/2011 | Umek et al. |
| 8,012,743 B2 | 9/2011 | Bamdad et al. |
| 8,114,661 B2 | 2/2012 | O'Connor et al. |
| 8,501,921 B2 | 8/2013 | Bamdad et al. |
| 9,222,623 B2 | 12/2015 | Wright et al. |
| 9,410,663 B2 | 8/2016 | Wright et al. |
| 9,453,613 B2 | 9/2016 | Wright et al. |
| 9,500,663 B2 | 11/2016 | Tieman et al. |
| 9,557,295 B2 | 1/2017 | Kayyem |
| 9,557,577 B2 | 1/2017 | Luc et al. |
| 9,598,722 B2 | 3/2017 | Wright et al. |
| 2003/0143556 A1 | 7/2003 | Blackburn et al. |
| 2008/0118923 A1 | 5/2008 | Park et al. |
| 2009/0061446 A1 | 3/2009 | Nimi et al. |
| 2009/0286691 A1 | 11/2009 | Kim et al. |
| 2011/0151453 A1 | 6/2011 | Bergeron et al. |
| 2011/0160074 A1 | 6/2011 | Wood et al. |
| 2014/0194305 A1 | 7/2014 | Kayyem et al. |
| 2014/0305811 A1 | 10/2014 | Kayyem et al. |
| 2014/0322706 A1 | 10/2014 | Kayyem et al. |
| 2014/0323326 A1 | 10/2014 | Kayyem et al. |
| 2014/0339318 A1 | 11/2014 | Shadpour et al. |
| 2015/0232916 A1* | 8/2015 | Rasmussen ............ C12Q 1/686 506/9 |
| 2015/0323555 A1 | 11/2015 | Kayyem et al. |
| 2016/0129437 A1 | 5/2016 | Kayyem et al. |
| 2017/0008275 A1 | 1/2017 | Liu et al. |

FOREIGN PATENT DOCUMENTS

| | | |
|---|---|---|
| WO | WO 2009/061941 A2 | 5/2009 |
| WO | WO 2016/012508 A1 | 1/2016 |

OTHER PUBLICATIONS

Higuchi et al. "Kinetic PCR analysis: Real-time Monitoring of DNA Amplification Reactions," *Bio/Technology* 11, pp. 1026-1030 (1993).

Horvath et al. "A novel, multiplex, real-time PCR-based approach for the detection of the commonly occurring pathogenic fungi and bacteria," *BMC Microbiology* 13:300, pp. 1-8 (2013).

Lukhtanov et al. "Rapid and efficient hybridization-triggered crosslinking within a DNA duplex by an oligodeoxyribonucleotide bearing a conjugated cyclopropapyrroloindole," *Nucleic Acids Research* 24:4, pp. 683-687 (1996).

Makary and Daniel "Medical error—the third leading cause of death in the US," *BMJ*, 353:i2139, pp. 1-5 (2016).

Tabone et al. "Factors Influencing the Extent and Regiospecificity of Cross-Link Formation between Single-Stranded DNA and Reactive Complementary Oligodeoxynucleotides," *Biochemistry* 33, pp. 375-383 (1994).

Yap, William T. "Mathematical analyses of ac voltammetry of a surface confined redox process," *Journal of Electroanalytical Chemistry* 454, pp. 33-38 (1998).

BioFire Advisory Notice, Risk of false positive *Pseudomonas aeruginosa* and *Enterococcus* results using FilmArray Blood Culture Identification Panel (Part No. RFIT-ASY-0109 and RFIT-ASY-0114) with bioMérieux BacT/ALERT SN Standard Anaerobic Blood Culture Bottles (Catalog No. 259790), 1 page (dated May 28, 2014).

RiboSolutions, Inc. "BENZONASE® Nuclease Alternative CYANASE™", "CYANASE™ Inactive System Superior Flexibility to BENZONASE® Nuclease, and CYANASE™ Inactivation Cartridges," http://www.ribosolutionsinc.com/cyanase1.html, 3 pages (downloaded from the web on Mar. 20, 2018).

\* cited by examiner

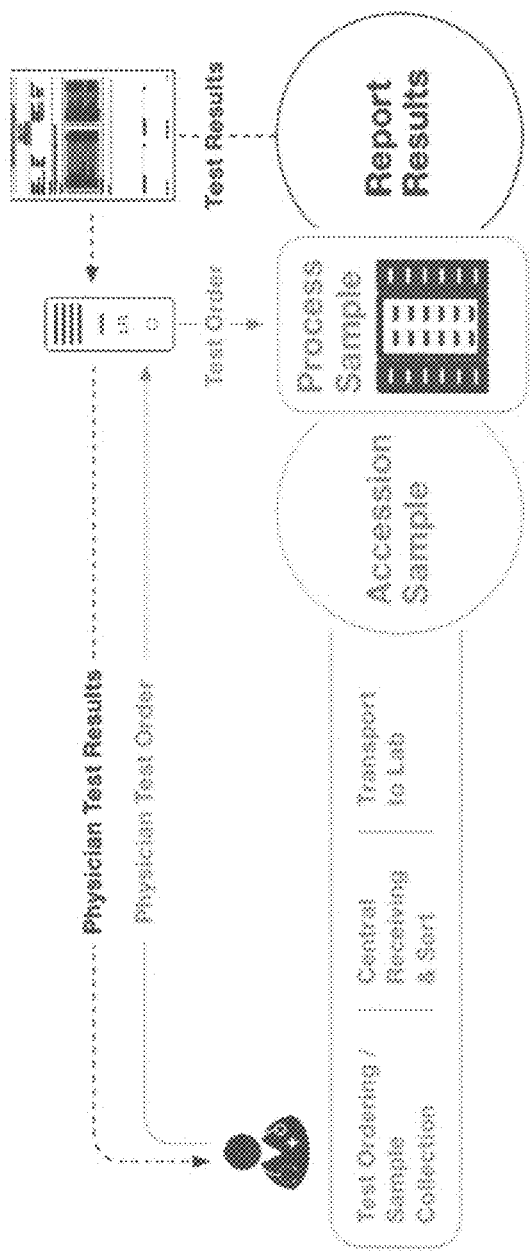
Fig. 2: Bi-directional LIS to automate and accelerate order entry and results reporting

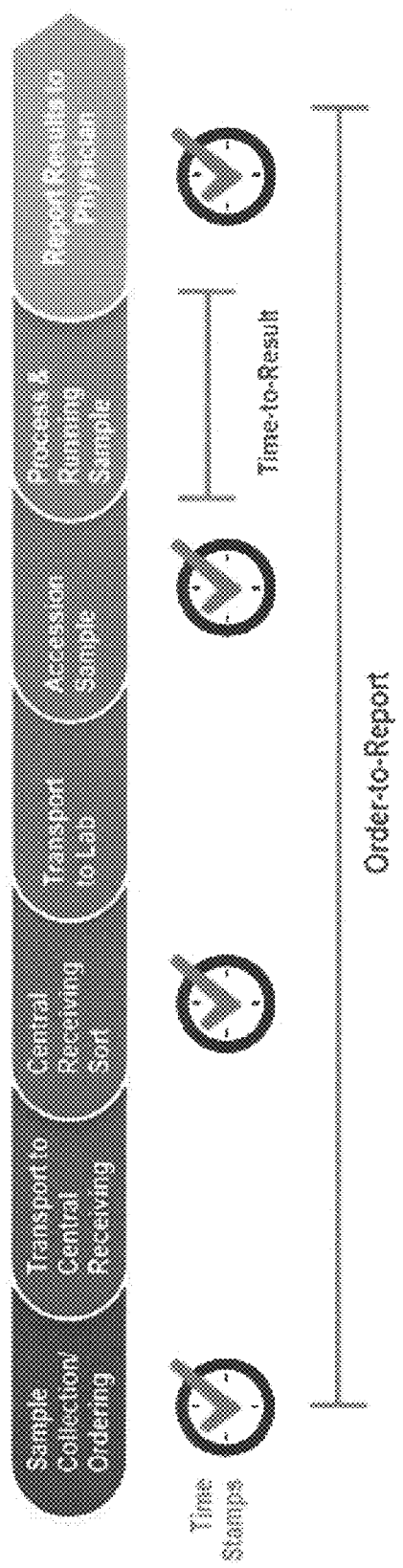
Fig. 3: Order-to-report Timeline

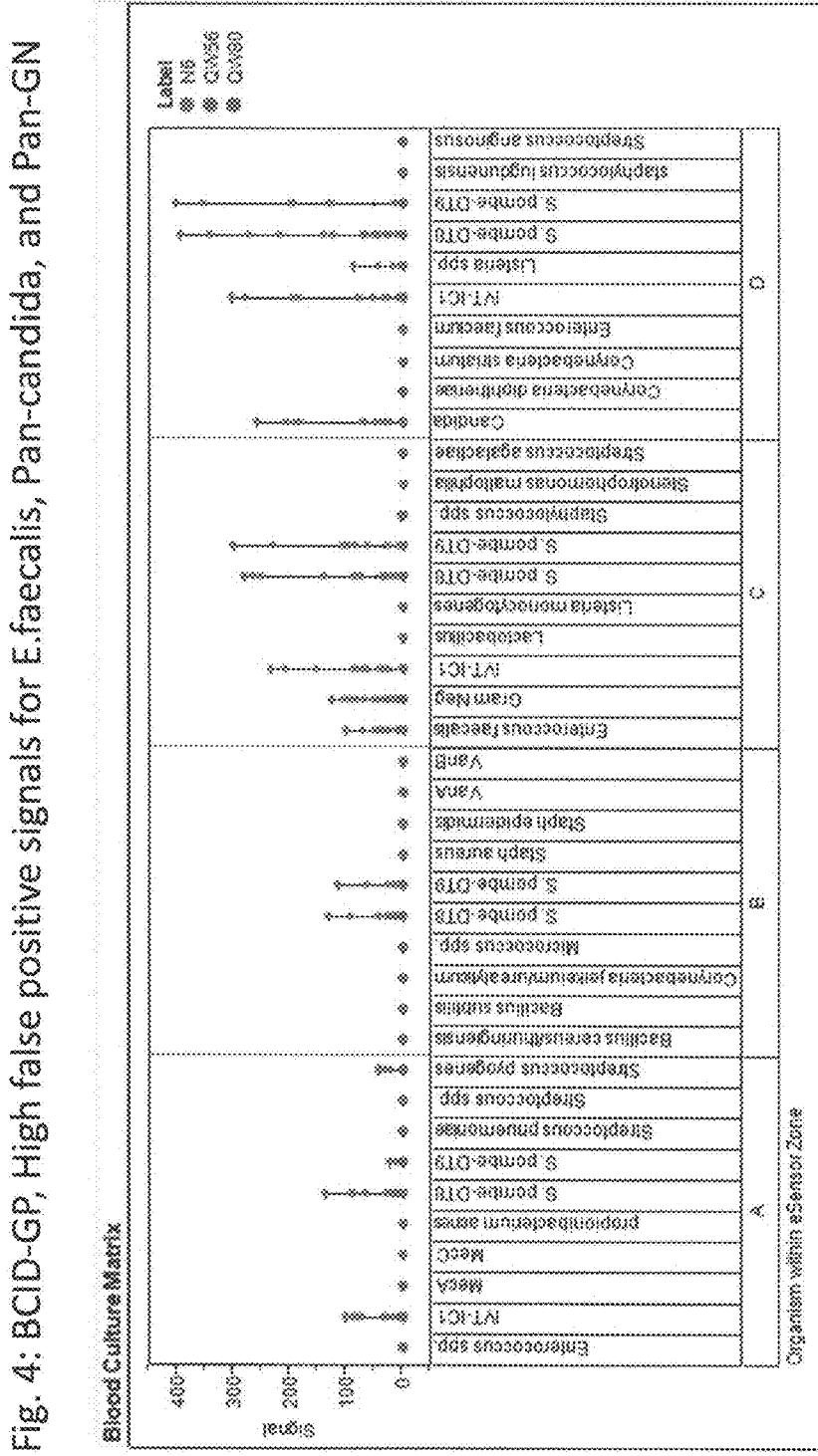

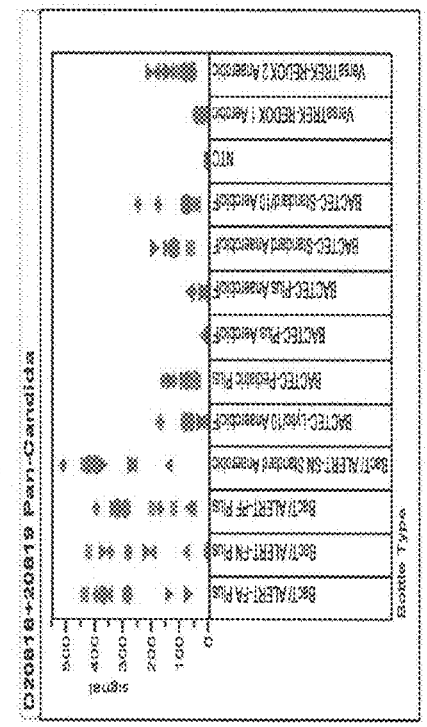
Fig. 5C
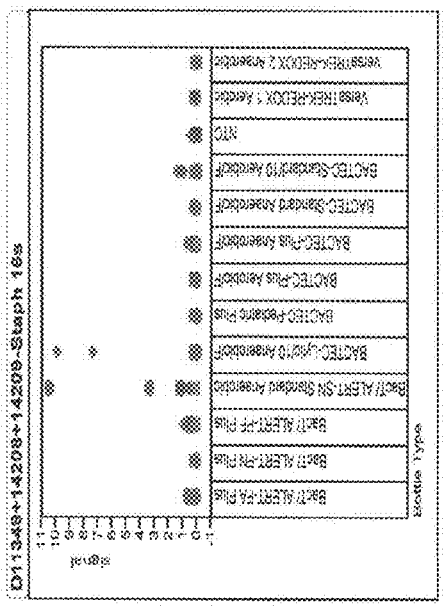
Fig. 5D
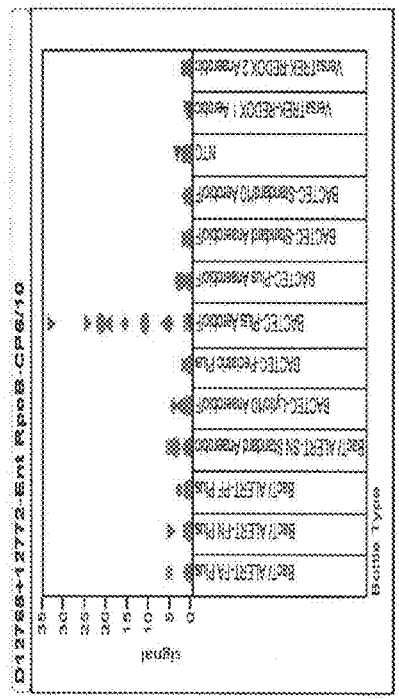
Fig. 5A
Fig. 5B

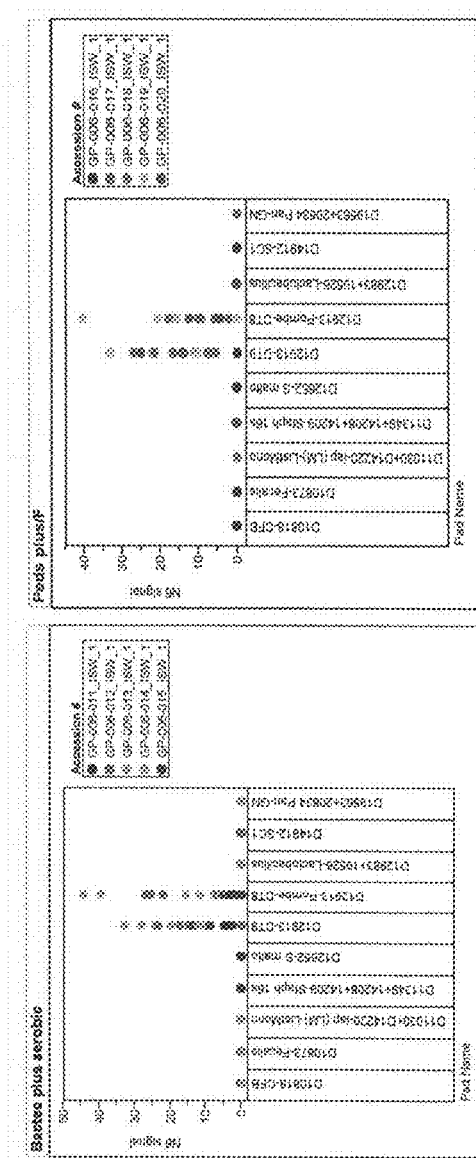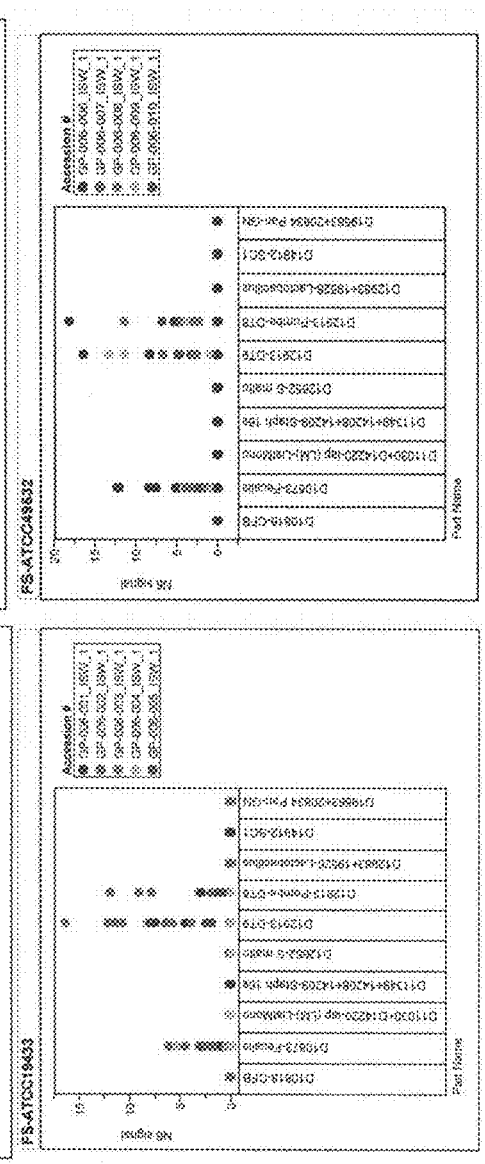
Fig. 7A  Fig. 7B  Fig. 7C  Fig. 7D

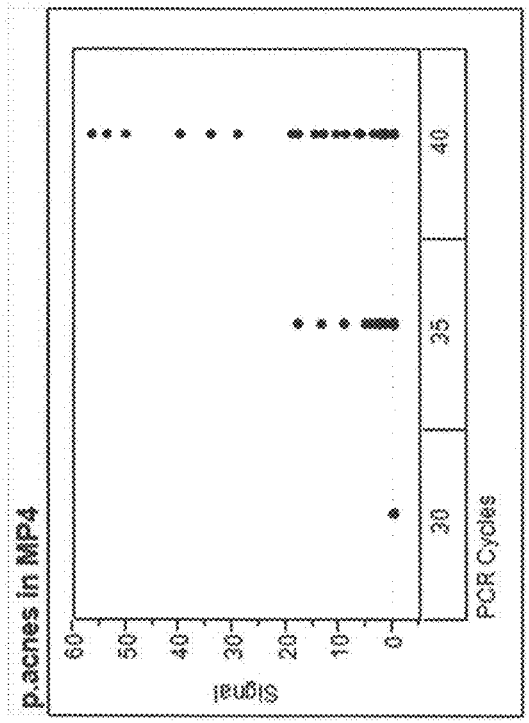
Fig. 8: BCID-GP, Background *P.acnes* signals with 30, 35, and 40-cycle PCR

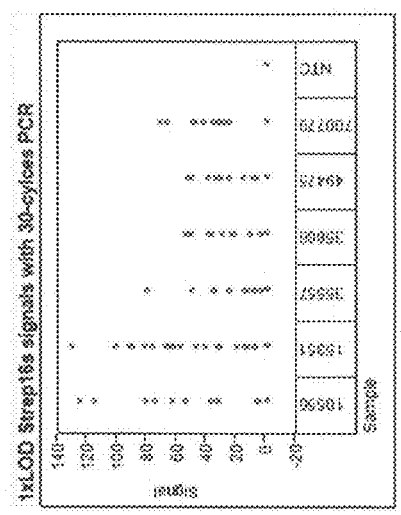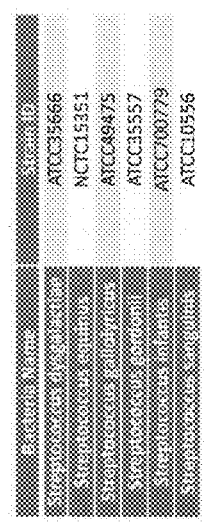
Fig. 10A
Fig. 10B
BCID-GP, *Strep spp.* assay performance with 30-cycle PCR.

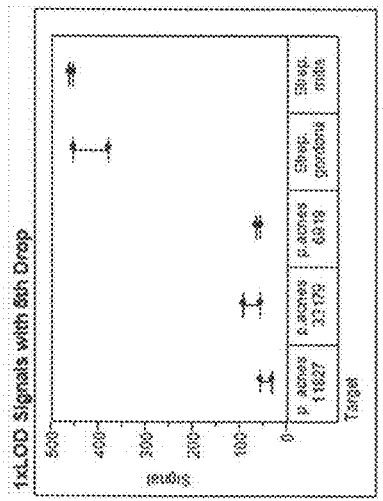
Fig. 11: BCID-GP cartridge with 1xLOD *Streptococcus spp.*

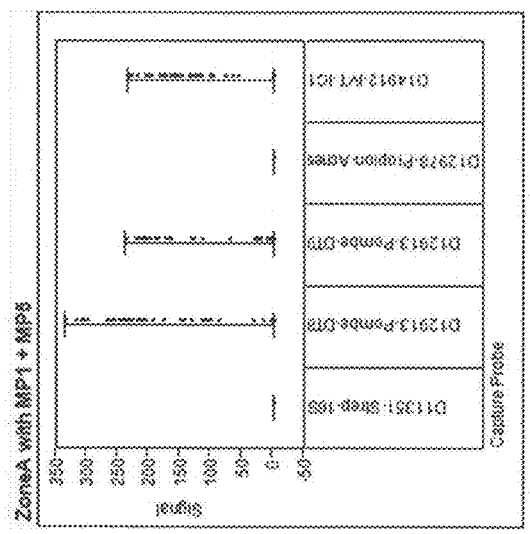
Fig. 12: Contamination of NTC sLRMs with *Streptococcus spp.* and *P. acnes* primers and 30 cycles of PCR

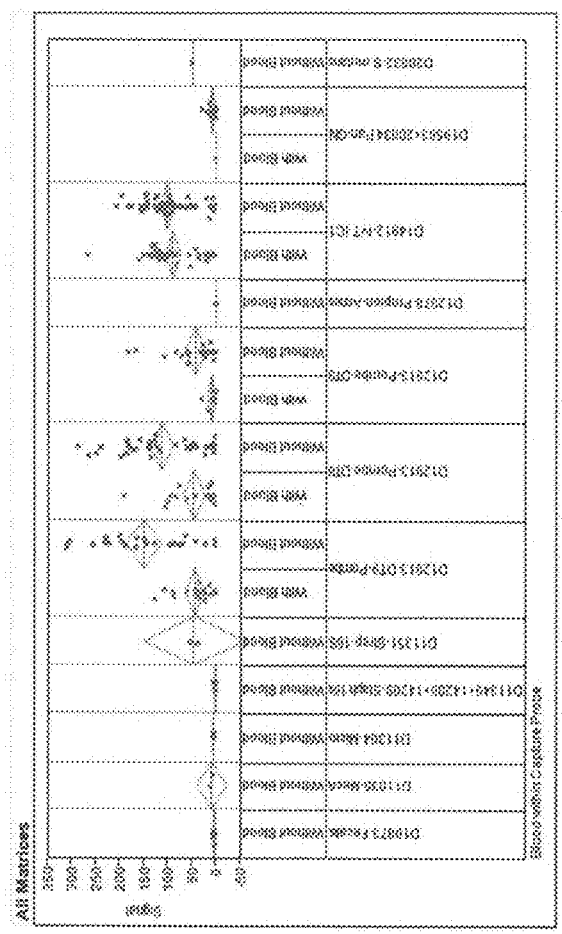
Fig. 13: BCID-GP, PCR cycles are reduced from 40 to 37

Fig. 14, BCID-GP Pool Layout

| Primer Pool | PCR cycles | Organisms and Drug Resistance |
|---|---|---|
| 1 | 30 | Streptococcus pyogenes |
| | | Mec C |
| | | Enterococcus spp. |
| | | S. Pombe |
| 2 | 30 | Van B |
| | | Micrococcus spp |
| | | Pan-candida |
| | | S. Pombe |
| 3 | 30 | Van A |
| | | Streptococcus agalactiae |
| | | Listeria monocytogenes |
| | | Stenotrophomonas maltophilia (part of Pan-GN) |
| | | Lactobacillus |
| 4 | 30 | S. Pombe |
| | | Staphylococcus lugdunensis |
| | | Streptococcus anginosus group |
| | | Enterococcus faecium |
| | | Listeria spp. |
| 5 | 30 | S. Pombe |
| | | Mec A |
| | | Streptococcus pneumoniae |
| | | propionibacterium |
| | | Streptococcus spp. |
| | | Synthetic Control 3 |
| 6 | 30 | Staphylococcus aureus |
| | | Bacillus Cereus |
| | | B. subtilis, licheniformis, amyloliquefaciens, atrophaeus |
| | | Staphylococcus epidermidis |
| | | Synthetic Control 1 |
| 7 | 35 | Pan-Gram Negative |
| | | Enterococcus faecalis |
| | | Synthetic Control 2 |
| 8 | 35 | Staphylococcus spp. |
| | | Corynebacterium spp. |
| | | Synthetic Control 1 |

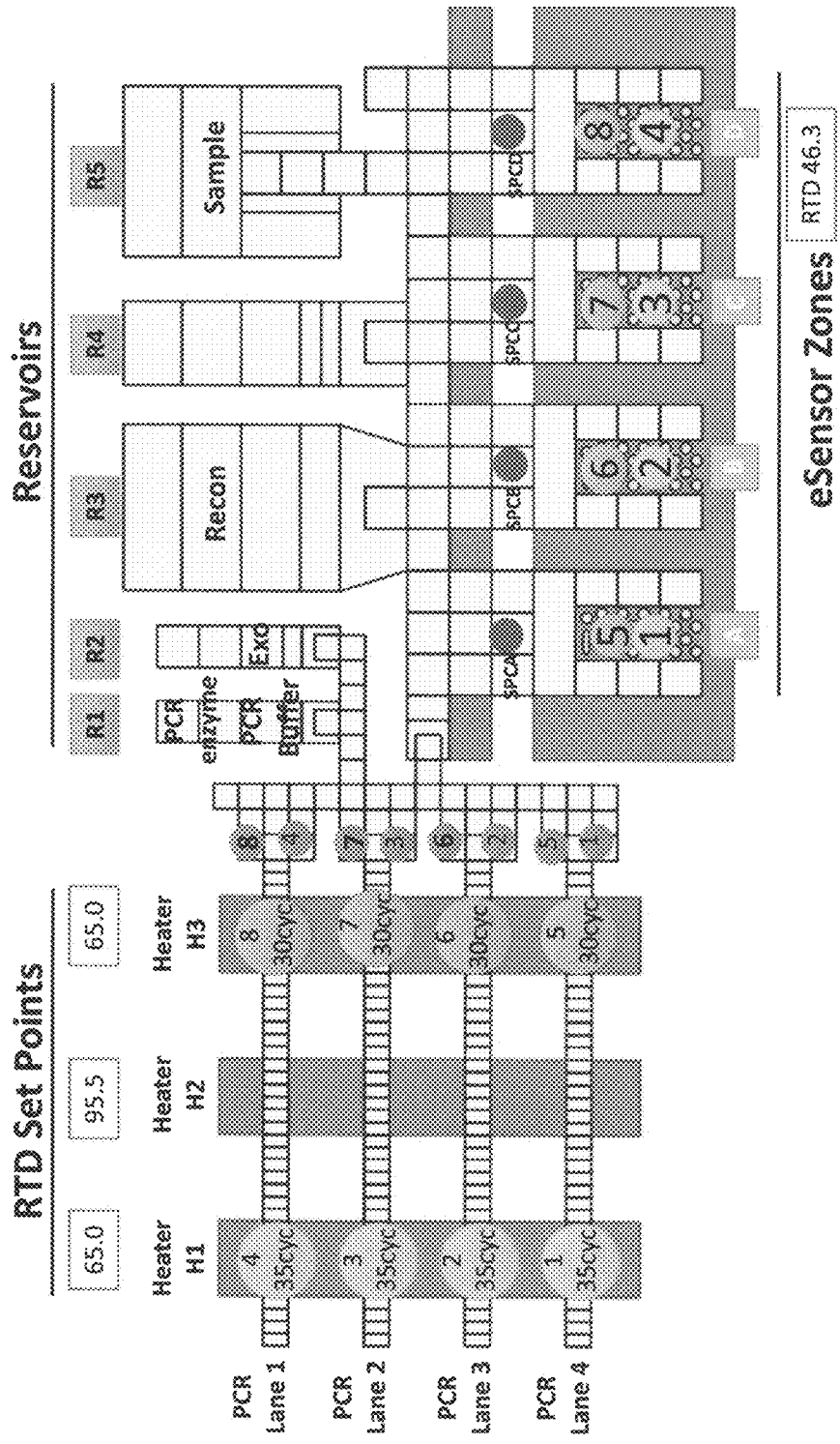
Fig. 15: PCB with GP Reagent & 8 PCR Drop Locations

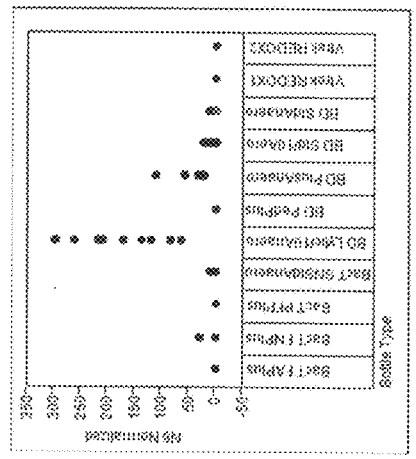
Fig. 16A, *Proteus mirabilis* false positive at 40 PCR cycles
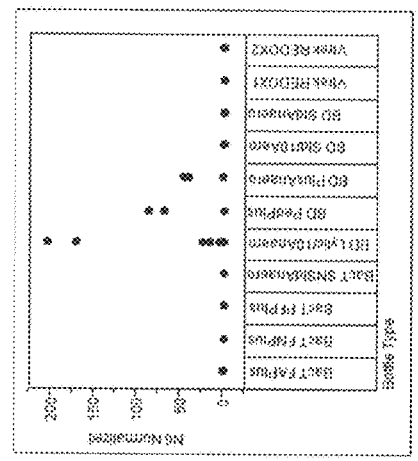
Fig. 16B, *Proteus spp* false positive at 40 PCR cycles

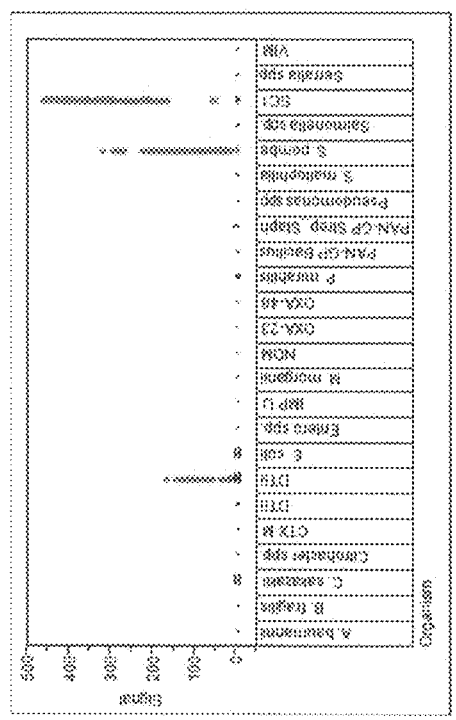
Fig. 17: BCID-GN, Negative bottles run with reduced cycling showed no false positives Fig. 18: BCID-GN Pool Layout (8 pools, 45 assays)

| | 1 | 2 | 3 | 4 |
|---|---|---|---|---|
| Control | S. pombe | S. pombe | S. pombe | S. pombe |
| Targets | Stenotrophomonas maltophilia | Enterobacter cloacae complex / Enterobacter asburiae | | KPC |
| | Cronobacter sakazakii | | Salmonella | NDM |
| | IMP universal | Pan Gram Positive | | |
| | Bacteroides fragilis | S. anginosus group | Serratia marcescens | VIM |
| | OXA (OXA-23) | Pan Candida / Candida albicans / Candida glabrata / Candida krusei / Candida porcpsilosis | Fusobacterium necrophorum | Enterobacter / Enterobacter aerogenes / Enterobacter ammigenus |
| 35 PCR cycles | CTX-M / CTX-1 / CTX-2 / CTX-8 / CTX-9 / CTX-25 | | | |

| | 5 | 6 | 7 | 8 |
|---|---|---|---|---|
| Control | SC1 | SC1 | SC1 | SC1 |
| Targets | OXA (OXA-48) | Escherichia coli | Pseudomonas aeruginosa | Klebsiella oxytoca |
| | Pan Gram Positive | Pan Gram Positive | Enterococcus faecalis | Proteus |
| | Staphylococcus | Enterococcus | | |
| | Streptococcus | Proteus mirabilis | Neisseria meningitides | Fusobacterium nucleatum |
| | Bacillus subtilis group | Acinetobacter baumannii | Morganella morganii | Enterobacter cloacae complex |
| | Bacillus cereus group | Serratia | Klebsiella pneumoniae | Enterobacter cloacae/hormaechei |
| 30 PCR cycles | | Citrobacter | Haemophilus influenzae | |

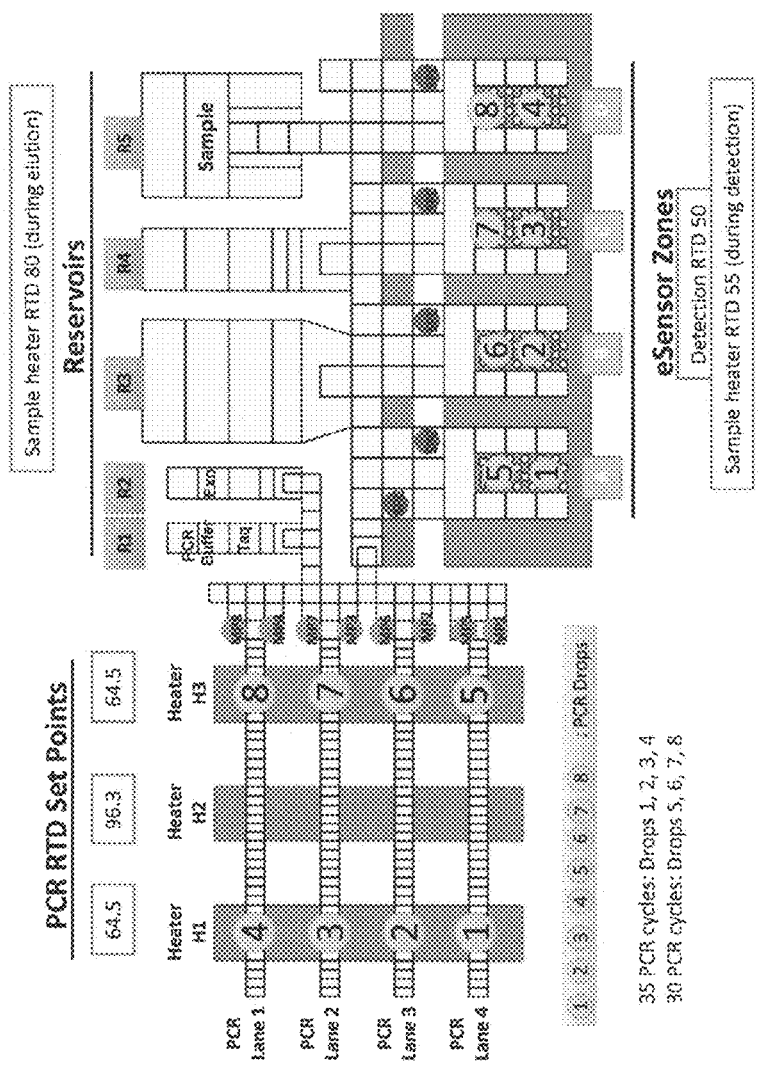
Fig. 19: BCID-GN Cartridge Layout

Fig. 21, BCID-FP Pool Layout
(4 pools, 17 assays)

| Cycles | Multiplex | Genus | Species | Gene |
|---|---|---|---|---|
| | ALL POOLS | DT-8 | N/A | |
| | | DT-9 | N/A | |
| | | Schizosaccharomyces pombe | | |
| 40 Cycles | 1 | Candida | dubliniensis | HWP1 |
| | | | fermata | TEF-1a |
| | | | kefyr | ACT1; EIF2 |
| | | | guilliermondii | FKS1 |
| | | | parapsilosis | FKS1; SADH |
| | | | tropicalis | RPB1 |
| | | Candida | glabrata | RPB1 |
| | | | tropicalis | RPB1 |
| | | | gattii | RNApol |
| | | Cryptococcus | neoformans var neoformans | |
| | | | neoformans var grubii | RNApol |
| | 2 | | solani ser | TEF-1a |
| | | | dimerum | TEF-1a |
| | | | proliferatum | TEF-1a |
| | | Fusarium (spp.) | moniliforme | TEF-1a |
| | | | verticillioides | TEF-1a |
| | | | oxysporum | TEF-1a |
| | | | sacchari | TEF-1a |
| | | | krusei | CS1 |
| | | Candida | lusitaniae | FKS1 |
| | | | parapsilosis | FKS1; SADH |
| | 3 | Rhodotorula (spp.) | mucilaginosa | cytB |
| | | | glutinis | |
| | | | asahii | |
| | | Trichosporon (spp.) | asteroides | cytB |
| | | | coremiiforme | |
| | | | dermatis | |
| | 4 | Malassezia | furfur | MF1 |
| | | Candida | albicans | RPOB1 |
| | | Candida | auris | GABA |

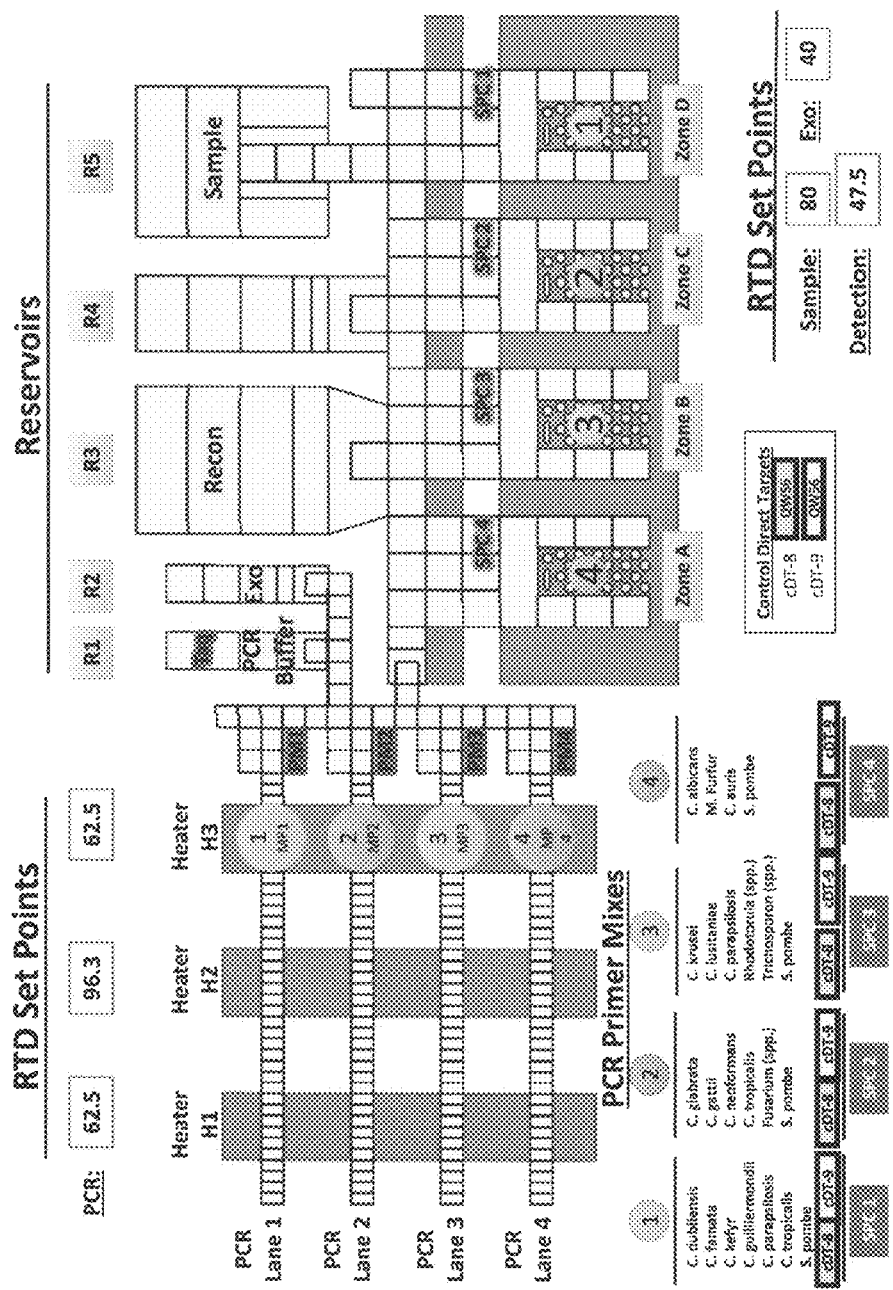

Fig. 23

ELECTROCHEMICAL DETECTION OF BACTERIAL AND/OR FUNGAL INFECTIONS

CROSS-REFERENCE TO RELATED APPLICATIONS

This application is a Continuation of U.S. patent application Ser. No. 15/686,001, filed Aug. 24, 2017, and is related to U.S. Pat. Nos. 7,820,391, 7,560,237, 6,013,459, 6,740,518, 6,063,573, 6,600,026, 6,264,825, 6,541,617, 6,942,771, 6,432,723, 6,833,267, 7,090,804, 7,935,481, 7,172,897, 6,753,143, 6,518,024, 6,642,046, 6,361,958, 6,602,400, 6,824,669, 6,596,483, 6,875,619, 7,863,035, 9,598,722 and U.S. patent application Ser. Nos. 12/914,257, 14/206,871, 14/206,932, 15/026,314, 14/538,533, 14/206,817, 14/538,602, 14/206,867, 14/206,903, 14/062,860, and 14/538,506, the respective disclosures of which are hereby incorporated by reference.

The invention relates to the field of molecular diagnostic methods, in particular, microfluidic devices for the detection of target analytes.

BACKGROUND OF THE INVENTION

In North America, the most common causes of a sepsis are bacteria such as *Escherichia coli* or *Staphylococcus aureus*. In addition to bacterial infection, fungal infections have in recent times become a significant cause of the disease. Fungal infections tend to be associated with higher rates of death. Only approximately 5% of fungal caused cases of sepsis are identified during the disease due to the poor diagnostic methods available. Recent studies have shown that patients with severe sepsis or septic shock showed an increased likelihood of death of 7.6% for every hour in which antibiotic therapy is not applied. Survival rates are also significantly reduced when antibiotics are not applied within the first 6 hours of identifying hypotension. Survival rates will be significantly increased if diagnosis times are reduced.

Culturing microorganisms from blood samples (Gram staining) remains the gold standard in detection of the microbiological cause of sepsis. This method is however subject to significant disadvantages, in particular, due to the large time difference between taking a blood sample and providing the results. It is not uncommon that 24 to 72 hours pass between taken a sample and providing diagnostic information. Within this time, broad band, untargeted antibiotic therapies are often introduced. This may lead to some success in treating the disease but is related to significant disadvantages with respect to the development of antibiotic resistant microorganisms.

Microarray and multiplex PCR approaches have been disclosed in the art, which are typically defined by extremely large numbers of probes or primers required for application of such methods (leading to significant cost and effort), a limited pool of target pathogens capable of being detected (such as only a limited sub-group of bacterial pathogens, or the absence of fungal pathogens), or a lack of discrimination between gram-negative and gram-positive bacterial pathogens, which provides sub-standard information for appropriate antibiotic therapies (US 2009286691 and US 2011151453). Methods for discriminating gram-positive and gram-negative bacteria have been disclosed in the art (US 20080118923 A1), in addition to the combined analysis of 16S and 18S sequences of bacteria and fungi (US 20090061446). Such methods, although potentially useful in clinical diagnostics, have never been applied in sepsis analytics and employ large numbers of primers in either microarray or very complex multiplex reactions, representing a significant technical and financial challenge for clinical diagnostic laboratories.

Multiplex RT-PCR approaches have been described in which a number of commonly occurring human pathogens are potentially detected. One example of such a multiplex PCR method is described in Gosiewski et al (BMC Microbiology 2014, 14:144) and U.S. Publication No. 2015/0232916, which discloses a nested PCR approach for detecting gram-positive and gram-negative bacteria, yeast, fungi and filamentous fungi from blood samples. A nested polymerase chain reaction involves two sets of primers, used in two successive runs of polymerase chain reaction, the second set intended to amplify a secondary target within the first run product. Nested PCR is applied in order to reduce nonspecific binding in products due to the amplification of unexpected primer binding sites, as it is unlikely that any of the unwanted PCR products contain binding sites for both the new primers in the second PCR run, ensuring the product from the second PCR has little contamination from unwanted products of primer dimers, hairpins, and alternative primer target sequences. Despite potentially reducing background signal, the PCR method described in Gosiewski and U.S. Publication No. 2015/0232916 are relatively complex and require two cycling reactions, essentially doubling the time, effort and reagents required for the analysis.

Other methods have employed the amplification of a number of PCR products from bacterial and fungal pathogens using sequence-specific oligonucleotides together with sequence-unspecific dyes, and subsequently, a melting curve analysis to differentiate between the various products (Horvath et al, BMC Microbiology 2013, 13:300). The method disclosed therein is however limited by a number of disadvantages known to occur with melting curve analyses.

Other methods have employed the amplification of a number of PCR products from bacterial and fungal pathogens using non-sequence-specific oligonucleotides together with sequence-specific probes to differentiate between the various products as described in EP 3172337. In such cases, only a broadband antibiotic therapeutic approach is possible, which may, in fact, be poorly suited for the particular pathogen.

Electrochemical detection techniques have higher detection sensitivity than conventional luminescence techniques (e.g., fluorescence and phosphorescence) due to higher signal-to-noise ratios. Because of their sensitivity and ability to accurately measures low-concentrations of nucleic acids, electrochemical detection techniques are able to differentiate between pathogenic species representing a significant technological improvement over the prior art. But, because of their sensitivity, false positive detection rates are high. Indeed, where organisms are cultured, the growth media often contains non-viable organisms or DNA/nucleic acids, which would not affect culture, but could produce false positives in PCR. If a system is designed uniformly for increased sensitivity to detect low titers pathogens, frequent false positive results may occur from background organisms or DNA/nucleic acids. Alternatively, if system sensitivity is reduced to avoid background organism detection, low titer organisms may be missed, resulting in false negative detection.

Further, when blood or other bodily fluids are obtained from a subject they may be contaminated by skin cells, bacteria, fungi, viruses, phages, their respective nucleic acids (including RNA and DNA) and/or other undesirable molecules, or disinfectants. Antiseptics are crucial for the practice of medicine; however, currently used antiseptics have a significant failure rate which results in substantial additional medical costs. Antiseptics are commonly used prior to routine phlebotomy, in preparation for minor and major invasive procedures, and as part of routine infection control hand-washing practices. The failure of antiseptics often result in erroneous diagnostic tests. For example, it has been estimated that a single false positive blood culture (i.e., where the culture indicates that the blood has been infected with bacteria, although the blood was contaminated during the blood draw) done on blood drawn from a patient at a hospital costs the patient an additional $2000 to $4,200 in unnecessary medication, additional follow up testing, and increased length of stay. (Bates, 1991).

Thus, there is a need in the art to provide methods which can selectively detect pathogenic organisms of interest. In particular, there is a need in the art for a method which enables the discrimination between a systemic infection and a false positive signal due to blood matrix bottle contamination. There is also a need in the art to identify when a blood culture is contaminated during blood draw.

BRIEF SUMMARY OF THE INVENTION

The ability to detect infection is hampered by background contamination present in blood culture bottles, such as are used in gram staining, a common first step in any clinical pathogen diagnosis. The invention disclosed herein can not only differentiate between background contamination (from any blood culture matrix bottle) and clinically relevant infection but can also differentiate between gram-positive bacterial infection, gram-negative bacterial infection, fungal infection and can identify antibiotic resistance genes. Even more importantly, the invention can identify the contaminating pathogen and contaminating co-infection (if present) by its species. Because prior art methods failed to recognize background contamination as an issue or cannot discriminate by species the infecting pathogen and co-infecting pathogen, the invention allows for better antimicrobial stewardship and improved patient care outcomes.

Disclosed herein are in vitro methods (or systems or devices) for the detection and/or identification of a human pathogen and/or genetic material thereof comprising subjecting a sample suspected of comprising a human pathogen and/or genetic material thereof to a single multiplex polymerase chain reaction (PCR), wherein said method (or system) comprises amplification of PCR products that enable discrimination between contaminating pathogen and/or genetic material present in the sample and infectious pathogen and/or genetic material present in the sample. In particular, the inventive method allows for a single amplification step and single detection step for the detection of an actual pathogenic infection and not a putative contamination. The inventive method does not require a purification step prior to amplification or detection. The inventive method does not require determining whether amplification has occurred prior to detection. When purification is needed or a determination as to whether amplification has occurred prior to detection requires human action and such systems cannot be fully automated like the invention disclosure herein. The inventive method does not require dilution of the PCR sample. The inventive method does not require additional testing or analysis to differentiate signaling due to contamination versus real pathogenic infections.

The methods (or system or devices) can further discriminate between gram-positive bacterial, gram-negative bacterial and fungal pathogens if present in said sample as well as identify antimicrobial resistance genes. An infection can be identified by its species, and a fungal co-infection can be identified by its genus whereas a bacterial co-infection of a different type than the infection (i.e. infection is GP and co infection is GN or vice versa) can be identified by its category (gram-positive or negative). If the infection and co-infection are of the same type (i.e., both gram-positive or both gram-negative), the systems and methods can identify the species of the co-infection via a single PCR run. If the infection and co-infection are of different types (i.e., the infection is gram-positive and the co-infection is gram-negative or fungal) the systems and methods can identify the species of the co-infection via a second single PCR run.

The methods (or system or devices) can further discriminate between background contamination and de-escalation targets. Background contamination from blood culture bottles is not detected by the methods (or system or devices) but organisms associated with possible contamination by blood draw such as *Propionibacterium acnes, Staphylococcus epidermidis, Micrococcus, Lactobacillus* or *Corynebacterium* (so called de-escalation targets) are identified. The methods (or system or devices) can further discriminate between (1) background contamination, (2) de-escalation targets and (3) clinically relevant gram-positive bacterial, gram-negative bacterial or fungal pathogens if present in the sample as well as identify antimicrobial resistance genes.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 2: Shows a schematic of the bi-directional LIS reporting.

FIG. 3: Shows a schematic of "Order-to-report." The clock time stamps are commonly documented in hospital and laboratory information systems.

FIG. 4: BCID-GP, High false positive signals for *Enterococcus faecalis*, Pan-*candida*, and Pan-GN in bottle matrix with no blood or bacterial targets.

FIG. 5A, FIG. 5B, FIG. 5C and FIG. 5D: False positives detected for *Enterococcus faecalis* (5A), Staph 16s (5B); *Enterococcus* (genus) (5C); and Pan-*Candida* (5D), were detected when negative blood culture matrices (no blood or bacterial targets) were tested on a BCID-GP cartridge.

FIG. 6A shows *Enterococcus faecalis* contamination signals are reduced but not eliminated with 35 cycles and FIG. 6B shows that at 35 cycles the *S. pombe* internal control is still detected.

FIG. 7A, FIG. 7B, FIG. 7C and FIG. 7D: False positive signal from blood culture bottles is eliminated using a 30-cycle PCR. FIGS. 7A and 7B show that only the positive controls were detected. FIGS. 7C and 7D show that detection is possible (although weak) at 1×LOD (1×105 CFU/mL) *Enterococcus faecalis* run on sLRMs using a 30-cycle PCR.

FIG. 8: False Positives are detected with 40 and 35 cycles when BDIC-GP cartridges are spotted with *P. acnes* primers but eliminated with 30 cycle PCR

FIG. 10A and FIG. 10B: FIG. 10A shows that When 30 PCR cycles are used, six representative *Streptococcus* species identified by their identification number are detected at 1×LOD (1×106 CFU/mL). FIG. 10B corrolates the bacterial species name and identification number.

FIG. 11: When primer concentration is increased, three *P. acnes* strains and two *Streptococcus* species are detected at 30 PCR cycles and 1×LOD (1×106 CFU/mL).

FIG. 12: No *Streptococcus* spp or *P. acnes* signals were detected with increased primer concentrations and 30 PCR cycles in negative blood culture matrices.

FIG. 13: When PCR cycles are reduced from 40 to 37, most blood matrix contamination is eliminated.

FIG. 14: BCID-GP Multiplex primer pool and PCR cycles.

FIG. 15: A schematic of the BCID-GP cartridge sub-assembly layout. Reservoirs, R1, R2, R3, R4, and R5 are part of the top plate. R1 typically includes PCR enzyme (Taq) and buffer; R2 typically includes exonuclease; R3 typically includes reconstitution buffer used to wet reagents and rehydrate PCR reagents; R4 typically includes is a waste manipulation zone or is empty for drop manipulation; and R5 is typically where the sample comes out of the LRM after extraction. "Sample" designates where the sample is loaded from the LRM. "PCR enzyme" means Taq and "PCR buffer" is a buffer; the buffer and PCR enzyme are shown where they are spotted on the top plate. "Exo" is exonuclease and is shown where it is spotted on the top plate. 1, 2, 3, 4, 5, 6, 7, 8 displayed vertically next to heater 3 are the multiplex primer pools; once the drop has the primers they go into PCR lane 1, 2, 3 or 4 as shown and cycled (35 or 30) as shown. 1, 2, 3, 4, 5, 6, 7, 8 displayed vertically on Heater 1 or 3 depict where each PCR drop is moved. SPCA means signal probe cocktail which is where the amplicon is mixed with the signal probe. Detection zones A, B, C and D are where detection takes place. The drops 1, 2, 3, 4, 5, 6, 7, 8 are moved into the detection zone as shown. The gold plated electrode is depicted as small round circles in the detection zone. The RTD temperature set points are shown in degrees Celsius.

FIG. 16A and FIG. 16B: Shows false positive signal for *Proteus mirabilis* (FIG. 16A) and *Proteus* (FIG. 16B) in negative blood culture matrices cycled 40 times (a variety of blood culture bottles are shown).

FIG. 17: when negative blood culture matrices were cycled 35 or 30 times (cycling as indicated in FIG. 17) no false positives were detected.

FIG. 18: BCID-GN Multiplex primer pool and PCR cycles. The bolded organisms are the genus calls in the detection report and the non-bolded organisms are species calls on the detection report.

FIG. 19: A schematic of the BCID-GN cartridge sub-assembly layout. Reservoirs, R1, R2, R3, R4, and R5 are part of the top plate. R1 typically includes PCR enzyme (Taq) and buffer; R2 typically includes exonuclease; R3 typically includes reconstitution buffer used to wet reagents and rehydrate PCR reagents; R4 typically includes is a waste manipulation zone or is empty for drop manipulation; and R5 is typically where the sample comes out of the LRM after extraction. "Sample" designates where the sample is loaded from the LRM. "PCR buffer" is a buffer; the buffer and taq are shown where they are spotted on the top plate. "Exo" is exonuclease and is shown where it is spotted on the top plate. MP1, MP2, MP3, MP4, MP5, MP6, MP7, MP8 displayed vertically next to heater 3 are the multiplex primer pools; 1, 2, 3, 4, 5, 6, 7, 8 displayed vertically on Heater 1 or 3 depict where each PCR drop is moved. Once the drop has the primers they go into PCR lane 1, 2, 3 or 4 and cycled (35 or 30) as shown in the key below. SPC means signal probe cocktail which is where the amplicon is mixed with the signal probe. Detection zones A, B, C and D is where detection takes place. The drops 1, 2, 3, 4, 5, 6, 7, 8 are moved into the detection zone as shown. The gold plated electrode is depicted as small round circles in the detection zone. The RTD temperature set points are shown in degrees Celsius.

FIG. 21: The BCID-FP Multiplex primer pool and PCR cycles.

FIG. 22: A schematic of the BCID-FP cartridge sub-assembly layout. Reservoirs, R1, R2, R3, R4, and R5 are part of the top plate. R1 typically includes PCR enzyme (Taq) and buffer; R2 typically includes exonuclease; R3 typically includes reconstitution buffer used to wet reagents and rehydrate PCR reagents; R4 typically includes is a waste manipulation zone or is empty for drop manipulation; and R5 is typically where the sample comes out of the LRM after extraction. "Sample" designates where the sample is loaded from the LRM. "PCR buffer" is a buffer; the buffer and taq are shown where they are spotted on the top plate. "Exo" is exonuclease and is shown where it is spotted on the top plate. PM1, PM2, PM3 and PM4 displayed vertically next to heater 3 are the multiplex primer pools 1-4; MP1, MP2, MP3 and MP4 means PCR primer mixes; 1, 2, 3, 4 displayed vertically on Heater 3 depict where each PCR drop is moved. Once the drop has the primers they go into PCR lane 1, 2, 3 or 4 and cycled 40 times. SPC means signal probe cocktail which is where the amplicon is mixed with the signal probe. Detection zones A, B, C and D is where detection takes place. The drops 1, 2, 3, and 4 are moved into the detection zone as shown. The gold plated electrode is depicted as small round circles in the detection zone. cDT-8 and cDT-9 are the controls used. cDT-8 uses a ferrocene derivative QW56. cDT-9 uses a ferrocene derivative QW56. The RTD temperature set points are shown in degrees Celsius.

FIG. 23: A notice showing that if the BCID Panel is used to test BacT/ALERT SN bottles, positives for *Pseudomonas aeruginosa* and *Enterococcus* should be reconfirmed by another method prior to reporting the test results.

DEFINITIONS

Figure 1:
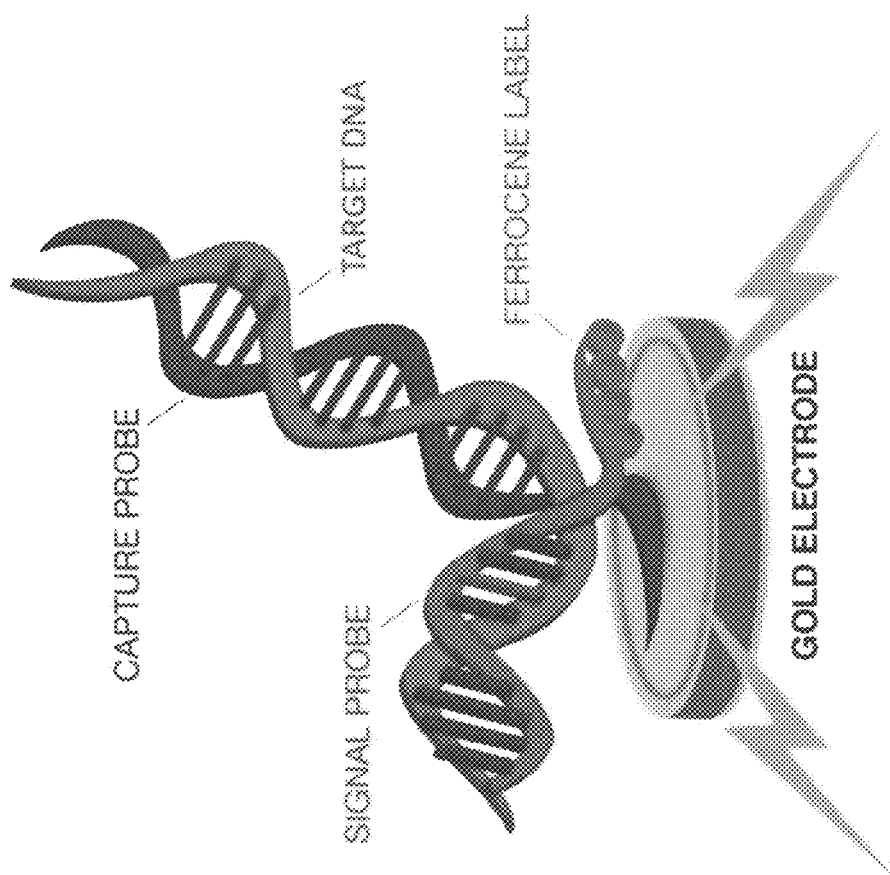
FIG. 1: Shows a schematic of a hybridization complex.

"Target nucleic acid," or "analyte of interest", or "target molecule" or "human pathogen nucleic acid", include genes, portions of genes, regulatory sequences of genes, mRNAs, rRNAs, tRNAs, siRNAs, cDNA and may be single stranded, double stranded or triple stranded. As discussed herein, target nucleic acids are DNA from human pathogens, and are naturally occurring nucleic acids, as contrasted to the nucleic acids of capture probes and signal probes, which may include non-naturally occurring components. Some nucleic acid targets have polymorphisms, single nucleotide polymorphisms, deletions and alternate splice sequences, such as allelic variants. Multiple target domains may exist in a single molecule, for example, a target nucleic acid may have a first target domain that binds the capture probe and a second target domain that binds a signal probe, and/or distinct primer binding sequences. Target nucleic acids are not generally provided with the cartridge as manufactured, but are contained in the liquid sample to be assayed; in contrast, "control analytes" or "control nucleic acids" are typically provided with the cartridge or are routinely present in a sample of a particular type and are assayed in order to ensure proper performance of the assay. Spiked samples may be used in certain quality control testing and for calibration, as is well known in the art. The target analyte is also referred to as "clinically relevant amplification" or "systemic infection" or "pathogen of interest" and is distinguished from, for example, contamination.

As used herein, the term "sample" is used in its broadest sense. In one sense, it is meant to include a specimen or culture obtained from any source, as well as biological and environmental samples. Biological samples may be obtained from animals (including humans) and encompass fluids, solids, tissues, and gases. Biological samples include blood products, such as plasma, serum and the like. In contrast with some commercial systems that require some off chip handling of the sample, generally including sample extraction (cell lysis, for example), and sample preparation prior to detection. Thus, in accordance with aspects of the current system, a sample is loaded onto a BCID cartridge and the target analyte is extracted, amplified as necessary (for example, when the target analyte is a nucleic acid using polymerase chain reaction (PCR) techniques, although isothermal amplification methods can be utilized as well), and then detected using electrochemical detection, all on a microfluidic platform, generally referred to herein as a "multiplex cartridge" or a "fluid sample processing cartridge." The BCID cartridge utilizes a sample preparation module as further described and shown in FIG. 15 of U.S. Pat. No. 9,598,722 (which is herein incorporated by reference in its entirty). In many embodiments, e.g. for the detection of human pathogens, the sample is a blood sample that is treated as outlined herein. Environmental samples include environmental material such as surface matter, soil, water, crystals and industrial samples. Such examples are not, however, to be construed as limiting the sample types applicable to the present technology.

By "nucleic acid" or "oligonucleotide" or grammatical equivalents herein means at least two nucleotides covalently linked together. A nucleic acid of the present invention will generally contain phosphodiester bonds, although in some cases, for example in the creation of signal probes and sometimes capture probes, nucleic acid analogs are included that may have alternate backbones, comprising, for example, phosphoramides, phosphorothioates, phosphorodithioates, Omethylphophoroamidite linkages and peptide nucleic acid backbones and linkages, as well as those with positive backbones, non-ionic backbones nonribose backbones, including those containing one or more carbocyclic sugars are also included within the definition of nucleic acids. These modifications of the ribosephosphate backbone may be done to facilitate the addition of electron transfer moieties, or to increase the stability and half-life of such molecules in physiological environments.

The term "detection system" as used herein refers to a method that enables visualization of PCR-amplified nucleic acid products. Examples of suitable detection systems include systems that depend on detection of color, radioactivity, fluorescence, chemiluminescence or electrochemical signals, with the latter finding particular use in the present invention.

The term "contamination" or "contaminant" or "background contamination" or "contaminating pathogen and/or genetic material" or "unwanted contamination" as used herein refers to nucleic acids in the sample which are not a part of the nucleic acid population that is being targeted for amplification. For example, nucleic acids found in the blood culture matrix.

The term "de-escalation targets" means *Propionibacterium acnes, Staphylococcus epidermidis, Micrococcus, Lactobacillus* or *Corynebacterium*. An object of the invention is to distinguish between unwanted contamination (from blood culture bottles) and de-escalation targets (which may be present as a contamination from blood draw) but which may be a clinically relevant infection. An object of the invention is to distinguish between unwanted contamination, de-escalation targets, clinically relevant pathogens and determinants of antimicrobial resistance.

The term "infection" means the invasion of a host organism's body by another organism or entity (pathogen), for example, a fungi or bacteria. The meaning of the term "co-infection" as used herein means "double infection," "multiple infection," or "serial infection" and is used to denote simultaneous infection with two or more infections/pathogens.

The term "determinants of antimicrobial resistance" relates to a gene responsible for the development of resistance in the bacteria which actively counteracts the effect of an antibiotic. Particularly, genetic determinants of resistance to methicillin (mecA and mecC) and vancomycin (vanA and vanB) are envisaged. Genes associated with genetic determinants of resistance such as CTX-M, NDM, IMP, OXA, KPC, VIM are envisaged.

For some nucleic acid detection systems, the target sequence is generally amplified, and during amplification, a label is added. The compositions of the invention may additionally contain one or more labels at any position. By "label" herein is meant an element (e.g. an isotope) or chemical compound that is attached to enable the detection of the compound. Preferred labels are radioactive isotopic labels, and colored or fluorescent dyes. The labels may be incorporated into the compound at any position. In addition, the compositions of the invention may also contain other moieties such as cross-linking agents to facilitate cross-linking of the target-probe complex. See for example, Lukhtanov et al., Nucl. Acids. Res. 24(4):683 (1996) and Tabone et al., Biochem. 33:375 (1994), both of which are expressly incorporated by reference.

The electrochemical detection system used herein uses a separate singal probe or label probe having an electron transfer moiety (ETM). That is, one portion of the label probe directly or indirectly binds to the target analyte, and one portion comprises a recruitment linker comprising covalently attached ETMs. In some systems, these may be the same. In an embodiment, the ETM is responsive to an input waveform. In an embodiment, the ETM is a metallocene. In an embodiment, the metallocene is a ferrocene. In an embodiment, the ferrocene is a ferrocene derivative. Preferred ferrocene derivatives can be N6 (FIG. 1D as shown in U.S. application Ser. No. 14/218,615), QW56 (FIG. 2A as shown in U.S. application Ser. No. 14/218,615), and QW80 (FIG. 2B as shown in U.S. application Ser. No. 14/218,615).

The expression "electrochemical system" or "electrochemical detection system" or "automated nucleic acid testing system" refers to a system that determines the presence and/or quantity of a redox analyte through measurements of electrical signal in a solution between a working electrode and a counter electrode, such as induced by a redox reaction or electrical potential from the release or absorption of ions. The redox reaction refers to the loss of electrons (oxidation) or gain of electrons (reduction) that a material undergoes during electrical stimulation such as applying a potential. Redox reactions take place at the working electrode, and which, for chemical detection, is typically constructed from an inert material such as platinum or carbon. The potential of the working electrode is measured against a reference electrode, which is typically a stable, well-behaved electrochemical half-cell such as silver/ silver chloride. The electrochemical system can be used to support many different techniques for determining the presence and concentration of the target biomolecules including, but not limited to, various types of voltammetry, amperometry, potentiometry, coulometry, conductometry, and conductimetry such as AC voltammetry, differential pulse voltammetry, square wave voltammetry, electrochemical impedance spectroscopy, anodic stripping voltammetry, cyclic voltammetry, and fast scan cyclic voltammetry. The electrochemical system may further include one or more negative control electrode and a positive control electrode. In the context of the invention, a single electrochemical system may be used to detect and quantify more than one type of target analyte. The use of electrochemical systems is described in more detail in U.S. Pat. Nos. 9,557,295, 8,501, 921, 6,600,026, 6,740,518 and U.S. application Ser. No. 14/538,506 which are herein incorporated by reference in their entirety.

The term "pathogen" or "human pathogen" as used herein refers to an organism (bacteria or fungi) that may affect the health status of the host, if that host is infected by that organism. A large number of human pathogens are outlined in the Tables, Examples and Lists herein. Included within the definition of human pathogen is the genetic material, usually DNA, that is contained within the pathogenic organism. In addition, as will be appreciated by those in the art, included within the definition of the genetic material of a pathogen are amplicons that result from amplification reactions such as the PCR reactions described herein.

The term "analyzing the presence of a pathogen" is used to describe a method to determine the presence or absence of a pathogen. The systems and methods disclosed herein do not require additional analysis to discriminate between background signaling due to contamination effects and real pathogenic infections and thus enable a decision on whether to apply a selective antibiotic therapy.

The term "thresholding" or "threshold signal" or the like refers to a set signal level below which the reported call is "not detected," above which the reported call is "detected."

The term "PCR" means "polymerase chain reaction." PCR is a technique used in molecular biology to amplify a single copy or a few copies of a segment of DNA across several orders of magnitude, generating thousands to millions of copies of a particular DNA sequence. PCR reagents generally include pairs of primers, dNTPs and a DNA polyermase.

The term "single reaction" or "single run" or "single multiplex PCR" or "single PCR" or "single nucleic acid amplification reaction" or "single amplification" or the like in this context refers to a standard PCR operating program. A single PCR run encompasses non-uniform PCR cycling (also referred to as heterogeneous PCR cycling, non-harmonized, uneven, unsymmetrical, mismatched PCR cycling and the like) in a single cartridge, i.e., some samples being cycled 30 times while others are cycled 35 times but not two sequential PCR runs such as with nested PCR. If heterogeneous single run PCR cycling were not utilized, there would be either a risk of false positives for the organisms that tend to have high contamination concentrations (such as *Bacillus*) or a risk of false negatives for organisms that tend to have slower growth in culture and therefore fewer copies of target sequence in the sample (such as *E. Coli*), or both if a compromise cycle were chosen. Using heterogeneous single run PCR cycles for different organisms improves the overall accuracy of the assay. Herein, the standard PCR operating program comprises a series of repeated temperature changes, called cycles, with each cycle consisting of 2 discrete temperature steps, referred to as denaturation and annealing/extension steps. The cycling is preceded by a single temperature step (hot start) at a high temperature (>90° C.) for enzyme activation.

"Nucleotide" means a building block of DNA or RNA, consisting of one nitrogenous base, one phosphate molecule, and one sugar molecule (deoxyribose in DNA, ribose in RNA).

"Oligonucleotide" means a short string of nucleotides. Oligonucleotides are often used as probes to find a matching sequence of DNA or RNA and can be labeled with a variety of labels, such as radioisotopes and fluorescent and chemiluminescent moieties and ferrocene labels.

"Primer" means a short strand of oligonucleotides complementary to a specific target sequence of DNA, which is used to prime DNA synthesis. Some primer pools contain species-specific primers. Such species-specific primer pairs hybridize in the assay to a target nucleic acid sequence of only one of said target species (gram-positive bacterial, gram-negative bacterial or fungal). Some primer pools contain genus-specific primers. Each double stranded amplicon contains a blocking moiety (phosphorylation on one strand) so that exonuclease activity is blocked, thereby inhibiting digestion of the blocked strand and promoting digestion of the unblocked strand. Exonucleases are enzymes that work by cleaving nucleotides one at a time from the end (exo) of a polynucleotide chain. A hydrolyzing reaction that breaks phosphodiester bonds at either the 3' or the 5' end occurs.

"Uniplex" means a PCR-based assay utilizing a single set of primers in each reaction that amplifies a single pathogen specific nucleic acid sequence "Multiplex" means a PCR-based assay utilizing multiple primer sets in a single reaction, where each primer can amplify a single pathogen specific nucleic acid sequence.

"End point PCR" means one multiplexed PCR method for amplification and end point detection (i.e. after the log phase).

"Real-time PCR" or "Q-PCT" refers to a homogenous PCR assay that permits continuous fluorescent monitoring of the kinetic progress of the amplification reaction. Methods of conducting real-time PCR are well known in the art and a number of systems are available commercially (see e.g. Higucho et al., "Kinetic PCR Analysis: Real-time Monitoring of DNA Amplification Reactions," Bio/Technology 11:1026-1030 (1993))

The term "capture probe" refers to the nucleic acid sequence, specific to the individual pathogen that is immobilized on an inert matrix. When a capture probe is combined with other capture probes for simultaneous detection of multiple pathogens, the specificity of the capture probe should not be substantially affected by the presence of other capture probes, i.e., it still hybridizes to the target pathogens nucleic acid. Preferably, a capture probe selected for one pathogen does not hybridize to a nucleic acid from another pathogen. Capture probes generally hybridize to a first target domain of an amplicon of a human pathogen as outlined herein.

The term "signal probe" refers to the nucleic acid sequence, specific to the individual pathogen that is not immobilized on an inert matrix. Signal probes generally hybridize to a second target domain of an amplicon of a human pathogen as outlined herein, and they are generally labeled. Signaling probes in some embodiments are labeled with different labels that enable simultaneous use and differentiation between each of the labels. However, in the BCID-GP and GN panels disclosed the signaling probes are not labelled with different labels such that when the signaling probe binds, "pan-*candida* detection" is reported not the specific *candida* species detected (*Candida albicans, Candida glabrata, Candida krusei, Candida parapsilosis*).

By "pan-assay" or "pan-target" in the context of the invention herein is meant an assay that detects if a marker such as a gene is present in the sample and is reflective of the presence of a pathogen category such as a gram-positive bacteria, gram-negative bacteria or fungi. Pan-assays are characterized by the fact that they reflect the possibility of the presence of more than one pathogen in the sample. Thus, pan-assays are not specific for a single pathogen being present in the sample, but are specific for a pathogen type such as gram-positive, gram-negative or fungi in the sample.

"Hybridization" refers to the process of joining two complementary strands of nucleic acid to form a double-stranded molecule; more specifically mentioned here is hybridization between the 'probe (capture or signal)' and the 'target' nucleic acid sequences. In many embodiments, a "hybridization complex" comprises three nucleic acids: a target nucleic acid, a signal probe hybridized to a first target domain of the target nucleic acid and a capture probe hybridized to a second target domain of the target nucleic acid.

As used herein, the term "cartridge" or "consumable" is a Self-contained cartridge/consumable that includes the necessary components to perform a single BCID Panel test. A "cartridge" or "consumable" is a cartridge for performing assays in a closed sample preparation and reaction system as described in U.S. Pat. No. 9,598,722 which is herein incorporated by reference in its entirety. The invention provides cartridges comprising several components, including a biochip cartridge, a top plate, a liquid reagent module (LRM), and a housing that keeps the components together. The biochip cartage comprises a bottom substrate, a sample preparation zone, reagent zone, Sample Manipulation Zone, Amplification Zone, Detection Zones as further described in U.S. Patent Publication no. 2015/0323555 and U.S. Pat. No. 9,598,722 which are herein incorporated by reference in their entireties. Specifically, in the embodiments for detecting nucleic acid targets, the substrate comprises one or more amplification pathways/zones. The top plate is spotted with reagents and primers. During the spotting process, phenol red is added to the reagents and primers so that spotting can be visualized. The LRM includes fluid filled blisters, as generally depicted in FIG. 1 from U.S. Patent application publication no. 2014/0194305 which is herein incorporated by reference in its entirety. For example, lysis buffer (which in some cases can be water for hypotonic lysis, or can be a commercially available lysis buffer, such as those containing chiatropic salts such as guanidinium salts, and or high/low pH, and/or surfactants such as sodium dodecyl sulfate (SDS), Polysorbate 20, Triton-X, etc. is contained within a blister that is activated to add lysis buffer to the sample. These buffers and in particular Polysorbate 20 (such as Tween® 20) can be washed or they can remain in the sample upon amplification. The top plate may include a PDOT (or PEDOT) coating. PEDOT:PSS or poly(3,4-ethylenedioxythiophene) polystyrene sulfonate is a polymer mixture of two ionomers. One component in this mixture is made up of sodium polystyrene sulfonate which is a sulfonated polystyrene. Part of the sulfonyl groups are deprotonated and carry a negative charge. The other component poly(3,4-ethylenedioxythiophene) or PEDOT is a conjugated polymer and carries positive charges and is based on polythiophene. Together the charged macromolecules form a macromolecular salt. The top plate may be coated with Teflon®, Cytop®, or Fluoropel®, preferably Cytop®. Cytop® is an amorphous fluoropolymer with high optical transparency and excellent chemical, thermal, electrical and surface properties. As used herein, the term "cartridge sub-assembly" means the bottom plate and top plate together.

As used herein, the term BCID-GP means Blood Culture Identification—Gram-Positive Panel. The BCID-GP panel includes all of the oligonucleotides and reagents for carrying out a nucleic acid amplification reaction for the targets listed in FIG. 14 as well as the capture and signal probes to form the hybridization complex necessary to detect the targets listed in FIG. 14. Specifically, phenol red is included in the reagents and primer mix pools as a visual tool to ensure the top plates are properly spotted.

As used herein, the term BCID-GN means Blood Culture Identification—Gram-Negative Panel. The BCID-GN panel includes all of the oligonucleotides and reagents for carrying out a nucleic acid amplification reaction for the targets listed in FIG. 18 as well as the capture and signal probes to form the hybridization complex necessary to detect the targets listed in FIG. 18. Specifically, phenol red is included in the reagents and primer mix pools as a visual tool to ensure the top plates are properly spotted.

As used herein, the term BCID-FP means Blood Culture Identification—Fungal Panel. The BCID-FP panel includes all of the oligonucleotides and reagents for carrying out a nucleic acid amplification reaction for the targets listed in FIG. 21 as well as the capture and signal probes to form the hybridization complex necessary to detect the targets listed in FIG. 21. Specifically, phenol red is included in the reagents and primer mix pools as a visual tool to ensure the top plates are properly spotted.

As used herein, the term "BCID-GP cartridge" or "BCID-GN cartridge" or "BCID-FP cartridge" means a cartridge for performing gram-positive, gram-negative, or fungal assays respectively in a closed sample preparation and reaction system as described in U.S. Pat. No. 9,598,722 which is herein incorporated by reference in its entirety.

As used herein, the term "about" means encompassing plus or minus 10%. For example, about 90% refers to a range encompassing between 81% and 99% nucleotides. As used herein, the term "about" is synonymous with the term approximately.

Unless otherwise indicated or the context suggests otherwise, as used herein, "a" or "an" means "at least one" or "one or more."

The word "or" as used herein means any one member of a particular list and also includes any combination of members of that list.

The term "amplifying" or "amplification" in the context of nucleic acids refers to the production of multiple copies of a polynucleotide (generally referred to herein as "amplicons"), or a portion of the polynucleotide, typically starting from a small amount of the polynucleotide or a single polynucleotide molecule, where the amplification products or amplicons are generally detectable. Detection in the system ranges, for example, on the low end *C. Kefyr* is 200 CFU/mL without false positives due to contaminants. For fungal the upper detection limit for organisms is $1\times10^5$. For gram-negative bacteria the detection limit for organisms ranges from $1\times10^5$ to $1\times10^7$ without false positives due to contaminants. For gram-positive bacteria the detection limit for organisms ranges from $1\times10^5$ to $1\times10^8$ without false positives due to contaminants.

Amplification of polynucleotides encompasses a variety of chemical and enzymatic processes. The generation of multiple nucleic acid copies from one or a few copies of a target or template nucleic acid molecule during a polymerase chain reaction (PCR) or a ligase chain reaction (LCR) are forms of amplification.

The term "detect", "detecting" or "detection" refers to an act of determining the existence or presence of one or more targets (e.g., microorganism nucleic acids, amplicons, etc.) in a sample. As used herein, target detection occurs when the amplicon forms a hybridization complex with the complimentary signal and capture probe.

Amplicon—double-stranded nucleic acid product of PCR. Generally, the amplicon comprises a length that is compatible with electrochemical detection which is typically less than 300 base pairs although many amplicons used herein are less than 150; indeed some amplicons used in the system are less than 100 base pairs. Preferably the amplicon is less than 300 base pairs, 200 base pairs, 150 base pairs, 100 base pairs, or 75 base pairs. Generally, the goal is to make a short amplicon because it is more efficient for exonuclease to make it single strand and also requires shorter amplification times.

"Bay" or "instrument bay" or "cartridge bay"—Standalone processing unit which runs a consumable. Bays as used herein are further described in U.S. patent application Ser. No. 14/062,860, U.S. Patent Publication no. 2015/0323555 and U.S. Pat. No. 9,598,722 which are herein incorporated by reference in their entireties.

Exonuclease digestion—enzyme-driven process digesting double-stranded nucleic acid to single-stranded nucleic acid fragments. Exonuclease activity is blocked by phosphorylating one strand, thereby inhibiting digestion of the blocked strand and promoting digestion of the unblocked strand.

RTD—Temperature set point that is controlled by a feedback loop from the resistance temperature detectors (RTDs) to the Thermistor on the bay.

sLRM—"simulated liquid reagent module", a blood culture sample that is manually prepared on the bench to mimic processing on an automated instrument.

"Open bay" means an bay lacking the top plate bay component so only cartridge-related functions can be performed NTC sLRM=No Template Control sLRM is a sLRM prepared without positive blood culture or bacterial targets NTC—No template control

DETAILED DESCRIPTION OF THE INVENTION

While aspects of the subject matter of the present disclosure may be embodied in a variety of forms, the following description and accompanying drawings are merely intended to disclose some of these forms as specific examples of the subject matter. Accordingly, the subject matter of this disclosure is not intended to be limited to the forms or embodiments so described and illustrated.

Unless defined otherwise, all terms of art, notations and other technical terms or terminology used herein have the same meaning as is commonly understood by one of ordinary skill in the art to which this disclosure belongs. All patents, applications, published applications and other publications referred to herein are incorporated by reference in their entirety. If a definition set forth in this section is contrary to or otherwise inconsistent with a definition set forth in the patents, applications, published applications, and other publications that are herein incorporated by reference, the definition set forth in this section prevails over the definition that is incorporated herein by reference.

I. Introduction

The present disclosure relates to methods and systems for distinguishing between background contamination and clinically relevant infection. As noted above, the ability to detect pathogen infections in humans is hampered by background contamination present in the blood culture bottles used during gram-staining, the first step in many diagnoses. The present invention can distinguish between background contamination and the pathogen, including situations where the patient has more than one infection (e.g. a primary infection and a co-infection). The present invention can further identify the presence of de-escalation targets in a sample wherein the de-escalation target is *Propionibacterium acnes, Staphylococcus epidermidis, Micrococcus, Lactobacillus* or *Corynebacterium*.

The methods and systems can further distinguish between gram-positive, gram-negative and fungal infection(s). The methods and systems can further detect and identify antimicrobial resistance genes. If the infection is gram-positive or gram-negative the species of the infection can be identified. If a co-infection is present, and is of the same category as the infection (both gram positive or both gram negative), then the species of the co-infection can be identified. If a co-infection is present and is of a different category (infection is GP and co-infection is GN or fungal for example), the genus of the fungal co-infection can be identified and the category (Gram-negative) of the co-infection can be identified. If the co-infection is of a different category than the infection, the species of the co-infection can be identified by applying a two-step detection method. Further, the methods and systems identify the genus of an organism which is likely to be a contaminating organisms from a blood draw. Further, the methods and systems identify the presence of *Propionibacterium acnes, Staphylococcus epidermidis, Micrococcus, Lactobacillus* or *Corynebacterium* which are de-escalation targets.

This technical solution solves the problem stated above, namely, it enables the detection and/or identification of a human pathogen (i.e., the amplified human pathogen hybridized to a signal and capture probe is detected) with elimination and/or reduction of false positives due to contamination, thereby enabling informed decisions to be made regarding antibiotic stewardship.

In an embodiment, the application of PCR using a multiplex PCR method enables a substantial reduction in electrochemical detection of contaminating pathogen and/or genetic material present in the sample while allowing infectious bacteria and/or fungi to be detected. Detection occurs when the infectious bacteria and/or fungi are amplified and the amplicon hybridizes with a signal and/or capture probe.

One aspect of the invention discloses methods and devices for identifying which of a plurality of target nucleic acids is in a sample. The disclosed methods comprise providing a sample to the cartridge, providing PCR regents (including, but not limited to primers, dNTPs, DNA polymerase, exonucleases, etc.) for amplifying a locus from a different one of a plurality of target nucleic acid sequence to the sample, subjecting the sample to amplification conditions through a number of amplification cycles, detecting whether amplification has occurred, and identifying the target nucleic acid present in the sample wherein identifying comprises determining if the target nucleic acid is hybridized to signal and capture probes. In one embodiment, non-uniform PCR cycling is used in a single cartridge, i.e., a single cartridge may cycle a sample and a first set of primers 30 times and cycle the sample and a second different set of primers 35 times (based on using different locations on the cartridge; reference is made to FIG. 15).

The overall method of the invention is preferably substantially specific regarding the identification of the pathogen. An infectious pathogen can be identified by its species. A co-infectious pathogen which is of the same type as the infection (both are gram-positive, both are gram-negative or both are fungal) can be identified by its species. A co-infectious pathogen which is not the same type as the infection (the infection is gram-positive and co-infection is gram-negative or fungal; the infection is gram-negative and the co-infection is gram-positive or fungal), can be identified by its species.

Co-infectious pathogens not being a member of a predetermined group (pan-fungal or pan-gram-negative for the BCID-GP panel; or pan-fungal or pan gram-positive for the BCID-GN panel) are not identified because the steps performed with the reagents are adjusted to not detect pathogens not belonging to that group. In a preferred embodiment, 20-30 infectious pathogens can be identified on a single cartridge by its species or genus using a single PCR run while simultaneously being able to distinguish between systemic infection and punitive contamination. In a preferred embodiment, 30-40 or 40-50 infectious pathogens can be identified on a single cartridge by its species or genus using a single PCR run while simultaneously being able to distinguish between systemic infection and punitive contamination. In a preferred embodiment, at least 20, 20-60; 30-40 or 40-50 infectious pathogens can be identified on a single cartridge by its species or genus using a single PCR run while simultaneously being able to distinguish between systemic infection and punitive contamination and while simultaneously identifying fungal and bacteria co-infections by genus (fungal) or category (gram positive or gram negative).

Purification

Purification, partial purification or isolation of nucleic acids (e.g. DNA) from the clinical sample after gram staining is not needed to achieve sufficient sensitivity for detecting an infection while not detecting contaminants in the sample. Particularly, the nucleic acids need not be separated from proteins, sugars, and salts present in the original clinical sample. It is not necessary to partially or even completely isolate nucleic acid from the clinical sample after gram staining.

Alternatively, the nucleic acid target (genome, gene or gene fragment (e.g., a restriction fragment) of the pathogen) may be in a purified, or in an isolated form.

Alternatively, the sample may be treated with a compound which hydrolyzes nucleic acids aka a nuclease before amplification. Specifically, the sample may be treated with DNase I, Benzonase, or S1 nuclease before amplification, preferably before cell lysis.

Primer Amplification

In general, the design of amplification primers is performed on the basis of available sequence information with regard to the pre-selected target nucleic acid sequence regions of the specific pathogenic gram-positive bacteria to be amplified as well as with regard to the homologous sequences of those gram-positive and gram-negative bacteria, which shall not be amplified. More precisely, the set or sets of amplification primers are selected in such a way that there is a maximum sequence complementarity with respect to all target nucleic acid sequences of the selected predetermined pathogenic gram-positive bacteria species or genus, and, on the other hand, a minimum sequence complementarity with respect to nucleic acid sequences of all other non-selected gram-positive bacteria, gram-negative bacteria, i.e. those not belonging to the predetermined group or not being pathogenic, as well as fungi. The same method is applied to the BCID-GN cartridge and BCID-FN cartridge.

The invention surprisingly shows that the analysis of fungi is possible in a single PCR reaction, without a nested PCR approach, in such a manner that a highly sensitive and very specific method is provided. This is surprising as generally, due to the slower growth of fungal infections, the fungal pathogens are present in lower amounts in the sample, and, thus, signal from contaminants can compete with the actual signal from the fungal pathogen. Previous attempts at PCR followed by detection have been bothered by high levels of false positives caused by contaminating pathogen and/or genetic material present in the sample and/or media bottle. See U.S. Application no. 2015/0232916. The invention is, therefore, the first described single-run multiplex PCR method for discrimination between contaminating pathogen and/or genetic material present in the sample and infectious pathogen combined with discrimination between gram-positive pathogens, gram-negative bacterial pathogens, and fungal pathogens in said sample as well as antimicrobial resistance genes. The complexity of the present method is significantly reduced compared to alternative amplification schemes described previously, thereby increasing the user friendliness and reproducibility compared to those methods of the prior art.

In an embodiment of the invention, the method is characterized in that the PCR reaction comprises oligonucleotides that bind a DNA/nucleic acid sequence of a bacterial pathogen. In another embodiment, the method of the invention is characterized in that the oligonucleotides capable of binding a sequence of a bacterial pathogen enable discrimination between gram-positive and gram-negative bacteria. In one embodiment the method of the invention is characterized in that the oligonucleotides capable of binding a DNA/nucleic acid sequence of a bacterial pathogen which, once amplified, attach to probes labeled so as to be distinguished from each other.

In an embodiment, the oligonucleotides designed for DNA amplification are able to amplify genetic material from a single pathogenic or potentially pathogenic bacteria (i.e. specific for sequence variation of a particular species or genus of a gram-positive bacteria) allowing detection of a specific species or genus of gram-positive bacterial infection and are run with oligonucleotides that detect the fungal genus or gram-negative genus and, as a result, is a broad-band, gram-negative bacterial and fungal detection method. Likewise, in an embodiment, the oligonucleotides designed for DNA amplification allow detection of a specific gram-negative bacterial infection (i.e. specific for sequence variation of a particular species or genus of a gram-negative bacteria) and are run with oligonucleotides that detect the fungal genus or the gram-positive bacteria genus or species but do not identify gram-positive or fungal infections by genus or species and, as a result, is a broad-band, gram-positive bacterial or fungal and detection method.

In an embodiment of the invention, the method is characterized in that the PCR reaction comprises oligonucleotides that bind a DNA sequence of a fungal pathogen. In one embodiment the method of the invention is characterized in that the oligonucleotides capable of binding a DNA sequence of a fungal pathogen which, once amplified, attach to probes labeled so as to be distinguished from each other.

In a surprising manner, the oligonucleotides designed for fungal DNA amplification are able to amplify genetic material from a single pathogenic or potentially pathogenic fungi (i.e. specific for sequence variation of a particular species or genus of fungi) allowing detection of a specific fungal infection and do not detect contaminating pathogen and/or genetic material present in the sample.

Probes

In one embodiment the method of the invention is characterized in that the signal probes comprise electrochemical labels, wherein multiple probes may be identified and differentiated from one another on the basis of distinct labels that emit electrical signals at different voltages from each other; see for example, U.S. Pat. No. 7,935,481 and U.S. patent application Ser. No. 10/137,710 (which are hereby incorporated by reference in their entirety) which disclose a plurality of probes each with at least one ETM with a unique redox potential. This is analogous to the "two color" or "four color" idea of competitive hybridization, and is also analogous to sequencing by hybridization. Probes and labels may be selected as required depending on the device used for analysis and the sample to be assessed as known by those skilled in the art. Preferred labels for signal probes include ferrocene and ferrocene derivatives. Ferrocene undergoes many reactions characteristic of aromatic compounds, enabling the preparation of substituted derivatives. Ferrocene derivatives (such as N6, QW56, and QW80) and are generally covalently attached to the signal probes.

Single PCR Run

In an embodiment the method of the invention is carried out in a single multiplex, end point (PCR) reaction, otherwise known as a single PCR run (to be distinguished from nested PCR).

The invention is therefore characterized by the reduced number of PCR runs (single run) employed in the method compared to the prior art. The invention is therefore characterized by the reduced number of primers employed in the method compared to the prior art. The invention is therefore characterized by the reduced number of PCR runs (single run), PCR cycles (40, 35 or 30) and primers employed in the method compared to the prior art.

The invention is characterized in that some targets are detected with a 35 PCR cycle while other targets are detected with reduced PCR cycling (30) but there is a single PCR run. As such, the invention is characterized in that there is a single PCR run of the sample in a single cartridge.

Detuning

Figure 23:
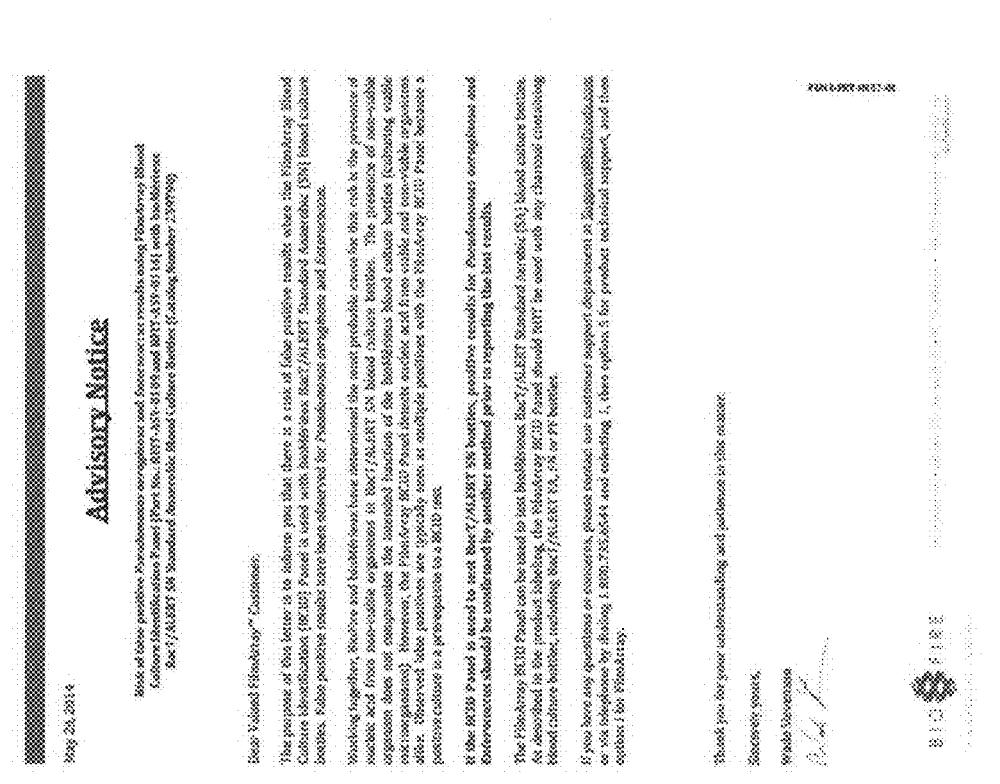

In recent years, there has been a growing demand for quick and highly sensitive systems for detecting infectious diseases. New systems use a reverse transcription-PCR and nested PCT to increase assay sensitivity. But with increased sensitivity, false positive results may occur. Indeed, there is a risk of false positives for *Pseudomonas aeruginosa* and *Enterococcus* results using bioMérieux BacT/ALERT SN Standard Anaerobic Blood Culture Bottles (Catalog Number 259790). See FIG. 23.

The art teaches that "tuning" the number of PCR cycles when using nested PCT can minimize false positive calls from background contamination, cross-reactivity (which can be problematic in a highly multiplexed reaction), and other extraneous amplification. See U.S. Patent application no. US20150232916 which is herein incorporated by reference in its entirety. However such approaches require nested PCR to achieve the necessary sensitivity. Indeed, a single run PCR with reduced cycling (less than 40 cycles) may be insufficient to detect some organisms because they amplify much later, because of slower growth in culture, less efficient PCR, or because there are fewer copies of the target sequence in a positive blood culture. Indeed, the BCID-FP panel cycles 40 times because fungi is known to grow slower in culture and the assay is detuned by having primer mismatches or having dual zone detection. Additionally, a single run PCR with reduced cycling (less than 40 cycles) could result in false negatives because a single PCR run is insufficient to amplify and detect the organism. It was surprising and unexpected that the balance of sensitivity (detection of low titer infectious organisms) and non-detection of contaminates could be achieved in a single PCR run using end-point PCR not nested PCR.

Prior to Applicant's discovery, the vast number of organisms' nucleic acid in blood culture bottles was not recognized in the field. Table 5 below shows that over 20 contaminating organisms' DNA is found in blood culture bottles. It was further surprising that the assays could be detuned in such a way that only clinically relevant detection was achieved given the vast number of organisms' DNA detected in blood culture bottles. It was further surprising that the assays could be detuned in such a way that only clinically relevant detection was achieved regardless of the blood culture bottle used (sensitivity is not limited to a particular blood culture bottle type).

Indeed, the ability to de-tune the assay is hampered by the system's four-track PCR configuration. With such a system only two PCR cycles can be run at a time because when lanes 1-4 are being denatured, lanes 5-8 are being amplified (See FIG. 15). It was surprising that clinically relevant infection could be distinguished from background contamination for the vast number of contaminating organisms detected in empty bottles using only 2 PCR cycling conditions (a.k.a., a single PCR run with two mismatched PCR cycles) in the cartridge.

The invention is characterized in that the electrochemical detection system employed, needed to be made less sensitive, "detuned," to eliminate or reduce detection of contaminants while remaining sensitive enough to detect clinically relevant infection. Detuning was achieved by reducing the PCR cycles in each single PCR run, increasing or decreasing the primer concentration, thresholding, primer mismatch and/or requiring one pathogen be detected in two detection zones. While the molecular biology techniques used to detune were known, no one had applied them in the context of electrochemical detection in a single run PCR to detect pathogens but not background contamination. In this way, applicants were able to reduce false positives from bottle contaminates to less than 5%, preferably less than 4%, preferably less than 3%, preferably less than 2%, preferably less than 1%, preferably less than 0.5%, preferably less than 0.1%, preferably less than 0.0.5%, preferably between 0.05%-5%, preferably between 0.5%-1%, preferably between 0.5%-3%, preferably between 0.01%-1%. Further, prior to Applicant, no one had applied a single run end-point PCR utilizing two mismatched PCR cycles to detect clinically relevant pathogens but not background contamination. Prior to Applicant, no one had applied a single run end-point PCR utilizing two mismatched PCR cycles to detect about 23 clinically relevant pathogens by genus and identify about 15 by their species but not background contamination. Prior to Applicant, no one had applied a single run end-point PCR utilizing two mismatched PCR cycles to detect 15-30 clinically relevant pathogens by genus and identify about 10-30 by their species but not background contamination. Another problem associated with nested PCR is that because there are two amplifications the number of reagents and primers needed is high compared to a single PCR run. As such, nested PCT systems cannot detect as many organisms as a system utilizing a single PCR run. As such, nested PCT systems tend to be focused on genus calls as opposed to species calls, like the invention. As such, only a broadband antibiotic therapeutic approach is possible when a nested PCT system identifying only genus calls is used, which may, in fact, be poorly suited for the particular pathogen.

The invention can be further understood by the following numbered paragraphs:

Paragraph 1. A method for identifying which of a plurality of organisms is in a sample, comprising: (a) providing a plurality of sample wells, each sample well provided with a portion of the sample and primers for amplifying a target nucleic acid sequence from a different one of the plurality of organisms, subjecting the plurality of sample wells to a single amplification having a number of predetermined amplification cycles, detecting whether amplification has occurred in each of a second set of the plurality of sample wells, identifying at least one organism present in the sample.

Paragraph 2: The method of paragraph 1, further comprising subjecting the plurality of sample wells to a single amplification condition wherein the number of predetermined amplification cycles can be mismatched.

Paragraph 3: The method of paragraph 1, further comprising subjecting the plurality of sample wells to a single amplification condition wherein the number of predetermined amplification cycles is 30 or 35.

Paragraph 4. A method for identifying which of a plurality of organisms is in a sample, comprising: (a) providing a plurality of sample wells, each sample well provided with a portion of the sample and primers for amplifying a target nucleic acid sequence from a different one of the plurality of organisms, subjecting the plurality of sample wells to a single amplification having a heterogeneous number of amplification cycles, detecting whether amplification has occurred in each of a second set of the plurality of sample wells, identifying at least one organism present in the sample.

Antibiotic Stewardship

In an embodiment, the method of the invention is characterized in that the sample is obtained from a subject exhibiting one or more symptoms of systemic inflammatory response syndrome (SIRS), sepsis, severe sepsis and/or septic shock. A significant benefit of this approach is the ability to subsequently prescribe an appropriate medicament during treatment. In light of the knowledge regarding bacterial (gram-positive, gram-negative) or fungal pathogen presence (as well as its resistance profile), an appropriate antibiotic or an appropriate anti-fungal can be selected for treatment, thereby avoiding potentially useless antibiotic treatments and associated financial, health and environmental disadvantages.

Patient care and antibiotic stewardship would be advanced by development and application of rapid diagnostics that provide accurate and timely information as to the nature of the infecting pathogen, including whether it is gram-positive bacterial, gram-negative bacterial, fungal and its resistance profile.

The BCID-GP, GN and FP Panels also includes several targets for organisms known to be common blood culture contaminants to aid in rapidly ruling out blood culture contamination. Other molecular panels include only coagulase negative *Staphylococcus* (CoNS) while the BCID panel includes *Bacillus subtilis* group, *Corynebacterium*, *Lactobacillus* group, *Micrococcus* and *Propionibacterium acnes* in addition to CoNS.

This is important because studies have shown that up to 15-30% of positive blood cultures may be contaminants depending on the lab. So being able to quickly determine a contaminant from a true infection means clinicians can more rapidly de-escalate unnecessary antibiotics and get patients out of the hospital quickly, instead of waiting 2-3 days for identification and antimicrobial susceptibility testing (AST). That also limits the adverse outcomes from unnecessary antibiotics.

*Propionibacterium acnes, Staphylococcus epidermidis, Micrococcus, Lactobacillus* or *Corynebacterium* can be true pathogens but in order for clinicians to determine a true pathogen from a contaminant they will look at several factors including: whether or not the patient is immunocompromised, the number of blood culture bottles that rang positive (if more than one, it is considered a true pathogen), time to bottle positivity compared to other bottles (If a bottle rings positive later than others it is often considered a contaminant because the bacterial load is generally lower) and other clinical symptoms.

Specifically, when contamination occurs at blood draw there is a positive gram stain and the physician can begin treatment. *Propionibacterium acnes, Staphylococcus epidermidis, Micrococcus, Lactobacillus* and *Corynebacterium* on the BCID-GP GN and FP panels are referred to as "de-escalation targets." When these targets are positive on the BCID panels and/or gram stain, the physician can evaluate whether the organism detected is likely the result of a blood infection or sample contamination. Sample contamination is especially likely when organisms such as *Propionibacterium acnes, Staphylococcus epidermidis, Micrococcus, Lactobacillus* and *Corynebacterium* are identified in one patient sample but not the other. When these are identified the physician or laboratory can verify infection by a second method. Although, sometimes the detection of these targets are technically a contamination, the identification of these on the BCID-GP GN and FP panels leads to clinically actionable data because the physician can evaluate whether the organism detected is likely the result of a blood infection or sample contamination.

In one embodiment the method of the invention is characterized in that patient treatment is altered or started based on the results from a BCID-GP, BCID-GN, or BCID-FP assay.

In one embodiment, an initial analysis is performed on a first sample to determine whether or not one or more common contaminants (such as *Propionibacterium acnes, Staphylococcus epidermidis, Micrococcus, Lactobacillus* or *Corynebacterium*) are present in a sample. If this initial analysis indicates that the common contaminant is present, a second analysis is performed to determine if the common contaminant is present in a second sample. If the common contaminant is not present in a second analysis then it is presumed the first sample was contaminated.

The invention can be further understood by the below numbered paragraphs:

Paragraph 1: An in vitro method for the detection and/or identification of a hybridization complex comprising a human pathogen and/or genetic material thereof hybridized to a signal probe and a capture probe comprising: subjecting a sample comprising or suspected of comprising a human pathogen and/or genetic material thereof to a single multiplex polymerase chain reaction (PCR), wherein said method comprises amplification of PCR products under conditions appropriate for the substantial reduction in detection of contaminating pathogen and/or genetic material present in the sample from blood culture bottles, and detecting the binding between the human pathogen and/or genetic material thereof and the signal probe and a capture probe and detecting the binding between *Propionibacterium acnes, Staphylococcus epidermidis, Micrococcus, Lactobacillus* or *Corynebacterium* and the signal probe and a capture probe.

Paragraph 2: The in vitro method of paragraph 1, wherein the detection of *Propionibacterium acnes, Staphylococcus epidermidis, Micrococcus, Lactobacillus* or *Corynebacterium* is compared to a second detection method and/or factor such as whether or not the patient is immunocompromised, the number of blood culture bottles that rang positive (if more than one, it is considered a true pathogen), time to bottle positivity compared to other bottles (If a bottle rings positive later than others it is often considered a contaminant because the bacterial load is generally lower) and other clinical symptoms.

Paragraph 3: The in vitro method of paragraph 2, wherein if the second detection method does not detect *Propionibacterium acnes, Staphylococcus epidermidis, Micrococcus, Lactobacillus* or *Corynebacterium* then the detection of *Propionibacterium acnes, Staphylococcus epidermidis, Micrococcus, Lactobacillus* or *Corynebacterium* rules out infection by *Propionibacterium acnes, Staphylococcus epidermidis, Micrococcus, Lactobacillus* or *Corynebacterium*.

Paragraph 4: An in vitro method for ruling out infection in a patient comprising: subjecting a sample comprising or suspected of comprising a human pathogen and/or genetic material thereof and a contaminate to a single multiplex polymerase chain reaction (PCR), and detecting the binding between the human pathogen and/or genetic material thereof and the signal probe and a capture probe and detecting the binding between *Propionibacterium acnes, Staphylococcus epidermidis, Micrococcus, Lactobacillus* or *Corynebacterium* and a signal probe and a capture probe wherein the detection of *Propionibacterium acnes, Staphylococcus epidermidis, Micrococcus, Lactobacillus* or *Corynebacterium* rules out infection by *Propionibacterium acnes, Staphylococcus epidermidis, Micrococcus, Lactobacillus* or *Corynebacterium*.

Paragraph 5: An in vitro method for determining if a sample is contaminated comprising: subjecting a sample comprising or suspected of comprising a human pathogen and/or genetic material thereof to a single multiplex polymerase chain reaction (PCR), and detecting the binding between the human pathogen and/or genetic material thereof and the signal probe and a capture probe and detecting the binding between *Propionibacterium acnes, Staphylococcus epidermidis, Micrococcus, Lactobacillus* or *Corynebacterium* and a signal probe and a capture probe wherein the detection of *Propionibacterium acnes, Staphylococcus epidermidis, Micrococcus, Lactobacillus* or *Corynebacterium* indicates the sample was likely contaminated. In embodiments, the method can further differentiate between gram-positive bacteria, gram-negative bacteria, fungi and determinates for antimicrobial resistance. In embodiments, the method can further identify the gram-positive bacteria species, gram-negative bacteria species, or fungi species. In embodiments, the method can further identify a co-infection if present in the sample by genus or type (gram-positive bacteria, gram-negative bacteria).

Paragraph 6: A method for testing a blood sample for the presence of a possible contaminant and a human pathogen and/or genetic material thereof, that reduces the risk of a false positive indication for contaminations frequently present in blood samples, the method comprising the steps of: obtaining a sample; subjecting the sample comprising or suspected of comprising a contamination or human pathogen and/or genetic material thereof to a single multiplex polymerase chain reaction (PCR), and detecting the binding between the possible contaminant and the signal probe and a capture probe; and detecting binding between the human pathogen and/or genetic material thereof and the signal probe and a capture probe wherein when binding between *Propionibacterium acnes, Staphylococcus epidermidis, Micrococcus, Lactobacillus* or *Corynebacterium* and a signal probe and a capture probe is detected, there is a possible contamination. In embodiments, the method can further differentiate between gram-positive bacteria, gram-negative bacteria, fungi and determinates for antimicrobial resistance. In embodiments, the method can further identify the gram-positive bacteria species, gram-negative bacteria species, or fungi species. In embodiments, the method can further identify a co-infection if present in the sample by genus or type (gram-positive bacteria, gram-negative bacteria).

Paragraph 7: A method for testing a blood sample for the presence of a possible contaminant and a human pathogen and/or genetic material thereof, that reduces the risk of a false positive indication for contaminations frequently present in blood samples, the method comprising the steps of: obtaining a sample; subjecting the sample comprising or suspected of comprising a contamination or human pathogen and/or genetic material thereof to a single multiplex polymerase chain reaction (PCR) wherein said method comprises amplification of PCR products under conditions appropriate for the substantial reduction in detection of contaminating pathogen and/or genetic material present in the sample as a result of blood culture bottle contamination, and detecting the binding between the possible contamination and the signal probe and a capture probe; and detecting binding between the human pathogen and/or genetic material thereof and the signal probe and a capture probe wherein when binding between the possible contamination (*Propionibacterium acnes, Staphylococcus epidermidis, Micrococcus, Lactobacillus* or *Corynebacterium*) and a signal probe and a capture probe is detected, there is a possible contamination.

Paragraph 8: A method for identifying the presence of a possible contaminant in a sample comprising: obtaining a sample; subjecting the sample comprising or suspected of comprising a contamination and/or human pathogen and/or genetic material thereof to a single multiplex polymerase chain reaction (PCR) wherein said method comprises amplification of PCR products under conditions appropriate for the substantial reduction in detection of the contaminating pathogen and/or genetic material present in the sample as a result of blood culture bottle contamination, and detecting the binding between the possible contaminant and the signal probe and a capture probe; and detecting binding between the human pathogen and/or genetic material thereof and the signal probe and a capture probe wherein when binding between the possible contaminant (*Propionibacterium acnes, Staphylococcus epidermidis, Micrococcus, Lactobacillus* or *Corynebacterium*) and a signal probe and a capture probe is detected, indicates the presence of a possible contaminant is identified. In embodiments, the method can further differentiate between gram-positive bacteria, gram-negative bacteria, fungi and determinates for antimicrobial resistance. In embodiments, the method can further identify the gram-positive bacteria species, gram-negative bacteria species, or fungi species. In embodiments, the method can further identify a co-infection if present in the sample by genus or type (gram-positive bacteria, gram-negative bacteria).

Paragraph 9: A method for identifying the presence of a de-escalation target in a sample comprising: obtaining a sample; subjecting the sample comprising or suspected of comprising a human pathogen and/or genetic material thereof to a single multiplex polymerase chain reaction (PCR) wherein said method comprises amplification of PCR products under conditions appropriate for the substantial reduction in detection of the contaminating pathogen and/or genetic material present in the sample as a result of blood culture bottle contamination, and detecting the binding between the de-escalation target and the signal probe and a capture probe; and detecting binding between the human pathogen and/or genetic material thereof and the signal probe and a capture probe. In embodiments, the method can further differentiate between gram-positive bacteria, gram-negative bacteria, fungi and determinates for antimicrobial resistance. In embodiments, the method can further identify the gram-positive bacteria species, gram-negative bacteria species, or fungi species. In embodiments, the method can further identify a co-infection if present in the sample by genus or type (gram-positive bacteria, gram-negative bacteria).

Paragraph 10: A microfluidic device for the detection and/or identification of a human pathogen and/or genetic material thereof comprising: a mixture of oligonucleotides and reagents for carrying out a single nucleic acid amplification reaction capable of distinguishing between clinically relevant amplification and amplification from blood culture bottle contamination and further capable of identifying the presence of a de-escalation target in a sample wherein the de-escalation target is *Propionibacterium acnes, Staphylococcus epidermidis, Micrococcus, Lactobacillus* or *Corynebacterium*. In embodiments, the device can further differentiate between gram-positive bacteria, gram-negative bacteria, fungi and determinates for antimicrobial resistance. In embodiments, the device can further identify the gram-positive bacteria species, gram-negative bacteria species, or fungi species. In embodiments, the device can further identify a co-infection if present in the sample by genus or type (gram-positive bacteria, gram-negative bacteria).

Paragraph 11: A detection report identifying the presence of a possible contaminant in a sample wherein the possible contaminant is *Propionibacterium acnes, Staphylococcus epidermidis, Micrococcus, Lactobacillus* or *Corynebacterium*.

Paragraph 12: A detection report identifying the presence of a possible contaminant in a sample wherein the possible contaminant is *Propionibacterium acnes, Staphylococcus epidermidis, Micrococcus, Lactobacillus* or *Corynebacterium* and further identifying of a human pathogen and/or genetic material thereof comprising gram-positive bacteria, gram-negative bacteria or fungi. In some embodiments the gram-positive bacteria or gram-negative bacteria or fungi is identified by its species and a co-infection if present is identified by its genus or type (gram-positive or negative).

Paragraph 13: A detection report identifying the presence of a de-escalation target wherein the de-escalation target is *Propionibacterium acnes, Staphylococcus epidermidis, Micrococcus, Lactobacillus* or *Corynebacterium* and further identifying of a human pathogen and/or genetic material thereof comprising gram-positive bacteria, gram-negative bacteria or fungi. In some embodiments the gram-positive bacteria or gram-negative bacteria or fungi is identified by its species and a co-infection if present is identified by its genus or type (gram-positive or negative).

Paragraph 14: A method for distinguishing between unwanted contamination (from blood culture bottles) and possible contaminant (from blood draw) but which may be a clinically relevant infection the method comprising obtaining a sample; subjecting a sample comprising or suspected of comprising a human pathogen and/or genetic material thereof to a single multiplex polymerase chain reaction (PCR), wherein said method comprises amplification of PCR products under conditions appropriate for the substantial reduction in detection of unwanted contaminating pathogen and/or genetic material present in the sample and appropriate for the detection of possible contaminant in the sample wherein the possible contaminant is *Propionibacterium acnes, Staphylococcus epidermidis, Micrococcus, Lactobacillus* or *Corynebacterium*. In embodiments, the method can further differentiate between gram-positive bacteria, gram-negative bacteria, fungi and determinates for antimicrobial resistance. In embodiments, the device can further identify the gram-positive bacteria species, gram-negative bacteria species, or fungi species. In embodiments, the device can further identify a co-infection if present in the sample by genus or type (gram-positive bacteria, gram-negative bacteria).

Paragraph 15: A device for distinguishing between unwanted contamination (from blood culture bottles) and possible contaminant (from blood draw) but which may be a clinically relevant infection in a sample the device comprising: a mixture of oligonucleotides and reagents for carrying out a single nucleic acid amplification reaction capable of distinguishing between a possible contaminant and unwanted contamination. The device can further include a mixture of oligonucleotides and reagents for carrying out a single nucleic acid amplification reaction capable of distinguishing between clinically relevant pathogen and unwanted contamination and possible contamination. In embodiments, the device can further differentiate between gram-positive bacteria, gram-negative bacteria, fungi and determinates for antimicrobial resistance. In embodiments, the device can further identify the gram-positive bacteria species, gram-negative bacteria species, or fungi species. In embodiments, the device can further identify a co-infection if present in the sample by genus or type (gram-positive bacteria, gram-negative bacteria).

Method(s) of the Invention(s)

In one embodiment the method of the invention comprises or consists of the following steps: a) providing a sample, preferably a blood culture, blood, serum or plasma sample, b) after nucleic acid extraction, bringing said sample into contact with a mixture of oligonucleotides and reagents (as well as phenol red) for carrying out a nucleic acid amplification reaction, c) carrying out a single nucleic acid amplification reaction, and d) detecting and evaluating the amplification products generated as a result of said single nucleic acid amplification reaction.

In general, the method is suitable for detection of a bacteria or fungi from a sample. In general, the method is suitable for identification of a gram-positive bacteria, gram-negative bacteria or fungi from a sample. The identification of a pathogen may occur such that the detection report provides "fungal", "gram-positive" or "gram-negative" as an appropriate result. The identification of a pathogen may occur such that the detection report provides the fungal species name, gram-positive bacteria species name or gram-negative bacteria species name as an appropriate result. The identification of a pathogen may occur such that the detection report provides the fungal species or genus name, gram-positive bacteria species or genus name or gram-negative bacteria species or genus name as an appropriate result.

The identification of a pathogen may occur such that the detection report provides the gram-positive bacteria species or genus name, the fungal genus name and/or identifies gram-negative bacteria detection as an appropriate result. The identification of a pathogen may occur such that the detection report provides the gram-negative bacteria species or genus name, the fungal genus name and/or identifies gram-positive bacteria detection as an appropriate result.

Below summarizes the types of calls/reports for each BCID panel.

A method for reducing or eliminating false positives comprising the steps of: a) providing a sample b) after nucleic acid extraction contacting the sample with a mixture of oligonucleotides and reagents for carrying out a single nucleic acid amplification reaction capable of distinguishing between clinically relevant pathogen and endogenous or contaminating DNA thereby reducing or eliminating false positives. In some embodiments, after using the methods of the invention, false positives range from 0.001-5%, 0.001-3%, 0.001-1%, 0.05-1%, 0.1-1%.

A method for detecting the presence of a pathogen of interest in a sample, comprising the steps of: a) providing sample comprising a pathogen; b) after nucleic acid extraction contacting the sample with a mixture of oligonucleotides and reagents (including phenol red) for carrying out a single nucleic acid amplification reaction c) amplify under conditions appropriate for pathogen replication and the substantial reduction of endogenous or contaminating DNA replication; and d) detecting the presence of amplified pathogen in the sample.

The methods of detection may be carried out by amplification of the genetic material, by hybridization of the genetic material with oligonucleotides or by a combination of amplification and hybridization. A significant advantage of the invention is that the amplification step may be performed under similar or uniform amplification conditions for each pathogen species or genus. As such, amplification of each pathogen species or genus may be performed simultaneously. Detection of the genetic material may also advantageously be performed under uniform conditions.

It is an object of the invention to provide a method of detecting a nucleic acid sequence which reduces the number of false positives resulting from nucleic acid contamination in the sample (i.e., organisms or nucleic acid found in the blood culture bottle media). The present method increases the accuracy of the procedure without sacrificing clinically relevant sensitivity.

It is another object of the invention to provide a method of detecting a nucleic acid sequence which obviates the necessity to select a signaling threshold.

It is another object of the invention to provide methods and systems to detect nucleic acid sequences which identify blood culture draw contamination.

Device(s) of the Invention(s)

A microfluidic device for detecting a genetic material, comprising: a mixture of oligonucleotides and reagents (including phenol red) for carrying out a single nucleic acid amplification reaction capable of distinguishing between clinically relevant amplification and amplification from other sources such as from contamination. Wherein the mixture of oligonucleotides and reagents for carrying out a single nucleic acid amplification reaction is further capable of distinguishing between gram-positive, gram-negative, or fungal infection. Wherein the mixture of oligonucleotides and reagents for carrying out a single nucleic acid amplification reaction is further capable of identifying antimicrobial resistance. Wherein the mixture of oligonucleotides and reagents for carrying out a single nucleic acid amplification reaction is further capable of identifying the species of the infection and spices of a co-infection. Wherein the mixture of oligonucleotides and reagents for carrying out a single nucleic acid amplification reaction is further capable of identifying the species or genus of the infection and spices or genus of a co-infection. Wherein the mixture of oligonucleotides and reagents for carrying out a single nucleic acid amplification reaction is further capable of identifying the species or genus of the infection and spices or type (gram-positive or gram negative) of co-infection.

A cartridge comprising: a mixture of oligonucleotides and reagents for carrying out a single nucleic acid amplification reaction capable of distinguishing between clinically relevant amplification and amplification from other sources such as from background contamination. Wherein the mixture of oligonucleotides and reagents for carrying out a single nucleic acid amplification reaction is further capable of distinguishing between gram-positive, gram-negative, or fungal infection. Wherein the mixture of oligonucleotides and reagents for carrying out a single nucleic acid amplification reaction is further capable of identifying antimicrobial resistance. Wherein the mixture of oligonucleotides and reagents for carrying out a single nucleic acid amplification reaction is further capable of identifying the species of the infection and genus of a co-infection. Wherein the mixture of oligonucleotides and reagents for carrying out a single nucleic acid amplification reaction is further capable of identifying the species or genus of the infection and spices or genus of a co-infection. Wherein the mixture of oligonucleotides and reagents for carrying out a single nucleic acid amplification reaction is further capable of identifying the species or genus of the infection and spices or type (gram-positive or gram negative) of co-infection.

In some embodiments, gram-positive and gram-negative primers are in the same multiplex primer pool. In some embodiments, gram-positive and fungal primers are in the same multiplex primer pool. In some embodiments, gram-negative and fungal primers are in the same multiplex primer pool.

Gram-Positive

The Gram-Positive (BCID-GP) Panel is a fully automated, qualitative, nucleic acid, multiplex in vitro diagnostic test for the simultaneous qualitative detection and identification of multiple potentially pathogenic gram-positive bacterial organisms and select determinants of antimicrobial resistance in positive blood culture. In addition, the BCID-GP Panel also detects but does not differentiate Gram-Negative bacteria (Pan Gram-Negative assay giving a gram-negative call) and several *Candida* species (Pan *Candida* assay giving a *Candida* call) present in co-infections. The BCID-GP Panel is performed directly on blood culture samples identified as positive by a continuously monitoring blood culture system that demonstrate the presence of organisms as determined by Gram stain.

The BCID-GP Panel contains assays for the detection of genetic determinants of resistance to methicillin (mecA and mecC) and vancomycin (vanA and vanB) to aid in the identification of potentially antimicrobial resistant organisms in positive blood culture samples. The antimicrobial resistance gene detected may or may not be associated with the agent responsible for the disease.

The BCID-GP Panel also contains targets designed to detect a broad range of organisms with a potentially misleading Gram stain result or organisms that may be missed by Gram staining altogether for example in the case of co-infections. These include a broad Pan Gram-Negative assay as well as a Pan *Candida* assay, both of which may provide data to facilitate the correct testing algorithm. As such, the present disclosure relates to methods and systems for a) distinguishing between contamination and gram-positive bacterial infection, b) distinguishing between gram-positive bacterial species infection; c) distinguishing between some gram-positive bacterial species and some gram-positive genus infection(s); d) identifying but not differentiating gram-negative bacterial infection and fungal infection. The present disclosure further relates to methods and systems for identifying a pathogen that is likely a contamination from the blood draw.

The following bacterial organisms and resistance marker genes are identified using the BCID-GP Panel: *Bacillus cereus* group, *Staphylococcus epidermidis*, *Bacillus subtilis* group, *Staphylococcus lugdunensis*, *Corynebacterium* spp., *Streptococcus*, *Enterococcus*, *Streptococcus agalactiae*, *Enterococcus faecalis*, *Streptococcus anginosus* group, *Enterococcus faecium*, *Streptococcus pneumonia*, *Lactobacillus*, *Streptococcus pyogenes*, *Listeria*, Pan Gram-negative target (at least *Enterobacteriaceae*, *Acinetobacter*, *Pseudomonas*, *Bacteroides*, *Stenotrophomonas*), *Listeria monocytogenes*, Pan *Candida* target (*Candida albicans*, *Candida glabrata*, *Candida krusei*, *Candida parapsilosis*), *Micrococcus*, *Propionibacterium acnes*, *Staphylococcus*, *Staphylococcus aureus*, mecA, mecC, vanA, and vanB. Table 1 below shows that reported target call and the target species detected. Stated another way, some species are detected by the BCID-GP panel ("Targets detected" in Table 1 below) but not identified by the species in the call (report); instead, the call/report identifies the genus. Some species are detected by the BCID-GP panel ("Targets detected" in Table 1 below) and are identified by the species in the call (report). Some organisms can generate both the genus and species call.

TABLE 1

Analytes Detected by the BCID-GP Panel

| Calls | Reported Target | Targets Detected |
|---|---|---|
| 1 | *Streptococcus agalactiae* | *Streptococcus agalactiae* |
|   |   | *Streptococcus constellatus* |
| 2 | *Streptococcus anginosus* group | *Streptococcus intermedius* |
|   |   | *Streptococcus anginosus* |
| 3 | *Streptococcus pneumoniae* | *Streptococcus pneumoniae* |
| 4 | *Streptococcus pyogenes* | *Streptococcus pyogenes* |
| 5 | *Staphylococcus aureus* | *Staphylococcus aureus* |
| 6 | *Staphylococcus epidermidis* | *Staphylococcus epidermidis* |
| 7 | *Staphylococcus lugdunensis* | *Staphylococcus lugdunensis* |
| 8 | *Enterococcus faecalis* | *Enterococcus faecalis* |
| 9 | *Enterococcus faecium* | *Enterococcus faecium* |
| 10 | *Bacillus subtilis* group | *Bacillus amyloliquefaciens* |
|   |   | *Bacillus atrophaeus* |
|   |   | *Bacillus licheniformis* |
|   |   | *Bacillus subtilis* |
| 11 | *Bacillus cereus* group | *Bacillus anthracis* |
|   |   | *Bacillus cereus* |
|   |   | *Bacillus thuringiensis* |
| 12 | *Micrococcus* | *M. yunnanensis* |
|   |   | *M. alkanovora* |
|   |   | *M. aquilus* |
|   |   | *M. endophyticus* |
|   |   | *M. flavus* |
|   |   | *M. indicus* |
|   |   | *M. leuteus* |
|   |   | *M. thailandius* |
| 13 | *Corynebacterium* | *Corynebacterium jeikeium* |
|   |   | *Corynebacterium urealyticum* |
|   |   | *Corynebacterium diphtheriae* |
|   |   | *Corynebacterium ulcerans* |
|   |   | *Corynebacterium striatum* |
|   |   | And many more |

TABLE 1-continued

Analytes Detected by the BCID-GP Panel

| Calls | Reported Target | Targets Detected |
|---|---|---|
| 14 | *Listeria* | *Listeria innocua* |
|   |   | *Listeria ivanovii* |
|   |   | *Listeria seeligeri* |
|   |   | *Listeria welshimeri* |
| 15 | *Listeria monocytogenes* | *L. monocytogenes* |
| 16 | *Lactobacillus* | *Lactobacillus casei* |
|   |   | *Lactobacillus paracasei* |
|   |   | *Lactobacillus rhamnosus* |
| 17 | *Propionibacterium acnes* | *P. acnes* |
| 18 | *Enterococcus* | *Enterococcus avium* |
|   |   | *Enterococcus casseliflavus* |
|   |   | *Enterococcus faecalis* |
|   |   | *Enterococcus faecium* |
|   |   | *Enterococcus gallinarum* |
|   |   | *Enterococcus hirae* |
|   |   | *Enterococcus raffinosus* |
|   |   | *Enterococcus saccharolyticus* |
| 19 | *Streptococcus* | *Streptococcus agalactiae* |
|   |   | *Streptococcus constellatus* |
|   |   | *Streptococcus intermedius* |
|   |   | *Streptococcus anginosus* |
|   |   | *Streptococcus bovis* |
|   |   | *Streptococcus criceti* |
|   |   | *Streptococcus dysgalactiae* |
|   |   | *Streptococcus dysgalactiae* subsp *dysgalactiae* |
|   |   | *Streptococcus dysgalactiae* subsp *equisimilis* |
|   |   | *Streptococcus equi* |
|   |   | *Streptococcus equinus* |
|   |   | *Streptococcus gallolyricus* |
|   |   | *Streptococcus gallolyricus pasteurianus* |
|   |   | *Streptococcus gordonii* |
|   |   | *Streptococcus infantarius* |
|   |   | *Streptococcus infantis* |
|   |   | *Streptococcus mitis* |
|   |   | *Streptococcus mutans* |
|   |   | *Streptococcus oralis* |
|   |   | *Streptococcus parasanguinis* |
|   |   | *Streptococcus peroris* |
|   |   | *Streptococcus pneumoniae* |
|   |   | *Streptococcus pyogenes* |
|   |   | *Streptococcus salivarius* |
|   |   | *Streptococcus sanguinis* |
|   |   | *Streptococcus thoraltensis* |
| 20 | *Staphylococcus* | *Staphylococcus arlettae* |
|   |   | *Staphylococcus aureus* |
|   |   | *Staphylococcus auriculari* |
|   |   | *Staphylococcus capitis* |
|   |   | *Staphylococcus caprae* |
|   |   | *Staphylococcus carnosus* |
|   |   | *Staphylococcus chromogenes* |
|   |   | *Staphylococcus cohnii* |
|   |   | *Staphylococcus epidermidis* |
|   |   | *Staphylococcus gallinarum* |
|   |   | *Staphylococcus haemolyticus* |
|   |   | *Staphylococcus hominis* |
|   |   | *Staphylococcus hominis* subsp. *novobiosepticus* |
|   |   | *Staphylococcus hyicus* |
|   |   | *Staphylococcus intermedius* |
|   |   | *Staphylococcus lentus* |
|   |   | *Staphylococcus lugdunensis* |
|   |   | *Staphylococcus muscae* |
|   |   | *Staphylococcus pasteuri* |
|   |   | *Staphylococcus pettenkoferi* |
|   |   | *Staphylococcus pseudintermedius* |
|   |   | *Staphylococcus saccharolyticus* |
|   |   | *Staphylococcus saprophyticus* |
|   |   | *Staphylococcus schleiferi* |
|   |   | *Staphylococcus sciuri* |

TABLE 1-continued

Analytes Detected by the BCID-GP Panel

| Calls | Reported Target | Targets Detected |
|---|---|---|
|  |  | *Staphylococcus simulans* |
|  |  | *Staphylococcus vitulinus* |
|  |  | *Staphylococcus warneri* |
|  |  | *Staphylococcus xylosus* |
| 21 | mecA | *Staphylococcus aureus* (mecA) |
|  |  | *Staphylococcus epidermidis* (mecA) |
| 22 | mecC | *Staphylococcus aureus* (mecC) |
|  |  | *Staphylococcus epidermidis* (mecC) |
| 23 | vanA | *Enterococcus faecalis* (vanA) |
|  |  | *Enterococcus faecium* (vanA) |
| 24 | vanB | *Enterococcus faecalis* (vanB) |
|  |  | *Enterococcus faecium* (vanB) |
| 25 | PanCandida | *Candida albicans* |
|  |  | *Candida glabrata* |
|  |  | *Candida krusei* |
|  |  | *Candida parapsilosis* |
| 26 | Pan Gram-Negative | Enterobacteriaceae |
|  |  | *Acinetobacter* |
|  |  | *Pseudomonas* |
|  |  | *Bacteroides* |
|  |  | *Stenotrophomonas* |

^identified in the species or group call

In a preferred embodiment the Pan Gram-negative target in the BCID-GP panel can identify about 10 species of gram-negative bacteria. In a preferred embodiment the Pan Gram-negative target in the BCID-GP panel can identify at least 5, at least 10, at least 15, at least 20, at least 30, at least 40 at least 50 at least 60, at least 70, at least 80, at least 90, at least 100 or more species of gram-negative bacteria. In a preferred embodiment the Pan Gram-negative target in the BCID-GP panel can identify 30-100 species of gram-negative bacteria. In a preferred embodiment the Pan Gram-negative target in the BCID-GP panel can identify about 10%, about 20%, about 30%, about 40%, about 50%, about 60%, about 70%, about 80% or more species of gram-negative bacteria.

The BCID-GP oligonucleotides capable of binding a sequence of a bacterial pathogen which enable discrimination between gram-positive species or genus were not designed to avoid or reduce detection of background contamination. It was a surprising and unexpected result that reducing cycling from 40 to 37, and in some cases from 40 to 35, and in some cases from 40 to 30 was sufficient to distinguish between background contamination, gram-positive bacteria species or genus infection, non-species gram-negative bacteria and non-species fungal infection.

The BCID-GP assay can be further understood by the following numbered paragraphs:

Paragraph 1. An in vitro method for the detection and/or identification of a first human pathogen and/or genetic material thereof comprising subjecting a sample to a single multiplex polymerase chain reaction (PCR), wherein said method comprises amplification of PCR products under conditions appropriate for the substantial reduction or elimination in electrochemical detection of contaminating pathogen and/or genetic material present in the sample.

Paragraph 2. The method of Paragraph 1, wherein the first human pathogen comprises a gram-positive bacteria or a plurality of gram-positive bacteria.

Paragraph 3. The method of Paragraph 2, wherein the gram-positive bacteria is selected from the group consisting of *Bacillus cereus* group, *Staphylococcus epidermidis*, *Bacillus subtilis* group, *Staphylococcus lugdunensis*, *Corynebacterium* spp., *Streptococcus*, *Enterococcus*, *Streptococcus agalactiae*, *Enterococcus faecalis*, *Streptococcus anginosus* group, *Enterococcus faecium*, *Streptococcus pneumonia*, *Lactobacillus*, *Streptococcus pyogenes*, *Listeria* and combinations thereof.

Paragraph 4. The method of Paragraph 2, wherein the gram-positive bacteria is *Streptococcus*, *Staphylococcus* or *Enterococcus faecalis*.

Paragraph 5. The method of any preceding paragraph, wherein the method can further detect a second human pathogen if present in the sample.

Paragraph 6. The method of Paragraph 5, wherein the second human pathogen is gram-positive bacteria, gram-negative bacteria, fungi, a plurality of gram-positive bacteria, a plurality of gram-negative bacteria, a plurality of fungi, or combinations thereof.

Paragraph 7. The method of Paragraph 6, wherein the gram-negative bacteria is selected from the group comprising *Escherichia coli*, *Pseudomonas aeruginosa*, *Proteus mirabilis* and combinations thereof.

Paragraph 8. The method of Paragraph 6, wherein the fungi are selected from the group comprising *Candida albicans*, *Candida glabrata*, *Candida krusei*, *Candida parapsilosis* and combinations thereof.

Paragraph 9. The method of any preceding paragraph, wherein the method can further detect an antimicrobial resistance gene.

Paragraph 10. The method of Paragraph 9, wherein the antimicrobial resistance gene is selected from the group consisting of mecA, mecC, vanA, and vanB.

Paragraph 11. The method of Paragraph 6, wherein the species of the gram-negative bacterial pathogen can be identified by subjecting the sample to a second single multiplex PCR, wherein said method comprises amplification of PCR products under conditions appropriate for the substantial reduction or elimination in electrochemical detection of contaminating pathogen and/or genetic material present in the sample and wherein the gram-negative bacteria is selected from the group consisting of *Acinetobacter baumannii*, *Klebsiella pneumoniae*, *Bacteroides fragilis*, *Morganella morganii*, *Citrobacter*, *Neisseria meningitides*, *Cronobacter sakazakii*, *Proteus*, *Enterobacter cloacae* complex, *Proteus mirabilis*, *Enterobacter* (non-*cloacae* complex), *Pseudomonas aeruginosa*, *Escherichia coli*, *Salmonella*, *Fusobacterium necrophorum*, *Serratia*, *Fusobacterium nucleatum*, *Serratia marcescens*, *Haemophilus influenza*, *Stenotrophomonas maltophilia*, *Klebsiella oxytoca* and combinations thereof.

Paragraph 12. The method of Paragraph 6, wherein the species of fungi pathogen can be identified by subjecting the sample to a second single multiplex PCR, wherein said method comprises amplification of PCR products under conditions appropriate for the substantial reduction or elimination in electrochemical detection of contaminating pathogen and/or genetic material present in the sample and wherein the fungi are selected from the group consisting of *Candida albicans*, *Candida dubliniensis*, *Candida famata*, *Candida glabrata*, *Candida guilliermondii*, *Candida kefyr*, *Candida lusitaniae*, *Candida krusei*, *Candida parapsilosis*, *Candida tropicalis*, *Cryptococcus gattii*, *Cryptococcus neoformans*, *Fusarium*, *Malassezia furfur*, *Rhodotorula*, *Trichosporon* and combinations thereof.

Paragraph 13. The method of any preceding paragraph, wherein the detection method is electrochemical detection.

Paragraph 14. The method of any preceding paragraph, wherein contaminating organisms from a blood draw are identified.

Paragraph 15. The method of paragraph 14, wherein the contaminating organisms are selected from the group comprising *Propionibacterium acnes, Staphylococcus epidermidis, Micrococcus, Lactobacillus* or *Corynebacterium.*

Paragraph 16. An in vitro method for the detection and/or identification of a human pathogen and/or genetic material thereof comprising subjecting a sample to a single multiplex polymerase chain reaction (PCR), wherein said method comprises amplification of PCR products under conditions appropriate for the substantial reduction or elimination in electrochemical detection of contaminating pathogen and/or genetic material present in the sample wherein the human pathogen is gram-positive bacteria, gram-negative bacteria, fungi or combinations thereof.

Paragraph 17. A microfluidic device for the detection and/or identification of a human pathogen and/or genetic material thereof comprising: a mixture of oligonucleotides and reagents for carrying out a single nucleic acid amplification reaction capable of distinguishing between clinically relevant amplification and amplification from other sources such as from background contamination.

Paragraph 18. The microfluidic device of paragraph 17, wherein the clinically relevant amplification is a first human pathogen.

Paragraph 19. The microfluidic device of paragraph 18, wherein the first human pathogen comprises a gram-positive bacteria or a plurality of gram-positive bacteria.

Paragraph 20. The microfluidic device of Paragraph 19, wherein the gram-positive bacteria is selected from the group consisting of *Bacillus cereus* group, *Staphylococcus epidermidis, Bacillus subtilis* group, *Staphylococcus lugdunensis, Corynebacterium* spp., *Streptococcus, Enterococcus, Streptococcus agalactiae, Enterococcus faecalis, Streptococcus anginosus* group, *Enterococcus faecium, Streptococcus pneumonia, Lactobacillus, Streptococcus pyogenes, Listeria* and combinations thereof.

Paragraph 21. The microfluidic device of any preceding Paragraph, wherein the method can further detect a second human pathogen if present in the sample.

Paragraph 22. The microfluidic device of Paragraph 21, wherein the second human pathogen is gram-positive bacteria, gram-negative bacteria, fungi, a plurality of gram-negative bacteria, a plurality of fungi, or combinations thereof.

Paragraph 23. The microfluidic device of Paragraph 22, wherein the gram-negative bacteria is selected from the group comprising *Escherichia coli, Pseudomonas aeruginosa, Proteus mirabilis* and combinations thereof.

Paragraph 24. The microfluidic device of Paragraph 22, wherein the fungi are selected from the group comprising *Candida albicans, Candida glabrata, Candida krusei, Candida parapsilosis* and combinations thereof.

Paragraph 25. The microfluidic device of any preceding Paragraph, wherein the method can further detect an antimicrobial resistance gene.

Paragraph 24. The microfluidic device of Paragraph 23, wherein the antimicrobial resistance gene is selected from the group consisting of mecA, mecC, vanA, and vanB.

Paragraph 25. The microfluidic device of any preceding paragraph, wherein contaminating organisms from a blood draw are identified.

Paragraph 26. The microfluidic device of paragraph 25, wherein the contaminating organisms are selected from the group comprising *Propionibacterium acnes, Staphylococcus epidermidis, Micrococcus, Lactobacillus* or *Corynebacterium.*

Paragraph 27. The microfluidic device of Paragraph 22, wherein the species of the gram-negative bacterial pathogen can be identified by subjecting the sample to a single multiplex PCR, wherein said method comprises amplification of PCR products under conditions appropriate for the substantial reduction or elimination in electrochemical detection of contaminating pathogen and/or genetic material present in the sample and wherein the gram-negative bacteria is selected from the group consisting of *Acinetobacter baumannii, Klebsiella pneumoniae, Bacteroides fragilis, Morganella morganii, Citrobacter, Neisseria meningitides, Cronobacter sakazakii, Proteus, Enterobacter cloacae* complex, *Proteus mirabilis, Enterobacter* (non-*cloacae* complex), *Pseudomonas aeruginosa, Escherichia coli, Salmonella, Fusobacterium necrophorum, Serratia, Fusobacterium nucleatum, Serratia marcescens, Haemophilus influenza, Stenotrophomonas maltophilia, Klebsiella oxytoca* and combinations thereof.

Paragraph 28. The microfluidic device of Paragraph 22, wherein the species of fungi pathogen can be identified by subjecting the sample to a single multiplex PCR, wherein said method comprises amplification of PCR products under conditions appropriate for the substantial reduction or elimination in electrochemical detection of contaminating pathogen and/or genetic material present in the sample and wherein the fungi are selected from the group consisting of *Candida albicans, Candida dubliniensis, Candida famata, Candida glabrata, Candida guilliermondii, Candida kefyr, Candida lusitaniae, Candida krusei, Candida parapsilosis, Candida tropicalis, Cryptococcus gattii, Cryptococcus neoformans, Fusarium, Malassezia furfur, Rhodotorula, Trichosporon* and combinations thereof.

Paragraph 29. The microfluidic device of any preceding Paragraph, wherein the detection method is electrochemical detection.

Paragraph 30. A microfluidic device for the detection and/or identification of a human pathogen and/or genetic material thereof comprising: a mixture of oligonucleotides and reagents for carrying out a single nucleic acid amplification reaction capable of distinguishing between clinically relevant amplification and amplification from other sources such as from background contamination wherein the clinically relevant amplification is from a gram-positive bacteria, gram-negative bacteria, fungi or combinations thereof.

Gram-Negative

The BCID-GN Panel is a fully automated, qualitative, nucleic acid, multiplex in vitro diagnostic test for simultaneous detection and identification of multiple potentially pathogenic gram-negative bacterial organisms and select determinants of antimicrobial resistance in positive blood culture. The test also detects but does not differentiate gram-positive bacteria and several pathogenic *Candida* species. The test is able to detect 21 bacterial targets and 6 resistance genes, as well as multiple *Candida* species from a single cartridge (single PCR run) and most major gram-positive organisms, also as on a single cartridge (single PCR run).

The following bacterial organisms are identified using the BCID-GN Panel: *Acinetobacter baumannii, Klebsiella pneumoniae, Bacteroides fragilis, Morganella morganii, Citrobacter, Neisseria meningitides, Cronobacter sakazakii, Proteus, Enterobacter cloacae* complex, *Proteus mirabilis, Enterobacter* (non-*cloacae* complex), *Pseudomonas aeruginosa, Escherichia coli, Salmonella, Fusobacterium necrophorum, Serratia, Fusobacterium nucleatum, Serratia marcescens, Haemophilus influenza, Stenotrophomonas maltophilia, Klebsiella oxytoca*. The following Antimicrobial Resistance Markers are identified using the BCID-GN Panel: CTX-M, NDM, IMP, OXA, KPC, VIM. The following Pan Targets are identified using the BCID-GN panel: Pan *Candida* (*Candida albicans, Candida glabrata, Candida krusei, Candida parapsilosis*) See FIG. 18; Pan Gram-Positive (*S. anginosus* group, *Enterococcus, Staphylococcus, Streptococcus, Bacillus subtilis* group, *Bacillus cereus* group, *Enterococcus faecalis*) See FIG. 18. So for the Pan-Gram-positive call in the BCID-GN panel, a co-infection is detected by its species but identified by the type, gram-positive.

Table 2 below shows that reported target call and the target species detected. Stated another way, some species are detected by the BCID-GN panel ("Targets detected" in Table 2 below) but not identified by the species in the call (report); instead, the call/report identifies the genus. Some species are detected by the BCID-GN panel ("Targets detected" in Table 2 below) and identified by the species in the call (report). Some organisms can generate both the genus and species call.

TABLE 2

Gram-Negative Analytes Detected by the BCID-GN Panel

| Reported Target | Targets Detected |
|---|---|
| *Acinetobacter baumannii* | *Acinetobacter baumannii* |
| *Bacteroides fragilis* | *Bacteroides fragilis* |
| *Citrobacter* | *Citrobacter brakii* |
| | *Citrobacter fruendii* |
| | *Citrobacter koseri* |
| | *Critrobacter youngae* |
| *Citrobacter freundii/brakii* | *Citrobacter freundii* |
| | *Citrobacter brakii* |
| *Cronobacter sakazakii* | *Cronobacter sakazakii* |
| *Enterobacter* (not *cloacae* complex) | *Enterobacter aerogenes* |
| | *Enterobacter amnigenus* |
| | *Enterobacter gergoviae*(detect with amnigenus assay) |
| *Enterobacter cloacae complex* | *Enterobacter asburiae* |
| | *Enterobacter cloacae* |
| | *Enterobacter hormaechei* |
| *Escherichia coli* | *Escherichia coli* |
| *Fusobacterium* (not necrophorum) | *Fusobacterium nucleatum* |
| | *Fusobacterium russii* |
| | *Fusobacterium varium* |
| | *Fusobacterium periodonticum* |
| *Fusobacterium necrophorum* | *Fusobacterium necrophoum* |
| *Haemophilus influenzae* | *Haemophilus influenza* |
| *Klebsiella oxytoca* | *Klebsiella oxytoca* |
| *Klebsiella pneumoniae* | *Klebsiella pneumoniae* |
| | *Klebsiella variicola* |
| *Morganella morganii* | *Morganella morganii* |
| *Neisseria meningitidis* | *Neisseria meningitidis* |
| *Pantoea agglomerans* | *Pantoea agglomerans* |
| *Prevotella* | *Prevotella bivia* |
| | *Prevotella buccae* |
| | *Prevotella buccalis* |
| | *Prevotella corporis* |
| | *Prevotella dentalis* |
| | *Prevotella denticola* |
| | *Prevotella disiens* |
| | *Prevotella intermedia* |
| | *Prevotella oralis* |
| | *Prevotella oris* |
| | *Prevotella veroralis* |
| *Proteus* | *Proteus hauseri* |
| | *Proteus mirabilis* |
| | *Proteus penneri* |
| | *Proteus vulgaris* |
| *Proteus mirabilis* | *Proteus mirabilis* |
| *Pseudomonas aeruginosa* | *Pseudomonas aeruginosa* |
| *Pseudomonas* | *Pseudomonas aeruginosa* |
| | *Pseudomonas oryzihabitans* |
| | *Pseudomonas akaligenes* |
| | *Pseudomonas fluorescens* |

TABLE 2-continued

Gram-Negative Analytes Detected by the BCID-GN Panel

| Reported Target | Targets Detected |
|---|---|
| | *Pseudomonas mendocina* |
| | *Pseudomonas pseudoalcaligenes* |
| | *Pseudomonas putida* |
| | *Pseudomonas stutzeri* |
| *Salmonella* | *Salmonella bongori* |
| | *Salmonella bongori* |
| | *Salmonella enterica* subsp *arizonae* |
| | *Salmonella enterica* subsp *diarizonae* |
| | *Salmonella enterica* subsp *enterica* serovar *Abaetetuba* |
| | *Salmonella enterica* subsp *enterica* serovar *Abony* |
| | *Salmonella enterica* subsp *enterica* serovar *Typhimurium* |
| *Serratia mareeseens* | *Serratia marcescens* |
| *Serratia* | *Serratia ficarta* |
| | *Serratia fonticola* |
| | *Serratia grimesii* |
| | *Serratia liquefaciens* |
| | *Serratia plymuthica* |
| | *Serratia rubidaea* |
| | *Serretia odorifera* |
| *Stenotrophomonas maltophilia* | *Stenotrophomonas maltophilia* |
| CTX-M | CTX-1 |
| | CTX-2 |
| | CTX-8 |
| | CTX-9 |
| | CTX-25 |
| IMP | IMP-1 |
| | IMP-18 |
| | IMP-33 |
| | IMP-5 |
| KPC | KPC |
| NDM | NDM |
| OXA | OXA-23 |
| | OXA-48 |
| VIM | VIM |

In a preferred embodiment the Pan Gram-positive target in the BCID-GN panel can identify about 15 species of gram-positive bacteria. In a preferred embodiment the Pan Gram-positive target in the BCID-GN panel can identify at least 10, at least 15, at least 20, at least 30, at least 40 at least 50 at least 60, at least 70, at least 80, at least 90, at least 100 or more species of gram-positive bacteria. In a preferred embodiment the Pan Gram-positive target in the BCID-GN panel can identify 30-100 species of gram-positive bacteria. In a preferred embodiment the Pan Gram-positive target in the BCID-GN panel can identify about 10%, about 20%, about 30%, about 40%, about 50%, about 60%, about 70%, about 80% or more species of gram-positive bacteria.

The BCID-GN oligonucleotides capable of binding a sequence of a bacterial pathogen which enable discrimination between gram-negative species or genus were not designed to avoid or reduce detection of background contamination. It was a surprising and unexpected result that detuning the assay i.e., by merely reducing the PCR cycling, was sufficient to distinguish between background contamination, gram-negative bacteria species or genus infection, non-species gram-positive bacteria and non-species fungal infection.

The BCID-GN Panel contains targets designed to detect a broad range of organisms with a potentially misleading Gram stain result or organisms that may be missed by Gram staining altogether for example in the case of co-infections. These include a Pan Gram-Positive assay as well as a Pan *Candida* assay, both of which may provide data to facilitate the correct testing algorithm. As such, the present disclosure relates to methods and systems for a) distinguishing between background contamination and gram-negative bacterial infection; b) distinguishing between gram-negative bacterial species infection; c) distinguishing between some gram-negative bacterial species and some gram-negative genus infection(s); and d) detecting but not identifying gram-positive bacterial species or genus infection and fungal species infection. The present disclosure further relates to methods and systems for identifying a pathogen that is likely a contamination from the blood draw.

Gram-negative bacteria are a common cause of bacteremia, being isolated from over 60% of positive blood cultures throughout the world. Antimicrobial resistance is common among gram-negative organisms, and multi-drug resistance is increasingly common in many species. When involved in bacteremia, the species belonging to this group have mortality rates ranging from 20% to over 90% in some populations.

The BCID-GN assay can be further understood by the following numbered paragraphs:

Paragraph 1. An in vitro method for the detection and/or identification of a first human gram-negative bacteria pathogen and/or genetic material thereof comprising subjecting a sample to a single multiplex polymerase chain reaction (PCR), wherein said method comprises amplification of PCR products under conditions appropriate for the substantial reduction or elimination in electrochemical detection of contaminating pathogen and/or genetic material present in the sample.

Paragraph 2. The method of Paragraph 1, wherein the first human pathogen comprises a gram-negative bacteria or a plurality of gram-negative bacteria.

Paragraph 3. The method of Paragraph 2, wherein the gram-negative bacteria is selected from the group consisting of *Acinetobacter baumannii, Klebsiella pneumoniae, Bacteroides fragilis, Morganella morganii, Citrobacter, Neisseria meningitides, Cronobacter sakazakii, Proteus, Enterobacter cloacae* complex, *Proteus mirabilis, Enterobacter* (non-*cloacae* complex), *Pseudomonas aeruginosa, Escherichia coli, Salmonella, Fusobacterium necrophorum, Serratia, Fusobacterium nucleatum, Serratia marcescens, Haemophilus influenza, Stenotrophomonas maltophilia, Klebsiella oxytoca* and combinations thereof.

Paragraph 4. The method of any preceding paragraph, wherein the method can further detect a second human pathogen if present in the sample.

Paragraph 5. The method of Paragraph 4, wherein the second human pathogen is gram-negative bacteria, gram-positive bacteria, fungi, a plurality of gram-negative bacteria, a plurality of gram-positive bacteria, a plurality of fungi, or combinations thereof.

Paragraph 6. The method of Paragraph 5, wherein the gram-positive bacteria is selected from the group comprising *Staphylococcus, Streptococcus, Bacillus subtilis* group, *Bacillus cereus* group *Enterococcus, Proteus mirabilis, Acinetobater baumannii, Serratia, Citrobacter, Enterococcus faecalis, Neisseria meningitides, Morganella morganii, Klebsiella penumoniae, Haemophilus* influenza or combinations thereof.

Paragraph 7. The method of Paragraph 5, wherein the fungi are selected from the group comprising *Candida albicans, Candida glabrata, Candida krusei, Candida parapsilosi* or combinations thereof.

Paragraph 8. The method of any preceding paragraph, wherein the method can further detect an antimicrobial resistance gene.

Paragraph 9. The method of Paragraph 8, wherein the antimicrobial resistance gene is selected from the group consisting of CTX-M, NDM, IMPDXA, KPC, VIM or combinations thereof.

Paragraph 10. The method of Paragraph 5, wherein the species of the gram-positive bacterial pathogen can be identified by subjecting the sample to a single multiplex PCR, wherein said method comprises amplification of PCR products under conditions appropriate for the substantial reduction or elimination in electrochemical detection of contaminating pathogen and/or genetic material present in the sample and wherein the gram-positive bacteria is selected from the group consisting of *Bacillus cereus* group, *Staphylococcus epidermidis, Bacillus subtilis* group, *Staphylococcus lugdunensis, Corynebacterium* spp., *Streptococcus, Enterococcus, Streptococcus agalactiae, Enterococcus faecalis, Streptococcus anginosus* group, *Enterococcus faecium, Streptococcus pneumonia, Lactobacillus, Streptococcus pyogenes, Listeria*, and combinations thereof.

Paragraph 11. The method of Paragraph 5, wherein the species of fungi pathogen can be identified by subjecting the sample to a single multiplex PCR, wherein said method comprises amplification of PCR products under conditions appropriate for the substantial reduction or elimination in electrochemical detection of contaminating pathogen and/or genetic material present in the sample and wherein the fungi are selected from the group consisting of *Candida albicans, Candida dubliniensis, Candida famata, Candida glabrata, Candida guilliermondii, Candida kefyr, Candida lusitaniae, Candida krusei, Candida parapsilosis, Candida tropicalis, Cryptococcus gattii, Cryptococcus neoformans, Fusarium, Malassezia furfur, Rhodotorula, Trichosporon* and combinations thereof.

Paragraph 12. The method of any preceding paragraph, wherein the detection method is electrochemical detection.

Paragraph 13. The method of any preceding paragraph, wherein if four or more human pathogens are detected, the sample is subject to a new single PCR run.

Paragraph 14. A microfluidic device for the detection and/or identification of a human pathogen and/or genetic material thereof comprising: a mixture of oligonucleotides and reagents for carrying out a single nucleic acid amplification reaction capable of distinguishing between clinically relevant amplification and amplification from other sources such as from background contamination.

Paragraph 15. The microfluidic device of paragraph 14, wherein the clinically relevant amplification is a first human pathogen.

Paragraph 16. The microfluidic device of paragraph 15, wherein the first human pathogen comprises a gram-negative bacteria or a plurality of gram-negative bacteria.

Paragraph 17. The microfluidic device of Paragraph 16, wherein the gram-negative bacteria is selected from the group consisting of *Acinetobacter baumannii, Klebsiella pneumoniae, Bacteroides fragilis, Morganella morganii, Citrobacter, Neisseria meningitides, Cronobacter sakazakii, Proteus, Enterobacter cloacae* complex, *Proteus mirabilis, Enterobacter* (non-*cloacae* complex), *Pseudomonas aeruginosa, Escherichia coli, Salmonella, Fusobacterium necrophorum, Serratia, Fusobacterium nucleatum, Serratia marcescens, Haemophilus influenza, Stenotrophomonas maltophilia, Klebsiella oxytoca* and combinations thereof.

Paragraph 18. The microfluidic device of Paragraph 16, wherein the gram-negative bacteria is selected from the group consisting of *Escherichia coli, Pseudomonas aeruginosa, Proteus mirabilis, Proteus*, and combinations thereof.

Paragraph 19. The microfluidic device of any preceding paragraph, wherein the device can further detect a second human pathogen if present in the sample.

Paragraph 20. The microfluidic device of paragraph 18, wherein the second human pathogen is gram-negative bacteria, gram-positive bacteria, fungi, a plurality of gram-negative bacteria, a plurality of gram-positive bacteria, a plurality of fungi, or combinations thereof.

Paragraph 21. The microfluidic device of Paragraph 19, wherein the gram-positive bacteria is selected from the group comprising *Bacillus cereus* group, *Staphylococcus epidermidis*, *Bacillus subtilis* group, *Staphylococcus lugdunensis*, *Corynebacterium* spp., *Streptococcus*, *Enterococcus*, *Streptococcus agalactiae*, *Enterococcus faecalis*, *Streptococcus anginosus* group, *Enterococcus faecium*, *Streptococcus pneumonia*, *Lactobacillus*, *Streptococcus pyogenes*, *Listeria*, and combinations thereof.

Paragraph 22. The microfluidic device of Paragraph 19, wherein the fungi is selected from the group comprising *Candida albicans*, *Candida dubliniensis*, *Candida famata*, *Candida glabrata*, *Candida guilliermondii*, *Candida kefyr*, *Candida lusitaniae*, *Candida krusei*, *Candida parapsilosis*, *Candida tropicalis*, *Cryptococcus gattii*, *Cryptococcus neoformans*, *Fusarium*, *Malassezia furfur*, *Rhodotorula*, *Trichosporon* and combinations thereof.

Paragraph 23. The microfluidic device of any preceding paragraph, wherein the method can further detect an antimicrobial resistance gene.

Paragraph 24. The microfluidic device of paragraph 23, wherein the antimicrobial resistance gene is selected from the group consisting of CTX-M, NDM, IMPDXA, KPC, VIM or combinations thereof.

Paragraph 25. The microfluidic device of any preceding paragraph, wherein the detection method is electrochemical detection.

Fungal

The Blood Culture Identification Fungal Pathogen Panel (BCID-FP Panel) is a fully automated, qualitative, nucleic acid, multiplex in vitro diagnostic test for simultaneous detection and identification of multiple potentially pathogenic fungal organisms in positive blood culture. The BCID-FP Panel is performed directly on blood culture samples identified as positive by a continuously monitoring blood culture system that demonstrates the presence of organisms as confirmed by Gram stain.

The following fungal organisms are identified using the BCID-FP Panel: *Candida auris, Candida albicans, Candida dubliniensis, Candida famata, Candida glabrata, Candida guilliermondii, Candida kefyr, Candida lusitaniae, Candida krusei, Candida parapsilosis, Candida tropicalis, Cryptococcus gattii, Cryptococcus neoformans, Fusarium, Malassezia furfur, Rhodotorula,* and *Trichosporon*. The fungal species detected by the BCID-FP Panel are in FIG. 21. Specifically, *Schizosaccharomyces pombe, Malaessezia furfur, Candida albicans,* and *Candida auris* get a species call. For the *Fusarium* call, the BCID-FP panel detects but does not identify the following species in the call (report): *solani* set, *dimerum, proliferatum, moniliforme, verticillioides, oxysporum,* and *sacchari*. For the *Rhodotorula* call, the BCID-FP panel detects but does not identify the following species in the call (report): *mucilaginosa,* and *glutinis*. For the *Trichosporon* call, the BCID-FP panel detects but does not identify the following species in the call (report): asteroid, coremiiforme and dermatis.

The BCID-FP oligonucleotides capable of binding a sequence of a fungal pathogen which enable discrimination between fungal species or genus were not designed to avoid or reduce detection of background contamination. It was a surprising and unexpected result that merely creating primer mismatches and in some cases using dual zone detection was sufficient to distinguish between background contamination and fungal species or genus infection. It was non-obvious to intentionally decrease the sensitivity of the assay by intentionally introducing primer miss-matches.

The present disclosure relates to methods and systems for a) distinguishing between background contamination and fungal infection. The present disclosure relates to methods and systems for a) distinguishing between background contamination, and detecting and identifying the species or genus of fungal infection.

Invasive fungal infections are an increasingly common cause of sepsis in critically ill patients and are the source of significant morbidity and mortality. Of the fungi with the ability to cause severe sepsis, *Candida* species are by far the most prevalent, accounting for between 8-10% of all bloodstream infections in the US and 2-3% in Europe. Sepsis caused by invasive fungi is associated with mortality rates ranging from 15% to nearly 100% depending on the organism and underlying factors involved.

With increasing numbers of immunocompromised persons and increased use of implanted medical devices such as central venous catheters, the opportunity for infection with opportunistic pathogens is steadily increasing. This in combination with the fact that many fungi are part of the normal human skin, vaginal, and gastrointestinal flora and are commonly found in the environment has resulted in a significant increase in fungal involvement in bloodstream infections.

The fungal primers, signal and capture probe sequences are below. Nucleotide sequences should have at least 80% sequence identity preferably more than 85%, preferably more than 90%, preferably more than 95% sequence identity, to the sequences provided herein.

TABLE 3

Fungal Forward And Reverse Primers and Sequences ID Nos.

| Species | Forward Sequence | Reverse Sequence |
|---|---|---|
| *Rhodotorula* 1 | SEQ. ID No. 1.<br>XACTAGCACTACACGAGCACGGAAG | SEQ. ID No. 5.<br>GGTAGTTCGGAGCGTGGAATACCA |
| *Rhodotorula* 2 | SEQ. ID No. 2.<br>XAGCACGGAAGTAGTAACCCATTAG | SEQ. ID No. 6.<br>GGTCGTTTGGTACGTAGAATACCA |
| *Trichosporon* 1 | SEQ. ID No. 3.<br>ACTCTACACCGATTCTTCTAACTTCA | SEQ. ID No. 7.<br>XATGTAATATGGATGCATTGGAACTCG |

TABLE 3-continued

Fungal Forward And Reverse Primers and Sequences ID Nos.

| Species | Forward Sequence | Reverse Sequence |
|---|---|---|
| Trichosporon 2 | SEQ. ID No. 4. ACACTTCACCGATTCTTCTAACTTCA | SEQ. ID No. 8. XATGTAATATGGATGCATTGGCACTCG |
| Trichosporon 3 | | SEQ. ID No. 9. XATATAATAAGGATGCATTGGAATTCG |

The BCID-FP assay can be further understood by the following numbered paragraphs:

Paragraph 1. An in vitro method for the detection and/or identification of a first human fungal pathogen and/or genetic material thereof comprising subjecting a sample to a single multiplex polymerase chain reaction (PCR), wherein said method comprises amplification of PCR products under conditions appropriate for the substantial reduction or elimination in electrochemical detection of contaminating pathogen and/or genetic material present in the sample.

Paragraph 2. The method of Paragraph 1, wherein the fungal pathogen is selected from the group consisting of Candida auris, Candida albicans, Candida dubliniensis, Candida famata, Candida glabrata, Candida guilliermondii, Candida kefyr, Candida lusitaniae, Candida krusei, Candida parapsilosis, Candida tropicalis, Cryptococcus gattii, Cryptococcus neoformans, Fusarium, Malassezia furfur, Rhodotorula, Trichosporon and combinations thereof.

Paragraph 4. A microfluidic device for the detection and/or identification of a human fungal pathogen and/or genetic material thereof comprising: a mixture of oligonucleotides and reagents for carrying out a single nucleic acid amplification reaction capable of distinguishing between clinically relevant fungal amplification and amplification from other sources such as from background contamination.

Paragraph 5. The microfluidic device of Paragraph 4, wherein the fugal pathogen is selected from the group consisting of Candida auris, Candida albicans, Candida dubliniensis, Candida famata, Candida glabrata, Candida guilliermondii, Candida kefyr, Candida lusitaniae, Candida krusei, Candida parapsilosis, Candida tropicalis, Cryptococcus gattii, Cryptococcus neoformans, Fusarium, Malassezia furfur, Rhodotorula, Trichosporon and combinations thereof.

Paragraph 6. The microfluidic device of Paragraph 4, wherein the fugal pathogen is selected from the group consisting of Candida auris, C. parapsilosis, C. tropicalis, Rhodotorula, Trichosporon and combinations thereof.

Paragraph 7. The microfluidic device of any preceding Paragraph, wherein the detection method is electrochemical detection.

Two-Step Species Detection for Co-Infections

If a co-infection is of the same type as the infection (i.e., both gram-positive, both gram-negative or both fungal), the method and system can identify the species of the co-infection based on the first single PCR run. If a co-infection is of a different type as the infection (i.e., the infection is gram-positive but a pan gram-negative and/or pan fungal co-infection is detected or the infection is gram-negative but a pan gram-positive and/or pan fungal co-infection is detected), the method and system can identify the genus of the fungal infection and the type of the co-infection (gram-positive or negative) based on a second single PCR run.

Gram staining is typically accurate, however, some organisms are known to be gram variable, potentially producing misleading Gram stain results. Additionally, inaccurate Gram stains have also been noted in the instance of polymicrobial infections. The BCID-GP Panel includes two pan targets (Pan gram-negative and Pan Candida) designed to detect but not identify organisms that may be missed by Gram stain. Likewise, the BCID-GN Panel includes two pan targets (Pan gram-positive and Pan Candida) designed to detect but not identify organisms that may be missed by Gram stain. If a pan target is identified in the BCID-GP Panel, then the BCID-GN and/or FN Panel can be run to identify the specific species or genus of the infection. Likewise, if a pan target is identified in the BCID-GN Panel, then the BCID-GP and/or FN Panel can be run to identify the specific species or genus of the infection.

In one embodiment, the method of the invention comprises the following steps: a) identify a first species or genus infection and a co-infection; b) identifying the species of the co-infection. In one embodiment, the first infection is a gram-positive infection and the co-infection is a gram-negative infection or fungal infection. In one embodiment, the first infection is a gram-negative infection and the co-infection is a gram-positive or fungal infection.

In one embodiment, the method of the invention comprises the following steps: a) providing a sample, b) bringing said sample into contact with a mixture of oligonucleotides and reagents for carrying out a nucleic acid amplification reaction, c) after DNA/neucleic acid extraction carrying out a first single nucleic acid amplification reaction, d) obtaining a first result e) if four or more infections are present, obtaining a second result wherein obtaining a second result comprises f) providing the sample, g) bringing said sample into contact with a mixture of oligonucleotides the same as the oligonucleotides used to obtained the first result and reagents for carrying out a nucleic acid amplification reaction, h) after DNA/neucleic acid extraction carrying out a second single nucleic acid amplification reaction, and i) obtaining a second result.

In one embodiment, the method of the invention comprises the following steps: a) obtaining a first result b) analyzing the first result for a secondary infection c) if a secondary infection is present obtaining a second result wherein obtaining a second result comprises a) providing a sample, b) bringing said sample into contact with a mixture of oligonucleotides different from oligonucleotides used to obtained the first result and reagents for carrying out a nucleic acid amplification reaction, c) carrying out a single nucleic acid amplification reaction, and d) obtaining a second result.

In one embodiment, the method of the invention comprises the following steps: a) obtaining a gram-stain result (b) selecting a panel based on the gram stain result c) carry out a first single nucleic acid amplification reaction d)

detecting the amplification products generated as a result of said first single nucleic acid amplification reaction d) if the amplification products do not match the gram stain result, select a second panel based on the results from the first single nucleic acid amplification reaction e) carry out a second single nucleic acid amplification reaction d) detect the amplification products generated as a result of said second single nucleic acid amplification reaction.

In embodiments, the second single nucleic acid amplification reaction provides more specific species or genus identification than the first single nucleic acid amplification reaction for the co-infection.

A method for identifying a fungal infection not identified by a gram stain comprising loading a sample suspected of having a bacterial infection based on a gram stain into a first cartridge, amplifying the sample using a single nucleic acid amplification reaction, identifying a pan-*candida* organism, and loading the sample into a second cartridge amplifying the sample using a second single nucleic acid amplification reaction and detecting the amplification products generated as a result of said second single nucleic acid amplification reaction.

A method for screening a patient suspected of having a bacterial infection comprising a) performing a first test for the presence of a gram-positive bacterial infection; b) if the first test indicates a gram-negative bacterial infection is present performing a second test for the presence of a gram-negative bacterial infection wherein the first test and second test comprise amplifying the sample using a single nucleic acid amplification reaction.

A method for screening a patient suspected of having a fungal infection comprising a) performing a first test for the presence of a bacterial infection; b) if the first test indicates a fungal infection is present performing a second test for the presence of a fungal infection wherein the first test and second test comprise amplifying the sample using a single nucleic acid amplification reaction.

A method for identifying a plurality of organisms in a sample, comprising providing a first portion of a sample from a patient to a first cartridge, bringing said first sample into contact with a mixture of oligonucleotides and reagents for carrying out a single nucleic acid amplification reaction, determining if a second pathogen is present in said first sample, providing a second portion of a sample from the patient to a second cartridge, b) bringing said sample into contact with a mixture of oligonucleotides and reagents for carrying out a second single nucleic acid amplification reaction, determining if a second pathogen is present in said second sample.

The method of determining the existence of and identifying any one of up to a plurality of human pathogens in a sample, comprising the steps of: a) after DNA/neucleic acid extraction, performing a first detection process comprising carrying out a single nucleic acid amplification reaction, b) detecting and evaluating the amplification products generated as a result of said first single nucleic acid amplification reaction, c) after DNA/neucleic acid extraction, performing a second detection process comprising carrying out a single nucleic acid amplification reaction, and d) detecting and evaluating the amplification products generated as a result of said second detection process, thereby identifying any one of up to a plurality of human pathogens in the sample.

Amplification of Target Analytes

The BCID-GP, GN and FP panels can be run in a cartridge comprising a bottom substrate. The bottom substrate (or printed circuit board) can contain 1, 2, 3 or more amplification pathways or pads (called the Amplification Zone). These can be used for individual PCR reactions (e.g. one droplet is moved up one path and down another, etc.) or for multiplexing (e.g. eight different droplets can be moved up and down four pathways).

As will be appreciated by those in the art, each PCR reaction can additionally be multiplexed. That is, for target specific amplification, the use of multiple primer sets in a single PCR reaction can be unwieldy, and thus the invention allows multiple reactions to achieve higher levels of multiplexing. For example, for the evaluation of 21 different target sequences (for example, in screening for fungal infections), it may be desirable to run 3 different reactions of seven primer sets; e.g. a first PCR sample droplet (e.g. the bottom pathway) picks up the first set of 7 primer pairs (e.g. "Primer Mix A"), a second droplet picks up the second set of 7 primer pairs ("Primer Mix B"), and a third droplet picks up a third set ("Primer Mix C"). In some embodiments, the primers will be completely different in each set; in others, redundancy and/or internal controls are built into the system by adding the same primer sets to different tracks. The multiplexing flexibility represents one of the key advantageous and distinguishing features of the invention. The number of multiplexes can vary easily through software without the need to modify any physical components of the system.

In general, the amplification reactions (as more fully described below) for use in the present systems use sets of primers wherein one primer of each set has a blocked end that is impervious to standard exonucleases. That is, one strand of the double stranded amplicons that are generated in the PCR reaction is removed so that the resulting single stranded DNA amplicon can hybridize to the single stranded capture probe. Thus, by running a first PCR reaction and then adding exonuclease, one strand of the double stranded amplicon is digested, leaving only the detection strand.

The use of heating zones perpendicular to the amplification pathway, as generally depicted in FIG. 15, allows the droplets to travel through the appropriate thermal zones. As shown in FIG. 15, four amplification pathways are shown with three perpendicular thermal zones (in this case, the thermal elements are off chip Peltier heaters and show desired temperatures of about 95.5 C for denaturation (typically greater than 90° C.) and about 65° C. (typically 60-70° C.) for annealing and extension. In this configuration, two-step amplification cycles can be performed with more than one droplet in each PCR track, sometimes referred to herein as "tandem amplification" or "bussing amplification". For example, two droplets may be positioned in each PCR track and spaced in such a way that when one droplet is in the denaturation zone, the other is in one of combined annealing and extension zones, and vice versa. By shuttling the droplets in tandem back and forth between the denaturation and annealing/extension zones, one can amplify both of them in the same amount of time it would normally take to amplify a single droplet. In a four-track PCR configuration, this means that eight droplets can be amplified simultaneously instead of four.

Detection of Amplification Products

The BCID-GP, GN and FP panels can be run on an automated nucleic acid testing system including extraction, amplification, and detection, combining electrowetting and electrochemical detection. Electrochemical detection technology is based on the principles of competitive DNA hybridization and electrochemical detection, which is highly specific and is not based on fluorescent or optical detection.

Electrowetting, or digital microfluidics, uses electrical fields to directly manipulate discrete droplets on the surface of a hydrophobically coated printed circuit board (PCB). Sample and reagents are moved in a programmable fashion in the cartridge to complete all portions of the sample processing from nucleic acid extraction to detection.

A sample is loaded into the cartridge and the cartridge is placed into the instrument. Nucleic acids are extracted and purified from the specimen via magnetic solid phase extraction (i.e. the use of magnetic beads to pre-concentrate analytes or targets, then move (elute) the beads containing the targets to a different location, where the targets are released for post-elution events. PCR is used to created double-stranded cDNA which is treated with exonuclease to create single-stranded DNA in preparation for electrochemical detection.

The target amplicons are mixed with ferrocene-labeled signal probes that are complementary to the specific targets on the panel. Target sequences hybridize to the complementary signal probe and capture probes, which are bound to gold-plated electrodes, as shown in FIG. 1. The presence of each target is determined by voltammetry which generates specific electrical signals from the ferrocene-labeled signal probe. Specifically, FIG. 1 shows the hybridization complex. Target-specific capture probes are bound to the gold electrodes in the microarray on the cartridge. The amplified target DNA hybridizes to the capture probe and to a complementary ferrocene-labeled signal probe. The electrochemical analysis determines the presence or absence of targets using voltammetry. The use of microfluidic systems in the electrochemical detection of target analytes is described in more detail in U.S. Pat. Nos. 9,557,295, 8,501,921, 6,600,026, 6,740,518 and U.S. application Ser. No. 14/538,506 which are herein incorporated by reference in their entirety.

Initial sample processing begins with blood draw, removal of blood from the tube at the lab, centrifugation, gram stain. Following gram stain, sample processing is summarized here: Step-1. Obtain sample after gram stain; Step 0. Load Sample; step 1. Combine Lysis Buffer with Sample (LRM), beads and Dispense Oil (Cartridge sub-assembly); step 2. Combine Binding Buffer with Sample (LRM) and Dispense Reconstitution Buffer (cartridge sub-assembly); step 3. Separate beads from sample bead mixture (LRM) and Rehydrate PCR reagent (cartridge sub-assembly); step 4. Wash beads with Wash buffer (LRM) and Rehydrate PCR reagent (cartridge sub-assembly); step 5. Flush beads from LRM into cartridge; step 6. Final bead wash in cartridge sub-assembly and Quick Rinses (cartridge sub-assembly); step 7. Elute target analyte from beads; step 8. Combine PCR reagent with elute target (analyte); step 9. Dispense analyte drops mix into PCR staging area; step 10. Rehydrate PCR primers cocktail with each analyte drop; step 11. Transfer eluted analyte to thermal-cycling PCR area in the cartridge; step 12. Convert RNA into DNA with Reverse Transcriptase (optional step); step 13. Perform PCR cycling; step 14. Rehydrate exonuclease reagent; step 15. Combine PCR products with exonuclease reagent (ssDNA conversion); step 16. Exonuclease incubation and combine with Signal Probe cocktail (detection); step 17. Deliver PCR products and signal probe into Detection area; step 18. Incubate in eSensor area with capture probe bound to gold electrode; step 19. Scan and detect target analyte; step 20. Eject cartridge.

The basic microfluidic platform used herein is based on systems developed by Advanced Liquid Logic (ALL, currently a subsidiary of Illumina, Inc.), as more fully described in U.S. Patent app. no. 20140194305 (which is incorporated by reference in its entirety). In general, these technologies rely on the formation of microdroplets and the ability to independently transport, merge, mix and/or process the droplets, using electrical control of surface tension (i.e., electrowetting). In general, liquid samples are contained within a microfluidic device between two parallel plates. One plate contains etched drive electrodes on its surface while the other plate contains either etched electrodes or a single, continuous plane electrode that is grounded or set to a reference potential ("biplanar electrowetting"). Hydrophobic insulation covers the electrodes and an electric field is generated between electrodes on opposing plates. This electric field creates a surface-tension gradient that causes a droplet overlapping the energized electrode to move towards that electrode. In some embodiments, the active electrowetting electrodes may be adjacent and on the same plane as the neighboring ground reference electrode, which is referred to as "coplanar electrowetting"). Through proper arrangement and control of the electrodes, a droplet can be transported by successively transferring it between adjacent electrodes. The patterned electrodes can be arranged in a two dimensional array so as to allow transport of a droplet to any location covered by that array. The space surrounding the droplets may be filled with a gas such as air or an immiscible fluid such as oil, with immiscible oils being preferred embodiments of the present invention. Indeed, the immiscible fluid may be a synthetic silicone oil. This silicone oil is present throughout the system, i.e., during amplification and detection.

Signal probes are used in the electrochemical detection of target analytes on the surface of a monolayer. QW56 or QW80 are ferrocene labeled signal probes that can be prepared using routine DNA synthesis techniques essentially as described in commonly owned application PCT/US08/82666 (published as WO/2009/061941A2 and U.S. Pat. No. 7,820,391 which are herein incorporated by reference in its entirety). In U.S. application Ser. No. 14/218,61 (which is herein incorporated by reference in its entirety), FIG. 3A depicts QW 56 and FIG. 3B depicts QW8U. N6 (a ferrocene labeled signal probe) is another label that can be used; its synthesis is described in commonly owned U.S. Pat. No. 7,393,645 which is herein incorporated by reference in its entirety.

Capture probes are used in the electrochemical detection of target analytes on the surface of a monolayer. Specifically, capture binding ligands (called capture probes when the target analyte is a nucleic acid) anchor target analytes to the electrode surface and form an assay complex. The assay complex further comprises an electron transfer moiety (ETM), that is directly or indirectly attached to the target analyte. That is, the presence of the ETM near the electrode surface is dependent on the presence of the target analyte. Electron transfer between the ETM and the electrode is initiated using a variety of techniques as known by those of skill in the art, and the output signals received and optionally processed as further known by those of skill in the art. Thus, by detecting electron transfer, the presence or absence of the target analyte is determined.

In general, there are two basic detection mechanisms that may be used. In a preferred embodiment, detection of an ETM is based on electron transfer through the stacked π-orbitals of double stranded nucleic acid. This basic mechanism is described in U.S. Pat. Nos. 5,591,578, 5,770,369, 5,705,348, and PCT US97/20014 and is termed "mechanism-1" herein. Briefly, previous work has shown that electron transfer can proceed rapidly through the stacked π-orbitals of double stranded nucleic acid, and significantly more slowly through single-stranded nucleic acid. Accordingly, this can serve as the basis of an assay. Thus, by adding ETMs (either covalently to one of the strands or non-covalently to the hybridization complex through the use of hybridization indicators, described below) to a nucleic acid that is attached to a detection electrode via a conductive oligomer, electron transfer between the ETM and the electrode, through the nucleic acid and conductive oligomer, may be detected.

Alternatively, the presence or absence of ETMs can be directly detected on a surface of a monolayer. That is, the electrons from the ETMs need not travel through the stacked π orbitals in order to generate a signal. As above, in this embodiment, the detection electrode preferably comprises a self-assembled monolayer (SAM) that serves to shield the electrode from redox-active species in the sample. In this embodiment, the presence of ETMs on the surface of a SAM, that has been formulated to comprise slight "defects" (sometimes referred to herein as "microconduits", "nanoconduits" or "electroconduits") can be directly detected. This basic idea is termed "mechanism-2" herein. Essentially, the electroconduits allow particular ETMs access to the surface. Without being bound by theory, it should be noted that the configuration of the electroconduit depends in part on the ETM chosen. For example, the use of relatively hydrophobic ETMs allows the use of hydrophobic electroconduit forming species, which effectively exclude hydrophilic or charged ETMs. Similarly, the use of more hydrophilic or charged species in the SAM may serve to exclude hydrophobic ETMs. Thus, in either embodiment, an assay complex is formed that contains an ETM, which is then detected using the detection electrode and the signal processing techniques outlined herein.

Moreover, as specifically described in U.S. Pat. No. 6,740,518 which is herein incorporated by reference in its entirety, monitoring of the output signal at higher harmonic frequencies can be used to acheive higher signal to noise ratios, to increase the detection limits of target analytes. For example, the ferrocene response reacts non-linearly, producing a harmonic response in the signal above that in the background; this harmonic signal from AC voltametry is most likely the result of a harmonic distortion due to the nonlinear response of the electrochemical cell; see Yap, J. of Electroanalytical Chem. 454:33 (1998); hereby incorporated by reference. Thus, any techniques that increase this non-linearity are desirable. In a preferred embodiment, techniques are used to increase the higher harmonic signals; thus, frequency and phase-sensitive lock-in detection is performed at both the fundamental frequency of the applied waveform and also at multiples of the fundamental frequency (i.e. the higher harmonics). Since the background capacitance responds relatively linearly to AC signals (a sine wave input AC voltage results in a relatively nondistorted sine wave output), very little upper harmonic current is produced in the background. This gives a dramatic increase in the signal to noise ratio. Thus, detection at the higher harmonic frequencies, particularly the third, fourth and fifth harmonics (although the harmonics from second to tenth or greater can also be used) is shown to result in dramatic suppression of the background currents associated with non-Faradaic processes (like double layer charging) that can overwhelm the signal from the target molecules. In this way, the evaluation of the system at higher harmonic frequencies and phases can lead to significant improvements in the detection limits and clarity of signal. Thus, in a preferred embodiment, one method of increasing the non-linear harmonic response is to increase or vary the amplitude of the AC perturbation, although this may also be used in monitoring the fundamental frequency as well. Thus, the amplitude may be increased at high frequencies to increase the rate of electron transfer through the system, resulting in greater sensitivity. In addition, this may be used, for example, to induce responses in slower systems such as those that do not possess optimal spacing configurations Electrode initialization is another signal processing method to achieve higher signal to noise ratios, and to increase the detection limits of target analytes. In general, in any system, the observed signal is a combination of signal from the target analyte (sample signal) and signal from the background, or noise. Electrode initialization provides variations in initiation signals (e.g. varying the "input") that can be used to increase the signal, decrease the noise, or make the signal more obvious or detectable in a background of noise. In an embodiment, the input signal is AC/DC offset. In an embodiment, the AC frequency ranges from 90-1000 Hz. In an embodiment, the AC voltage ranges from −150 to 880 mV rms. In an embodiment, electrode initialization is performed for 0.5-5 seconds and then stopped as described in U.S. patent application Ser. No. 14/218,615 which is herein incorporated by reference in its entirety.

These techniques are generally described in U.S. application Ser. No. 14/062,860 and U.S. Pat. Nos. 4,887,455; 5,591,578; 5,705,348; 5,770,365; 5,807,701; 5,824,473; 5,882,497; 6,013,170; 6,013,459; 6,033,601; 6,063,573; 6,090,933; 6,096,273; 6,180,064; 6,190,858; 6,192,351; 6,221,583; 6,232,062; 6,236,951; 6,248,229; 6,264,825; 6,265,155; 6,290,839; 6,361,958; 6,376,232; 6,431,016; 6,432,723; 6,479,240; 6,495,323; 6,518,024; 6,541,617; 6,596,483; 6,600,026; 6,602,400; 6,627,412; 6,642,046; 6,655,010; 6,686,150; 6,740,518; 6,753,143; 6,761,816; 6,824,669; 6,833,267; 6,875,619; 6,942,771; 6,951,759; 6,960,467; 6,977,151; 7,014,992; 7,018,523; 7,045,285; 7,056,669; 7,087,148; 7,090,804; 7,125,668; 7,160,678; 7,172,897; 7,267,939; 7,312,087; 7,381,525; 7,381,533; 7,384,749; 7,393,645; 7,514,228; 7,534,331; 7,560,237; 7,566,534; 7,579,145; 7,582,419; 7,595,153; 7,601,507; 7,655,129; 7,713,711; 7,759,073; 7,820,391; 7,863,035; 7,935,481; 8,012,743; 8,114,661, 9,598,722, all of which are incorporated by reference in their entirety.

The automated nucleic acid testing system aka electrochemical detection system described above includes a) an instrument bank comprising a plurality of biochip cartridge bays for insertion and analysis of a biochip cartridge, wherein each bay comprises: i) a top bay comprising actuators for a liquid reagent module (LRM); and ii) a bottom bay comprising electrical connections for an electrowetting electrode grid and detection electrodes; and b) a base station comprising: i) a central processing unit; and ii) a user interface comprising a touch screen display having a plurality of bay icons, each icon uniquely corresponding to one of said plurality of bays. The sample-to-answer system is generally described in U.S. patent application Ser. No. 14/062,865, U.S. Pat. No. 9,598,722 and Provisional U.S. Patent Application 62/396,449 all of which are incorporated by reference in their entirety.

Identification, detection or reporting results occurs when amplified target DNA hybridizes to its complementary signal probe and capture probes. Identification, detection or reporting results occurs when amplified target DNA hybridizes to its complementary signal probe and capture probes wherein the capture probe is bound to gold-plated electrodes. Identification, detection or reporting results occurs when a hybridization complex forms between the target DNA and signal and capture probes.

Detection of a target analyte can be further understood by the following numbered paragraphs:

Paragraph 1: A method for detecting the presence of a target analyte in a sample, the method comprising: a) providing an electrode comprising a monolayer and a capture binding ligand; b) initializing the electrode; c) hybridizing a probe to said target analyte to form an assay complex; and d) detecting the presence or absence of said target analyte wherein said detection comprises the substantial reduction in detection of contaminating pathogen and/or genetic material present in the sample.

Paragraph 2: A method of determining the presence of target analytes in a sample comprising: a) applying said sample to an array comprising a plurality of electrodes, wherein at least one electrode comprises an assay complex comprising: i) a capture binding ligand covalently attached to said electrode; ii) a target analyte; and iii) an electron transfer moiety; b) applying an input waveform to said electrode to generate an output waveform comprising at least one harmonic component, having a harmonic number greater than or equal to two; c) detecting said output waveform at said electrode; d) analyzing said harmonic component with harmonic number greater than or equal to two to determine the presence of said target analytes wherein said method comprises the substantial reduction in detection of contaminating pathogen and/or genetic material present in the sample.

Paragraph 3: An immobilized capture probe carrier comprising: a first capture probe for detecting a species of pathogenic bacterium, the first capture probe being arranged on a solid phase carrier; and a second capture probe for detecting a genus of pathogenic fungi or type of pathogenic gram-positive or pathogenic gram-negative bacterium immobilized at a position spaced from the first capture probe wherein there is substantial reduction in detection of contaminating pathogen and/or genetic material present in the sample.

Paragraph 4: An signal probe carrier comprising: a first signal probe bound to a ferrocene label for detecting a species of pathogenic bacterium; and a second signal probe for detecting a genus of pathogenic fungi or type of pathogenic gram-positive or pathogenic gram-negative bacterium wherein there is substantial reduction in detection of contaminating pathogen and/or genetic material present in the sample.

Paragraph 5: An in vitro method for the detection and/or identification of a hybridization complex immobilized on a gold substrate comprising a human pathogen and/or genetic material thereof hybridized to a signal probe with a ferrocene label and a capture probe comprising: subjecting a sample comprising or suspected of comprising a human pathogen and/or genetic material thereof to a single multiplex polymerase chain reaction (PCR), wherein said method comprises amplification of PCR products under conditions appropriate for the substantial reduction in detection of contaminating pathogen and/or genetic material present in the sample.

Paragraph 6: A method for detecting the presence of a target analyte in a sample, the method comprising: a) subjecting the sample to a single multiplex polymerase chain reaction (PCR), wherein said method comprises amplification of PCR products under conditions appropriate for the substantial reduction or elimination in electrochemical detection of contaminating pathogen and/or genetic material present in the sample and amplification of a species specific sequence of a gram-positive bacterial pathogen and not gram-negative bacteria or fungi; b) providing an electrode comprising a monolayer and a capture binding ligand; c) hybridizing said amplified target analyte to said capture binding ligand to form an assay complex; and d) detecting the presence or absence of said target analyte wherein said detection comprises the substantial reduction in detection of contaminating pathogen and/or genetic material present in the sample. In some embodiments, step a can further detect a second human pathogen if present in the sample wherein the second human pathogen is gram-positive bacteria, gram-negative bacteria, or fungi. In some embodiment's species of the gram-negative bacterial pathogen or fungal pathogen can be identified by subjecting the sample to a second single multiplex PCR, wherein said method comprises amplification of PCR products under conditions appropriate for the substantial reduction or elimination in electrochemical detection of contaminating pathogen and/or genetic material present in the sample.

Paragraph 7: A method for detecting the presence of a target analyte in a sample, the method comprising: a) subjecting the sample to a single multiplex polymerase chain reaction (PCR), wherein said method comprises amplification of PCR products under conditions appropriate for the substantial reduction or elimination in electrochemical detection of contaminating pathogen and/or genetic material present in the sample and amplification of a species specific sequence of a gram-negative bacterial pathogen and not gram-positive bacteria or fungi; b) providing an electrode comprising a monolayer and a capture binding ligand; c) hybridizing said amplified target analyte to said capture binding ligand to form an assay complex; and d) detecting the presence or absence of said target analyte wherein said detection comprises the substantial reduction in detection of contaminating pathogen and/or genetic material present in the sample. In some embodiments, step a can further detect a second human pathogen if present in the sample wherein the second human pathogen is gram-positive bacteria, gram-negative bacteria, or fungi. In some embodiments, step a can further detect a second human pathogen if present in the sample by its genus or gram type. In some embodiment's species of the gram-positive bacterial pathogen or fungal pathogen can be identified by subjecting the sample to a second single multiplex PCR, wherein said method comprises amplification of PCR products under conditions appropriate for the substantial reduction or elimination in electrochemical detection of contaminating pathogen and/or genetic material present in the sample.

Paragraph 8: A microfluidic device for detecting a human pathogen and/or genetic material thereof comprising: a housing, a liquid reagent modual, a top plate and a bottom substrate the bottom substrate comprising a mixture of oligonucleotides and reagents for carrying out a single nucleic acid amplification reaction capable of distinguishing between contaminating pathogen and/or genetic material present in the sample and infectious pathogen and/or genetic material present in the sample and capable of distinguishing between gram-negative bacterial species and identifying by its genus a fungal co-infection or identifying by its type a gram-positive co-infection.

Paragraph 9: An immobilized capture probe capable of capable of distinguishing between contaminating pathogen and/or genetic material present in the sample and infectious pathogen and/or genetic material present in the sample and capable of distinguishing between gram-negative bacterial species and identifying by its genus a fungal co-infection or identifying by its type a gram-positive co-infection.

Paragraph 10: A signal probe capable of capable of distinguishing between contaminating pathogen and/or genetic material present in the sample and infectious pathogen and/or genetic material present in the sample and capable of distinguishing between gram-negative bacterial species and identifying by its genus a fungal co-infection or identifying by its type a gram-positive co-infection.

Paragraph 11: An in vitro method for the detection and/or identification of a human pathogen and/or genetic material thereof comprising subjecting a sample to a single multiplex polymerase chain reaction (PCR), wherein said method comprises amplification of PCR products under conditions appropriate for the substantial reduction or elimination in detection of contaminating pathogen and/or genetic material present in the sample wherein the human pathogen is gram-positive bacteria, gram-negative bacteria, fungi or combinations thereof wherein the PCR products are cycled 30-35 times and are moved between heaters using electrowetting.

Paragraph 12: A method of treating a patient having or suspected of having a bacterial infection comprising: obtaining a blood sample; subjecting the sample to a single multiplex polymerase chain reaction (PCR), wherein said method comprises amplification of PCR products under conditions appropriate for the substantial reduction or elimination in electrochemical detection of contaminating pathogen and/or genetic material present in the sample wherein the human pathogen is gram-positive bacteria, gram-negative bacteria, fungi or combinations thereof; detecting the presence of a clinically relevant pathogen and treating the patient based on detection.

Paragraph 13: A method of detecting a human pathogen in a sample, the method comprising: obtaining a sample; detecting whether a human pathogen is present by subjecting the sample to a single multiplex polymerase chain reaction (PCR), wherein said method comprises amplification of PCR products under conditions appropriate for the substantial reduction or elimination in electrochemical detection of contaminating pathogen and/or genetic material present in the sample wherein the human pathogen is gram-positive bacteria, gram-negative bacteria, fungi or combinations thereof.

Paragraph 14: A method of diagnosing a gram-positive bacterial infection or gram-negative bacterial infection or fingal infection in a patient, said method comprising: obtaining a blood sample; subjecting the sample to a single multiplex polymerase chain reaction (PCR), wherein said method comprises amplification of PCR products under conditions appropriate for the substantial reduction or elimination in electrochemical detection of contaminating pathogen and/or genetic material present in the sample; detecting whether a gram-positive bacteria or gram-negative bacterial infection or fingal infection is present by contacting the the PCR products with a signal and capture probe and detecting binding between the PCR products and the signal and capute probe; and diagnosing the patient with a gram-positive infection when the presence of a gram-positive bacterial identified by its species or genus is detected or diagnosing the patient with a gram-negative infection when the presence of a gram-negative bacterial identified by its species or genus is detected or diagnosing the patient with a fungal infection when the presence of a fungi is identified by its species or genus is detected.

Paragraph 14: A method of diagnosing and treating a gram-positive bacterial infection or gram-negative bacterial infection or fingal infection in a patient, said method comprising: obtaining a blood sample; subjecting the sample to a single multiplex polymerase chain reaction (PCR), wherein said method comprises amplification of PCR products under conditions appropriate for the substantial reduction or elimination in electrochemical detection of contaminating pathogen and/or genetic material present in the sample; detecting whether a gram-positive bacteria or gram-negative bacterial infection or fingal infection is present by contacting the the PCR products with a signal and capture probe and detecting binding between the PCR products and the signal and capute probe; and administering an effective amount of antibiotic or anti-fungal to the diagnosed patient.

Sample-To-Answer System

The sample-to-answer system combines an automated nucleic acid testing system with communication capabilities to streamline the diagnostic workflow from physician order entry to the release of the final report with accurate, actionable test results.

The sample-to-answer system is designed to reduce avoidable medical errors. Preventable medical errors are now the third leading cause of death in the United States at more than 250,000 per year. See Martin A Makary, Michael Daniel. *Medical error—the third leading cause of death in the US. BMJ*, 2016. Automating information transfer has been shown to be effective in reducing many common errors, including patient identity checking and result transcription. The sample-to-answer system is uniquely designed with patient safety features to help address this challenge in the lab.

Bi-Directional LIS

The sample-to-answer system includes a bi-directional LIS (also referred to as a communication system, an LIS communication system, bi-directional LIS communication system and the like) to automate and accelerate order entry and results reporting. See FIG. 2 for a schematic of the bi-directional LIS reporting. Specifically, when a sample is collected, the physician creates a test order called a physician test order. The physician test order allows the physician to specify a sample stability time (the time the sample is stable before results could be affected). The physician test order will further allow the physician to specify the time that a physician test order should remain on the physician test order list before processing.

Physician→Hospital LIS

After the physician test order is generated, the physician test order is sent to the hospital's laboratory information system (LIS), a computer software that processes, stores and manages data from all stages of medical processes and tests. The physician test order is accepted by the Hospital LIS and a pending test order (PTO) is created once the patient sample is received and accessioned by the lab into the hospital LIS.

Hospital LIS→LIS Interchange

The hospital's LIS sends the PTO to an LIS interchange which converts the PTO request from an HL7 or ASTM format to a CSV format and the PTO is now referred to as a test order or an interchange order or formatted test order and the like. HL7 and ASTM are a set of standards used in the transfer of information between clinical instruments and Laboratory Information Systems. In this way, the sample-to-answer system is able to communicate with any hospital LIS because it is driven by multiple standard messaging protocols such as HL7 and ASTM. In this way, if the hospital's LIS system is updated the LIS interchange can be remotely updated (an update on the clinical instrument is not required).

The sample-to-answer system further supports a "flat file format" i.e. non-standard file support for laboratories without automated interfaces (HL7 or ASTM). As such, tests can be imported and/or exported manually in a text format, CSV, TXT or XML formats. Automatic results can be released in XML format to a shared network location.

When the LIS interchange receives the PTO and reformats it to a test order, the test order is auto published with information associated with the PTO/sample such as patient identification, accession number, test ordered (BCID-GP, BCID-GN, BCID-FP etc), patient type (e.g. pediatric, intensive care, maternity), patient location (e.g. pediatrics, ER, maternity), and/or time stamps such as sample collection, sample ordering, time received at central receiving, central receiving sort, transport to lab and/or accession of sample. These time stamps provide real-time monitoring by the instrument software of pending test order turn-around time.

LIS interchange→Clinical Instrument's CPU

The automated nucleic acid testing system with communication capabilities is referred to as a "Clinical instrument" of sample-to-answer system. After the LIS interchange receives the test order, it sends it to the sample-to-answer system's (clinical instrument's) CPU in the base station.

The sample-to-answer system supports both serial and ethernet/RJ45 input/output connections to one or more hospital LIS.

The Sample Stability feature or Sample Stability time allows the user to specify the stability time on a per assay basis. The software tracks PTO orders and sends an alert notification when an order has violated the threshold for sample stability. The sample-to-answer system includes "cleanup rules" to automatically delete outstanding pending test orders e.g. delete a PTO if it is in the Pending Test Order queue for a predetermined time (called max PTO time), preferably for more than one week, preferably for more than two weeks.

These bi-directional LIS capabilities improve PTO to detection report turnaround time, reduce labor costs, and eliminate potential transcription errors.

The communication from the LIS interchange to the detection device's CPU can be referred to as the clinical instrument test order.

Reporting Results

Detection Reports

After the sample is run in a detection system, a result is generated. A result is generated if the amplified target DNA/neucleic acid hybridizes to its complementary signal probe and capture probes. The CPU in the base station then sends (either automatically or manually) a detection report (also referred to as a result report or test results) to the LIS interchange which converts the detection report into a physician test result report and sends the physician test result report to the hospital's LIS which then sends the physician result report to the physician or directly to the physician. The detection report/physician test result sent to the hospital's LIS or to the physician can include detected targets, non-detected targets, invalid results and/or control data. The sample-to-answer system can either auto release all information or hold all information for manual release. Alternatively, the sample-to-answer system can auto release some detection reports and hold some detection reports for manual release. For example, detected and non-detected targets can be auto-released while invalids can be manually released (i.e., released only after a lab supervisor approves for release). If the detection report shows 3 (triple infection) or fewer targets were identified/detected the detection report will automatically release to the hospital's LIS/physician. If the detection report shows greater than 3 (i.e. 4 or more) targets were identified/detected the report will be flagged, a multiple infection error alert (also called an alert notification) can be sent to the operator or physician and the sample can be automatically re-run. The detection report includes the assay ordered. If a cartridge is inserted that does not match the assay ordered (e.g. a gram-negative assay is ordered but a respiratory assay is inserted) a "mismatch alert" is sent to the operator and/or physician and/or the additional target is noted in the detection report. Anomalous results that are not auto-released can require a manager signature before manual release. Such reporting minimizes the risk of reporting errors.

The detection report can include time stamps such as sample collection time, sample ordering time, transport to central receiving time, central receiving sort time, transport to lab time, accession of sample time, time to process, and time to detection. FIG. 3 includes an "order-to-report" timeline. The clock time stamps are commonly documented in hospital and laboratory information systems.

The automated result reporting (at order entry and results reporting) eliminates transcription errors and ensures actionable results are returned to physicians as soon as possible. Sample results are reported in about 60-90 minutes after the start of running the sample, this is referred to as time to result (See FIG. 2) or sample to result. Preferably, sample results are reported in about 60 minutes after the start of running the sample. Preferably, sample results are reported in under 90 minutes after the start of running the sample. Preferably, sample results are reported upon test completion. A detection report is sent immediately after the pathogen is identified by the detection system.

The sample-to-answer system allows the operator to include comments in the detection report called detection report comments, e.g., to specify if the assay ordered matched the target detected, if the assay ordered does not match the target detected, if an additional target was detected in addition to the target for the assay ordered, if a second assay is recommended, if a resistance gene was identified, suggest a course of treatment such as antibiotic.

Control Reports

Control reports or Control summary reports are generated based on the assay, test frequency and lot of cartridges from the supplier. Control reports provide information about the number of samples run, and when control runs are needed. When a control run is processed, the report shows the expected and actual result, if the control passed or failed. Control runs are typically run every 30 days or every lot change. The sample-to-answer system alerts to the operator 48 and/or 24 hours before a control run is needed.

System Usage Report

The system usage report provides analytics around system usage data and performance based on a specified date range. For example, the system usage report will show if higher or lower than average samples were run, if higher or lower than expected samples were run, if a bay has not been utilized, etc. System Usage Reports can be printed from the Clinical Instrument or remotely by the clinical instrument's provider.

Service Notification Report

A service notification report is a report sent to the clinical instrument's provider to request remote access to the clinical instrument to trouble shoot errors such as when a device has exceeded downtime for a month, exceeded invalid runs, mean time to failure is too high, no LIS connectivity etc.

Alerts

The sample-to-answer system includes a number of automatic alerts.

A Remote Practitioner Alert is an alert sent to practitioners to notify them that test results are available.

A Non-Operator Alert is an alert sent to non-operators such as lab-managers, directors of labs etc. regarding test results.

A Reportable Organism Alert is an alert sent based on a user-defined reportable organisms. For example, if a patient is diagnosed with an infectious disease, then an alert can be sent to the Department of Health.

A Turnaround Time Violation Alert is an alert sent to the physician, operator or lab manager when the predetermined turnaround time is violated.

A Sample Stability Time Violation Alert is an alert sent to the physician, operator or lab manager that the sample stability time was violated.

A Duplicate Accession ID Alert is an alert notifying the operator that a sample with the same accession number was already run. Since each sample should have its own accession number, the operator should review for a possible error.

A Multiple Infection Error Alert is an alert to notify the operator that there are 4 or more co-infections detected and the sample should be re-run.

A Mismatch Alert is an alert sent to the operator or physician that a target is detected which does not match the assay ordered (e.g. a gram-negative assay is ordered but a fungal infection is identified). The mismatch can be the only target detected or can be in addition to a target expected to be detected by the assay ordered. When a mismatch alert is sent the sample can be automatically re-run on the assay ordered or on another assay which matches the mismatch. For example, if the assay ordered was a BCID-GP assay but a fungal target was identified, the BCID-GP assay can be re-run and/or a BCID-FP assay is run.

User Interface

The detection system includes a user interface comprising a touch screen display having a plurality of bay icons, each icon uniquely corresponding to one of said plurality of bays. The user interface further includes hour, minute and second countdown timer on the bay icon to show the time left until a result will be reported.

Additionally, the user interface will display the bay status (whether the bay is empty, the presence or absence of a cartridge, whether the cartridge assay is underway, assay complete, and a process error) even while the user is logged out.

The user interface audible clicks by default on a virtual keyboard.

The user interface allows batch printing of reports.

QC Results

Monitoring and reporting quality control is both a requirement and a best practice to ensure the accuracy of patient testing results and compliance with lab standards. With on-board QC tracking capabilities, the sample-to-answer system provides safeguards to ensure labs not only run controls when required but can easily track and report compliance. Indeed, the base station itself retains onboard QC test records to help ensure the lab runs controls when required. As discussed above, control reports are sent if an external control is due in 48 hours and/or 24 hours.

The sample-to-answer system can prevent new runs if the detection system has not been qualified. This means that if a new lot is provided and a control should be run on the clinical instrument before running a patient sample, the instrument will prevent a patient sample test until the control is run.

The Sample-to-answer system further supports the release of QC results to the hospital LIS either automatically or manually.

Further, patient data is automatically removed in all exported run data (troubleshooting logs and raw data calculations such as nA signal from targets, non-detected targets, controls etc) for HIPPA compliance.

The sample-to-answer system tracks and reports required preventative maintenance. Such systems maximize lab efficiency by reducing administrative overhead.

Compliance and Data Management

The sample-to-answer system provides the following compliance and data management tools: Integrated data analytics to easily monitor lab performance, on-demand epidemiology reports for export and simplified analysis in Excel (including disease prevalence in a geographic area); and fully configurable, auto-release of test results (detected targets as well as non-detected targets). All of these unique capabilities of the sample-to-answer system allow Lab Directors to reduce their time spent on routine administrative tasks and focus their limited resources on high-value activities that impact patient care and the bottom line.

Specifically, on demand Epidemiology reports can be run from each base station individually or collectively from all of the base stations run in the laboratory via the LIS.

Remote Service Capability

The sample-to-answer system includes remote service capability to minimize system downtime and ensure patients and physicians have access to rapid test results. Remote service may be needed when the clinical instrument has exceeded downtime for a month, exceeded invalid runs, mean time to failure is too high, no LIS connectivity etc.

Positive Patient ID

The sample-to-answer system's positive patient ID feature reduces the potential for patient sample mix-up. Positive patient ID is described in more detail in U.S. Pat. No. 9,500,663 which is herein incorporated in its entirety by reference. Specifically, two machine-readable information tags (or patient identification tags) are arranged on the cartridge and encoded with cartridge-identifying information, where the information encoded in the second tag corresponds to the information encoded in the first tag and is read by a device within the sample processing instrument.

After a first machine-readable information tag on the outside of the cartridge is scanned, the cartridge can be loaded into any bay at any time, this is referred to as "random access" or "random and continuous bay access" or "unassigned" or un-delegated" or un-allocated" or unspecified" and the like. Stated another way, the cartridge need not be loaded into a specified bay. In this way, loading errors are avoided. Once the cartridge is loaded, the bay's CPU reads a second machine-readable information tag and confirms it matches the first machine-readable information tag.

With the sample-to-answer system, labs and physicians can have confidence that they have the right patient, with the right test, and the right result every time.

The sample-to-answer system can be further understood by the following numbered paragraphs:

Paragraph 1. An in vitro method for reporting test results to a hospital LIS comprising: obtaining a test order from a hospital's laboratory information system (LIS); conveying the test order to a sample-to-answer system; receiving and processing a sample from the hospital associated with the test order; generating a detection report identifying 1 or 2 or 3 human pathogens in the sample; and automatically sending the detection report to the hospital LIS.

Paragraph 2. An in vitro method for reporting test results to a hospital LIS comprising: obtaining a physician test order; generating a pending test order (PTO); conveying the PTO to a hospital's laboratory information system (LIS); generating a test order; conveying the test order to an LIS interchange; generating a clinical instrument test order; conveying the clinical instrument test order to a detection device; receiving and processing a sample from the hospital associated with the physician test order; generating a detection report identifying 1 or 2 or 3 human pathogens in the sample; automatically sending the detection report to the LIS interchange; converting the detection report to a physician test result; automatically sending the physician test result to the hospital LIS.

Paragraph 2: The method of any preceding paragraph, wherein the detection report is automatically sent to the hospital within 90 minutes of when the sample processing began.

Paragraph 3: The method of any preceding paragraph, wherein the detection report includes one or more time stamps selected from the group comprising time stamps such as sample collection, sample ordering, transport to central receiving, central receiving sort, transport to lab, accession of sample, time to process, or time to detection report.

Paragraph 4. The method of any preceding Paragraph, wherein when the detection report identifies four or more pathogens, a multiple infection error alert is sent to the physician.

Paragraph 5. The method of any preceding Paragraph, wherein an alert is sent to practitioners that the detection report is available.

Paragraph 6. The method of any preceding Paragraph, wherein an epidemiology report is generated by the clinical instrument.

Paragraph 7. The method of any preceding Paragraph, wherein the sample is associated with a patient identification tag such as an electronically-readable tag, a wirelessly-readable tag, a radio frequency identification (RFID) tag or an electrically EPROM (EEPROM) tag.

Paragraph 8. An in vitro method for reporting the detection of a human pathogen and/or genetic material thereof comprising: obtaining a sample; loading the sample in a detection system; subjecting a sample to a single multiplex polymerase chain reaction (PCR) thereby detecting a human pathogen; generating a report containing the identification of the pathogen; automatically delivering the report from the detection system to an LIS interchange; delivering the report from the LIS interchange to a hospital LIS.

EXAMPLES

The invention is demonstrated in practical embodiments by the following examples. The embodiments disclosed therein relate to potentially preferred embodiments of the invention and are not intended to limit the scope of the Invention.

Example 1: Gram-Positive Panel, Blood Culture Contamination

False positive *Enterococcus faecalis*, Pan-GN and Pan-*candida* signals were observed when Applicants ran the sLRM GP assay. Applicants investigated whether the blood culture matrix was the source of the contamination.

Desired blood culture bottles were collected. The rubber sealer of each blood culture bottle was cleaned with ethanol before puncturing it with a needle. 75 uL from each bottle was aspirated. sLRM was performed (Bead beater sample-to lyse cell, add 300 uL lysis buffer, 500 uL binding buffer-wait 2 min, and wash with 150 uL wash buffer). 100% of the washed magnetic beads were loaded onto the cartridge. H1 and H3 (annealing heaters) were run at 61.5° C.

A preliminary test of NTC sLRMs (bottle matrix with no blood or bacterial targets) showed high false positive signals for *Enterococcus faecalis*, Pan-*candida*, and Pan-GN but buffer alone runs did not (see FIG. 4). As a result it was determined that contamination is coming from the bottle matrix.

To follow up, 13 negative (no blood or bacterial targets) blood matrices were screened for contaminants. Desired blood culture bottles were collected. 1000 uL of Bottle matrix was collected and the sample bead beated. 1 *S. pombe* lyo pellet (5e5 Colony Forming Unit (CFU)/bead) (control), 75 uL of Bead beaten sample and 300 uL Lysis Buffer was added to an Eppendorf tube. N=8 per bottle type. Waited 5 minutes then added 500 uL of Binding buffer, rotate tubes. Centrifuge briefly and put the tubes onto magnetic racks. Waited for 1-2 minutes and aspirated the liquid using 1000 uL pipettes. Wash the beads with 150 uL of wash buffer, remove residual wash buffer after briefly centrifuging the tubes. Resuspended beads with 150 uL of wash buffer. Loaded 100% of beads onto open bay runs or store them @4 C. Table 4 below summarizes the Pan-GN and Pan-*candida* contaminates identified in the negative blood matrices.

TABLE 4

Blood Culture Bottle Contaminants

| | Brand | Blood Culture Bottle Types | Pan-GP and Pan-*candida* Contaminants identified |
|---|---|---|---|
| 1 | BACTEC | Plus Anaerobic/F | Pan-*candida* |
| 2 | BACTEC | Standard/10 Aerobic/F | Pan-*candida* |
| 3 | BACTEC | Standard Anaerobic/F | Pan-*candida* |
| 4 | BACTEC | Plus Aerobic/F | *Enterococcus Faecalis*, *Enterococcus* spp. Pan *candida* |
| 5 | BACTEC | Pediatric Plus | Pan-candida |
| 6 | BACTEC | Lytic/10 Anaerobic/F | *Enterococcus Faecalis*- Pan-candida |
| 7 | BacT/ALERT | SA Standard Aerobic | None |
| 8 | BacT/ALERT | SN Standard Anaerobic | Pan-*Candida*, *Staphylococcus* |
| 9 | BacT/ALERT | FA Plus | Pan-*candida* |
| 10 | VersaTREK | REDOX 1 Aerobic | Pan-*candida* |
| 11 | VersaTREK | REDOX 2 Anaerobic | Pan-*candida* |
| 12 | BacT/ALERT | FN Plus | Pan-*candida* |
| 13 | BacT/ALERT | PF Plus | Pan-*candida* |

Blood culture matrices that were known to have contaminants were then evaluated on the BCID-GP cartridge. FIG. 5*a* shows *Enterococcus faecalis*, FIG. 5*b* shows *Staphylococcus*, FIG. 5*c* shows *Enterococcus* (genus) and FIG. 5*d* shows Pan-*Candida* were detected when negative blood culture matrices (no blood or bacterial targets) were tested on a BCID-GP cartridge.

Blood culture bottles were sent out for DNA testing by sequencing to confirm DNA was coming from the bottle and not another source. Table 5 below details the percentage of DNA in the empty bottle attributable to the contaminate.

TABLE 5

Percentage of DNA In The Empty Bottle Attributable To The Contaminate

| Genus | BD Anerobic | BD Aerobic |
|---|---|---|
| *Bacillus* | 17.838% | 16.61% |
| *Streptococcus* | 4.838% | 5.51% |
| *Enterococcus* | 0.568% | 0.90% |
| *Micrococcus* | 0.199% | 0.74% |
| *Listeria* | 0.521% | 0.73% |
| *Acinetobacter* | 0.337% | 0.62% |
| *Proteus* | 0.655% | 0.78% |
| *Stenotrophomonas* | 0.024% | 0.30% |

TABLE 5-continued

Percentage of DNA In The Empty Bottle
Attributable To The Contaminate

| Genus | BD Anerobic | BD Aerobic |
|---|---|---|
| Propionibacterium | 0.046% | 0.27% |
| Morganella | 0.124% | 0.24% |
| Staphylococcus | 0.170% | 0.18% |
| Corynebacterium | 0.114% | 0.17% |
| Serratia | 0.062% | 0.14% |
| Pseudomonas | 0.082% | 0.13% |
| Pantoea | 0.052% | 0.11% |
| Lactobacillus | 0.020% | 0.08% |
| Bacteroides | 0.006% | 0.07% |
| Cronobacter | 0.026% | 0.04% |
| Citrobacter | 0.001% | 0.00% |
| Klebsiella | 0.002% | 0.00% |
| Salmonella | 0.001% | 0.00% |
| Enterobacter | 0.000% | 0.0004% |
| Neisseria | 0.000% | 0.0004% |
| Prevotella | 0.019% | 0.00% |

Example 2: Gram-Positive *Enterococcus faecalis* DNA Contamination

Figure 6B:
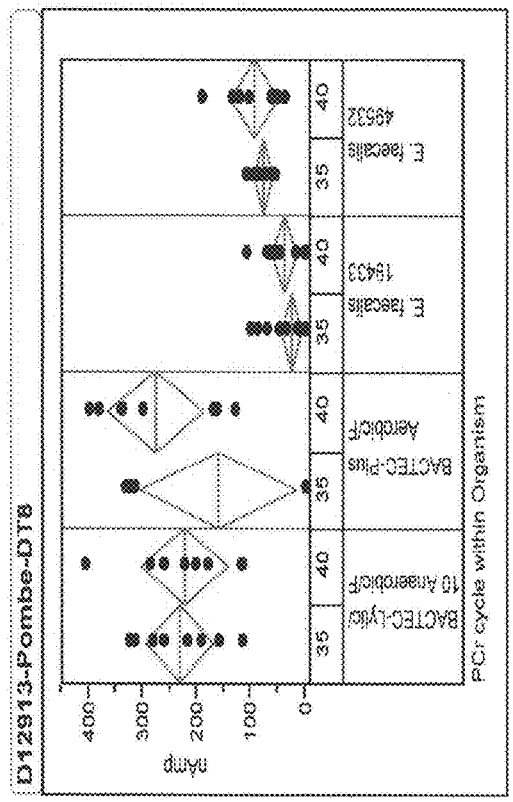
FIG. 6A and FIG. 6B.
Figure 6A:
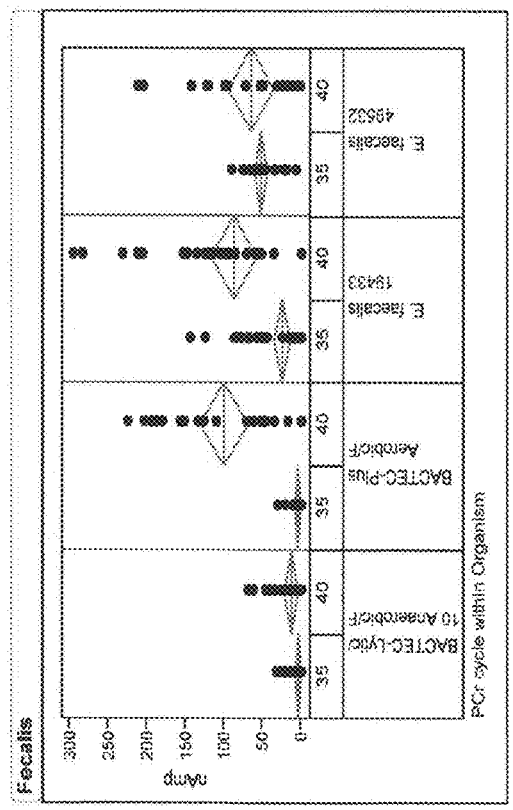

In order to eliminate *Enterococcus faecalis* signals coming from the blood culture matrices, reduced PCR cycling was evaluated. Two strains of *Enterococcus faecalis* (*Enterococcus faecalis* ATCC19433 and *Enterococcus faecalis* ATCC49532) at 1× Limit of Detection (LoD) (1×105 CFU/mL) were PCR cycled 40 and 35 times. Specifically, 10 sLRM were made for each strain type and dilute to 50% beads. FIG. 6A shows that *Enterococcus faecalis* contamination signals are reduced but not eliminated with 35 cycles and the *S. pombe* internal control is still detected (See FIG. 6B).

Next, 30-cycle PCR was evaluated. FIGS. 7a and 7b show 2 types of negative blood culture bottles (Bactec plus aerobic and Peds plus/f), using 75 uL direct input tested on open bay runs. False positive signal from blood culture bottles is eliminated using a 30-cycle PCR. Only the positive internal controls (*S. pombe* and DT9) were detected. FIGS. 7c and 7d show that detection is possible (although weak) at 1×LOD (1×105 CFU/mL) *Enterococcus faecalis* run on sLRMs using a 30-cycle PCR.

Because *Enterococcus faecalis* will run with a 30-cycle PCR, it was combined/pooled with the Pan-GN primers which also cycle 30 times.

Example 3: Gram-Positive, *Streptococcus* Spp. and *P. acnes* Contamination

It was observed that the BCID-GP panel also detects common gram-positive organisms or nucleic acid found in the blood culture bottles. Detection of these organisms from the environment leads to false positives. *Streptococcus* spp. and *P. acnes* lead to the most number of false positives. To mitigate the risk of false positives, *Streptococcus* and *P. acnes* were amplified with decreased cycling (30 or 35 cycles from 40). Amplification conditions are as follows:

TABLE 6

Bench PCR conditions for primer optimization

| PCR Component | Working Concentrations |
|---|---|
| PCR Buffer 1X + MgCl2 | 1.25X and 3 mM, respectively |
| dNTPs | 0.8 mM |
| AptaTaq LDX | 4U/rxn |
| Enhancer with 0.1% Tween | 1X |
| Multiplex Primer Mix | 1X |
| Total PCR Reaction | 2 μL |

TABLE 7

PCR Cycling conditions

| | Cycles | Temp. | Time |
|---|---|---|---|
| Stage 1 | 1X | 95° C. | 20" |
| Stage 2 | 40X | 95° C. | 3" |
| | 35X | 60° C. | 18" |
| | 30X | | |

Tests using a BDIC-GP cartridge spotted with *P. acnes* primers show that *P. acnes* false positives are detected with 40 and 35 cycles but eliminated with 30 cycle PCR (FIG. 8). Thus, decreasing cycles eliminates contamination detection of *P. acnes* coming from negative blood culture matrices.

Next, Applicants analyzed whether 30 cycles allows sufficient amplification to detect the targets at 1×LOD. Negative blood culture matrixes (10 mL of blood in a blood culture bottle) were spiked with *P. acnes*. The *P. acnes* was then bead beaten. 100 uL of bead beaten sample and 1 *S. pombe* lyo pellet was then added to 300 uL of lysis buffer and incubated for 1 minute. Following that 500 uL of binding buffer was added and incubated for 2 minutes. The magnetic beads were then collected and washed once with 150 uL of wash, they were then resuspended in 150 uL of wash and transferred to open bays.

Figure 9A:
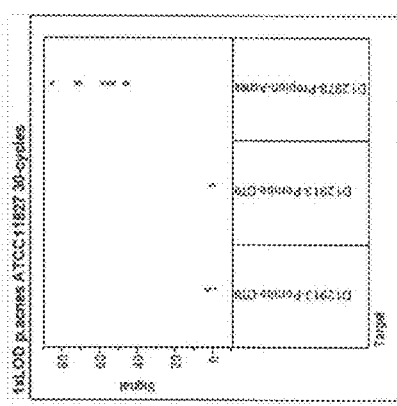
FIG. 9A and FIG. 9B: When 30 PCR cycles are used, *P. acnes* is detected at 1×LOD (1×106 CFU/mL) (9A for *P. acnes* strain ATCC11827 and 9B for *P. acnes* strain ATCC6919).
Figure 9B:
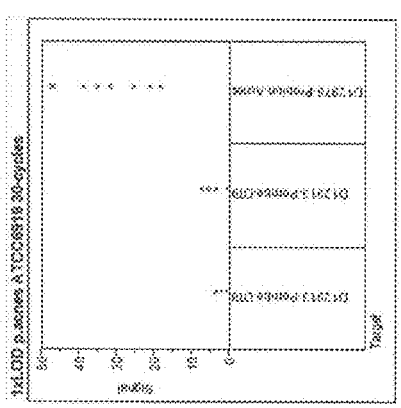

FIG. 9 shows that when 30 PCR cycles are used, the sLRM assay is still capable of detecting *P. acnes* at 1×LOD (1×106 CFU/mL). (FIGS. 9a and 9b).

Six representative *Streptococcus* species were also tested and shown not to produce false positive signals using 30 PCR cycles on BCID-GP cartridges (data not shown) yet capable of 1×LOD (1×106 CFU/mL) detection. FIG. 10.

Primer optimization: Because *Streptococcus* spp. and *P. acnes* have reduced PCR cycling to avoid false positives while maintaining target sensitivity, they were placed in their own primer pool on the PCB board. The primers were combined with Internal Control 1 (IC1) template and IC1 primers. IC1 is a synthetic ssDNA sequence with zero mismatches in the primer binding regions. *Streptococcus* spp. and *P. acnes* primers were initially evaluated at their original working concentrations of 250 nM but were increased to 500 nM for improved performance. Three *P. acnes* strains and two *Streptococcus* species were tested on open bays. All targets were detected at 1×LOD (1×106 CFU/mL) (FIG. 11). While the *P. acnes* signal is less robust than the *Streptococcus* spp. signal, it is above the signal threshold (10 namps).

TABLE 8

| | Multiplex Pool formulation | | | | | |
|---|---|---|---|---|---|---|
| Pool | Organisms and Drug Resistance | Target | For Primer ID | Rev Primer ID | Working [Primer] nM | Amplicon size bp |
| MP5 | propionibacterium | rpoB-Prop | D12933 | D12936 | 500 | 183 |
| | Streptococcus spp. | 16s RNA-Strep | D12193 | D12945 | 500 | 110 |
| | IC1 | IC1 | D19507-H3 | D19506-H3 | 250 | 99 |
| | Internal Control 1 | | D19505 | | 1000 copies | |

In order to finalize the multiplex primer pool, it was necessary to confirm whether contamination signals were eliminated. NTC sLRMs were run with 100% bead loading to evaluate contamination levels. The results demonstrated that no *Streptococcus* spp or *P. acnes* signals were detected while the *S. pombe* and IC1 control signals were detected. FIG. 12.

Example 4: Gram-Positive, Contamination Mitigation

Next Applicants evaluated 37-cycle PCR for all targets to reduce or eliminate contamination from blood matrix bottles. Three types of bottles were tested (Bactec Pediatric Plus/F, Bactec Aerobic Plus/F, Bactec Anaerobic Lytic/10) with and without blood.

Surprisingly, when PCR cycles are reduced from 40 to 37, most blood matrix contamination is eliminated. FIG. 13.

Example 5: Gram-Positive, Detuning to Eliminate Blood Culture Contamination

In light of the above experiments, Applicants reduced all cycling to 35 or 30 cycles. Even with the reduction in cycles, false positives were still detected. For example, *Corynebacterium* was reduced from 40 to 35 and then to 30 cycles but false positives persisted. Applicants then dropped the primer concentration by 50% to 250 nM and the false positives were eliminated. Enterococccus false positives were eliminated when PCR cycles were dropped from 40 to 35 cycles and primer concentration was reduced by 50% to 250 nM. *S anginosus* false positives were eliminated when PCR cycles were dropped from 40 to 35 cycles and primer concentration was reduced by 75% to 250 nM. The primer concentration for the other targets ranges from 125 to 1000 nM. As summarized in the table below, Applicants were surprisingly able to make their BCID-GP assay less sensitive, to eliminate or reduce detection of contaminants in the sample by "detuning" which in some cases involved only the reduction in the number of cycles and in other cases involved the combined reduction in cycling and reduction in primer concentration and thresholding.

TABLE 9

| Target | Before detuning | After detuning | Assay thresholds (nA) |
|---|---|---|---|
| B cereus | not detected | not detected | 20 |
| B subtilis | detected | not detected | 20 |
| Corynebacterium | detected | not detected | 10 |
| Enterococccus | detected | not detected | 20 |
| E faecalis | detected | not detected | 20 |

TABLE 9-continued

| Target | Before detuning | After detuning | Assay thresholds (nA) |
|---|---|---|---|
| E faecium | detected | not detected | 20 and requires Entero call |
| Lactobacillus | not detected | not detected | 20 |
| Listeria | not detected | not detected | 20 |
| L monocytogenes | not detected | not detected | 20 |
| Micrococcus | detected | not detected | 30 |
| P acnes | detected | not detected | 50 |
| Staphylococcus | detected | not detected | 50 |
| S aureus | detected | not detected | 20 |
| S epidermidis | detected | not detected | 20 |
| S lugdunensis | not detected | not detected | 20 |
| Streptococcus | detected | not detected | 70 |
| S agalactiae | detected | not detected | 100 |
| S anginosus | detected | not detected | 20 |
| S pneumoniae | detected | not detected | 20 |
| S pyogenes | detected | not detected | 50 |
| S maltophilia | detected | not detected | 30 |
| Pan-GN | detected | not detected | 100 |
| Pan-Candida | not detected | not detected | 10 |
| mecA | detected | not detected | 20 |
| mecC | not detected | not detected | 20 |
| vanA | not detected | not detected | 20 |
| vanB | not detected | not detected | 20 |

Example 6, Gram-Positive, Use of Benzonase to Remove Bottle Culture Contaminates In the above Examples, the goal was to amplify PCR products in a single PCR run under conditions appropriate for the substantial reduction or elimination of electrochemical detection of contaminating pathogen and/or genetic material present in the sample. Next Applicants sought to reduce or eliminate the concentration of contaminating nucleic acids in the sample. The invention employs nucleases to remove contaminating nucleic acids. Exemplary nucleases include BENZONASE®, PULMOZYME®; or any other DNase or RNase commonly used within the art.

Enzymes such as BENZONASE® degrade nucleic acid and have no proteolytic activity. As with all endonucleases, BENZONASE® hydrolyzes internal phosphodiester bonds between specific nucleotides. Upon complete digestion, all free nucleic acids present in solution are reduced to oligonucleotides 2 to 4 bases in length. It is well known that nucleic acids may adhere to cell derived particles such as viruses. BENZONASE® has been used to purify samples with viral targets. See e.g. U.S. Pat. No. 9,428,768 which is herein incorporated in its entirety by reference. What is not known is whether BENZONASE® would be useful in removing non-viable organisms (bacteria or fungi) found in growth media without interfering with detection of a bacterial or fungal target in the sample.

15 clinical samples were tested on the BCID-GP Panel that had previously given *Enterococcus faecium* false positives. Specifically, samples were treated with Benzonase+1 mM MgCl2 for 5 min. at 37 C or room temperature. Benzonase eliminated all false positives. Room temperature incubation was as effective as 37 C incubation Next, the blood bottle, BacT/Alert FA Plus blood matrix, which has *Bacillus subtilis* DNA contamination, was treated with Benzonase as described above. Without Benzonase treatment, the blood culture matrix gave background signals of 1.9-10.9 nA but 9 replicates of Benzonase-treated matrix did not give any signal greater than 0.2 nA, thus eliminating false positive signals.

Next, whether Benzonase impacts target detection was tested. 5 clinical samples were tested on the BCID-GN panel that had previously given false positives. Samples were treated with Benzonase at room temperature for 5 min and 2 hr. All false positives signals were eliminated and all true targets were detected with 5 and 2 hr treatment, but several target signals decreased with the 2 hr. treatment.

Next, 3×LOD (3×106 CFU/mL) Multiplex Primer Pool (MP) mix #3 (comprising *Escherichia coli, Lactobacillus paracasei, Streptococcus pyogenes, Listeria innocua, Candida albicans*) and blood/BC matrix with 0, 5' or 2 hrs Benzonase treatment was tested and run on BCID-GP cartridge with 35, 30 and 40 PCR cycles. All LOD targets were detected with 5' and 2 hr benzonase treatment with both 30 and 35 PCR cycling parameters. Not all contamination is eliminated with 40-cycle PCR.

BENZONASE® is well suited for reducing nucleic acid and/or non-viable bacterial and fungal organisms without adversely impacting the detection of clinically relevant bacteria (gram-positive/gram-negative) or fungal targets.

Example 7: Gram-Positive Panel, Limit of Detection (Analytical Sensitivity)

The BCID-GP Multiplex primer pool and PCR cycles are shown in FIG. 14. Each of the 8 PCR drops contains an internal control *S. pombe* is the control target in PCR drops 1-4 (30-cycle PCR) Synthetic Control 1 (SC1) is the control target in PCR drops 5-8 (35-cycle PCR).

The PCR cycling conditions are as follows:

TABLE 10

| BCID-GP PCR cycling | | | |
|---|---|---|---|
| | Denature 95.5° C. | Anneal/Extend 65.0° C. | Cycle No. |
| Hot Start | 30 sec. | | |
| Step 1 | 3 sec. | 30 sec. | 1-30 or 1-35 |

This primer pool and PCR cycling are used for Examples 7-10. The BCID-GP cartridge layout is shown in FIG. 15 and was also used in Examples 7-10.

The limit of detection (LoD), or analytical sensitivity, was identified and verified for each assay on the BCID-GP Panel using quantified reference strains. To facilitate testing, five organism mixes were made at varying concentrations and serial dilutions were prepared in simulated blood culture sample matrix which is defined as the matrix from a negative blood culture bottle mixed with whole blood and EDTA in the same ratio as the manufacturer recommends for blood culture. At least 20 replicates per target were tested for each condition. The limit of detection was defined as the lowest concentration of each target that is detected in >95% of tested replicates. The confirmed LoD for each BCID-GP Panel organism is shown in Table 11.

TABLE 11

| LoD Results Summary | | | |
|---|---|---|---|
| Target | Organism | Strain | LoD Concentration |
| *Bacillus cereus* Group | *Bacillus cereus* | ATCC 21769 | $1 \times 10^5$ CFU/mL |
| *Bacillus subtilis* Group | *Bacillus subtilis* | ATCC 55614 | $1 \times 10^5$ CFU/mL |
| *Corynebacterium* | *Corynebacterium striatum* | ATCC 43735 | $1 \times 10^6$ CFU/mL |
| *Enterococcus* | *Enterococcus casseliflavus* | ATCC 25788 | $1 \times 10^5$ CFU/mL |
| *Enterococcus faecalis* | *Enterococcus faecalis* (vanB+) | ATCC 51575 | $1 \times 10^6$ CFU/mL |
| *Enterococcus faecium* | *Enterococcus faecium* (vanA+) | ATCC BAA-2317 | $1 \times 10^6$ CFU/mL |
| *Lactobacillus* | *Lactobacillus paracasei* | ATCC 25598 | $1 \times 10^5$ CFU/mL |
| *Listeria* | *Listeria monocytogenes* | ATCC 10890 | $1 \times 10^5$ CFU/mL |
| *Listeria monocytogenes* | *Listeria monocytogenes* | ATCC 10890 | $1 \times 10^5$ CFU/mL |
| *Micrococcus* | *Micrococcus luteus* | ATCC 19212 | $1 \times 10^6$ CFU/mL |
| *Propionibacterium acnes* | *Propionibacterium acnes* | ATCC 6919 | $1 \times 10^8$ CFU/mL |
| *Staphylococcus* | *Staphylococcus lugdunensis* | NRS 879 | $1 \times 10^5$ CFU/mL |
| *Staphylococcus aureus* | *Staphylococcus aureus* (mecC+) | ATCC BAA-2313 | $1 \times 10^5$ CFU/mL |
| *Staphylococcus epidermidis* | *Staphylococcus epidermidis* (mecA+) | ATCC 35983 | $1 \times 10^5$ CFU/mL |
| *Staphylococcus lugdunensis* | *Staphylococcus lugdunensis* | NRS 879 | $1 \times 10^5$ CFU/mL |
| *Streptococcus* | *Streptococcus pneumoniae* | ATCC BAA-475 | $1 \times 10^5$ CFU/mL |
| *Streptococcus agalactiae* | *Streptococcus agalactiae* | ATCC 12401 | $1 \times 10^6$ CFU/mL |
| *Streptococcus anginosus* group | *Streptococcus anginosus* | ATCC 9895 | $1 \times 10^5$ CFU/mL |
| *Streptococcus pneumoniae* | *Streptococcus pneumoniae* | ATCC BAA-475 | $1 \times 10^5$ CFU/mL |

TABLE 11-continued

LoD Results Summary

| Target | Organism | Strain | LoD Concentration |
|---|---|---|---|
| Streptococcus pyogenes | Streptococcus pyogenes | ATCC 12384 | $1 \times 10^5$ CFU/mL |
| mecA | Staphylococcus epidermidis (mecA+) | ATCC 35983 | $1 \times 10^4$ CFU/mL |
| mecC | Staphylococcus aureus (mecC+) | ATCC BAA-2313 | $1 \times 10^4$ CFU/mL |
| vanA | Enterococcus faecium (vanA+) | ATCC BAA-2317 | $1 \times 10^4$ CFU/mL |
| vanB | Enterococcus faecalis (vanB+) | ATCC 51575 | $1 \times 10^4$ CFU/mL |
| PanCandida | Candida albicans | ATCC 24433 | $1 \times 10^6$ CFU/mL |
|  | Candida glabrata | ATCC 66032 | $1 \times 10^6$ CFU/mL |
| Pan Gram-Negative | Escherichia coli | ATCC 4157 | $1 \times 10^6$ CFU/mL |
|  | Stenotrophomonas maltophilia | ATCC 13636 | $1 \times 10^6$ CFU/mL |

Example 8, Gram-Positive, Analytical Reactivity (Inclusivity and Exclusivity)

A panel of 158 strains/isolates representing the genetic, temporal and geographic diversity of each target on the BCID-GP Panel was evaluated to demonstrate analytical reactivity. Each strain was tested in triplicate at 1×108 CFU/mL while each fungus was tested at 1×106 CFU/mL in simulated sample matrix.

All of the 158 strains/isolates tested for inclusivity were detected by the BCID-GP Panel. Results of analytical reactivity are shown in Table 12.

Analytical Specificity (Cross-Reactivity and Exclusivity)

Cross-reactivity of on-panel analytes was evaluated using data generated from the Analytical Reactivity study. Cross-reactivity of off-panel organisms was evaluated by testing a 30 member panel, containing clinically-relevant bacteria and fungi. Bacterial targets were tested at a concentration of ≥1×109 CFU/mL while fungi were tested at a concentration of ≥1×107 CFU/mL. In three cases where ≥1×109 CFU/mL could not be achieved in culture for bacteria, a two-fold dilution of the stock material was used as reflected in Table 12. Table 12 summarizes the results of the on-panel organism strains tested. Each on-panel strain was tested in triplicate. Table 13 summarizes the results of the off-panel fungal and bacterial strains tested. No cross-reactivity was observed for any of the off nor on-panel organisms with any of the assays.

TABLE 12

Analytical Reactivity (Inclusivity, Cross-Reactivity, and Exclusivity) Results

| Organism | Strain | Percent Detected | Percent Pos-itivity | Cross-Reactivity Result |
|---|---|---|---|---|
| Bacillus cereus | ATCC 10876 | 100% | 100% | Not Observed |
| Bacillus thuringiensis | ATCC 10792 | 100% | 100% | Not Observed |
|  | ATCC 35646 | 100% | 100% | Not Observed |
| Bacillus amyloliquefaciens | ATCC 23350 | 100% | 100% | Not Observed |
|  | ATCC 23845 | 100% | 100% | Not Observed |
| Bacillus atrophaeus | ATCC 6455 | 100% | 100% | Not Observed |
|  | ATCC 6537 | 100% | 100% | Not Observed |
| Bacillus licheniformis | ATCC 21039 | 100% | 100% | Not Observed |
|  | ATCC 21667 | 100% | 100% | Not Observed |
| Bacillus subtilis | ATCC 15561 | 100% | 100% | Not Observed |
| Corynebacterium diphtheriae | ATCC 39255 | 100% | 100% | Not Observed |
|  | ATCC 53281 | 100% | 100% | Not Observed |

TABLE 12-continued

Analytical Reactivity (Inclusivity, Cross-Reactivity, and Exclusivity) Results

| Organism | Strain | Percent Detected | Percent Pos-itivity | Cross-Reactivity Result |
|---|---|---|---|---|
| Corynebacterium ulcerans | ATCC 51799 | 100% | 100% | Not Observed |
| Corynebacterium jeikeium | ATCC BAA-949 | 100% | 100% | Not Observed |
|  | ATCC BAA-950 | 100% | 100% | Not Observed |
|  | ATCC 43734 | 100% | 100% | Not Observed |
| Corynebacterium urealyticum | ATCC 43044 | 100% | 100% | Not Observed |
| Corynebacterium striatum | ATCC 7094 | 100% | 100% | Not Observed |
| Enterococcus avium | ATCC 14025 | 100% | 100% | Not Observed |
| Enterococcus gallinarum | ATCC 49608 | 100% | 100% | Not Observed |
| Enterococcus hirae | ATCC 49479 | 100% | 100% | Not Observed |
| Enterococcus casseliflavus | ATCC 700327 | 100% | 100% | Not Observed |
| Enterococcus raffinosus | ATCC 49464 | 100% | 100% | Not Observed |
| Enterococcus saccharolyticus | ATCC 43076 | 100% | 100% | Not Observed |
| Enterococcus faecalis | ATCC 14506 | 100% | 100% | Not Observed |
|  | ATCC 19433 | 100% | 100% | Not Observed |
|  | ATCC 29200 | 100% | 100% | Not Observed |
|  | ATCC 49149 | 100% | 100% | Not Observed |
|  | ATCC 49332 | 100% | 100% | Not Observed |
|  | ATCC 49452 | 100% | 100% | Not Observed |
|  | ATCC 49474 | 100% | 100% | Not Observed |
|  | ATCC 49532 | 100% | 100% | Not Observed |
| Enterococcus faecalis (vanB+) | ATCC BAA-2365 | 100% | 100% | Not Observed |
| Enterococcus faecium | ATCC 19953 | 100% | 100% | Not Observed |
|  | ATCC 23828 | 100% | 100% | Not Observed |
|  | ATCC 27270 | 100% | 100% | Not Observed |
|  | ATCC 27273 | 100% | 100% | Not Observed |
|  | ATCC 35667 | 100% | 100% | Not Observed |
|  | ATCC 49224 | 100% | 100% | Not Observed |
|  | ATCC 49624 | 100% | 100% | Not Observed |
| Enterococcus faecium (vanA+) | ATCC 51559 | 100% | 100% | Not Observed |
|  | ATCC 700221 | 100% | 100% | Not Observed |
|  | ATCC BAA-2316 | 100% | 100% | Not Observed |
|  | ATCC BAA-2318 | 100% | 100% | Not Observed |
|  | ATCC BAA-2319 | 100% | 100% | Not Observed |
|  | ATCC BAA-2320 | 100% | 100% | Not Observed |

TABLE 12-continued

Analytical Reactivity (Inclusivity, Cross-Reactivity, and Exclusivity) Results

| Organism | Strain | Percent Detected | Percent Pos-itivity | Cross-Reactivity Result |
|---|---|---|---|---|
| Enterococcus faecium (vanB+) | ATCC 51858 | 100% | 100% | Not Observed |
| Listeria monocytogenes | ATCC 13932 | 100% | 100% | Not Observed |
|  | ATCC 19111 | 100% | 100% | Not Observed |
|  | ATCC 19112 | 100% | 100% | Not Observed |
| Listeria innocua | NCTC 11288 | 100% | 100% | Not Observed |
| Listeria ivanovii | ATCC 19119 | 100% | 100% | Not Observed |
|  | ATCC BAA-139 | 100% | 100% | Not Observed |
| Listeria seeligeri | ATCC 35967 | 100% | 100% | Not Observed |
| Listeria welshimeri | ATCC 35897 | 100% | 100% | Not Observed |
| Lactobacillus casei | ATCC 334 | 100% | 100% | Not Observed |
|  | ATCC 39392 | 100% | 100% | Not Observed |
| Lactobacillus paracasei | ATCC 27092 | 100% | 100% | Not Observed |
| Lactobacillus rhamnosus | ATCC 39595 | 100% | 100% | Not Observed |
|  | ATCC 53103 | 100% | 100% | Not Observed |
| Micrococcus luteus | ATCC 400 | 100% | 100% | Not Observed |
|  | ATCC 4698 | 100% | 100% | Not Observed |
| Micrococcus yunnanensis | ATCC 7468 | 100% | 100% | Not Observed |
| Propionibacterium acnes | ATCC 11827 | 100% | 100% | Not Observed |
| Staphylococcus gallinarum | ATCC 700401 | 100% | 100% | Not Observed |
| Staphylococcus haemolyticus | ATCC 29970 | 100% | 100% | Not Observed |
|  | ATCC 31874 | 100% | 100% | Not Observed |
| Staphylococcus hominis | ATCC 27844 | 100% | 100% | Not Observed |
|  | ATCC 700236 | 100% | 100% | Not Observed |
|  | NRS 871 | 100% | 100% | Not Observed |
| Staphylococcus hyicus | ATCC 11249 | 100% | 100% | Not Observed |
| Staphylococcus lentus | ATCC 700403 | 100% | 100% | Not Observed |
| Staphylococcus capitis | ATCC 35661 | 100% | 100% | Not Observed |
|  | NRS 866 | 100% | 100% | Not Observed |
| Staphylococcus chromogenes | ATCC 43764 | 100% | 100% | Not Observed |
| Staphylococcus cohnii | ATCC 29974 | 100% | 100% | Not Observed |
| Staphylococcus vitulinus | ATCC 51161 | 100% | 100% | Not Observed |
| Staphylococcus pasteuri | ATCC 51129 | 100% | 100% | Not Observed |
| Staphylococcus simulans | ATCC 27850 | 100% | 100% | Not Observed |
|  | ATCC 27851 | 100% | 100% | Not Observed |
| Staphylococcus aureus | ATCC 11632 | 100% | 100% | Not Observed |
|  | ATCC 14775 | 100% | 100% | Not Observed |
|  | ATCC 29213 | 100% | 100% | Not Observed |
|  | ATCC 29247 | 100% | 100% | Not Observed |
|  | ATCC 6538P | 100% | 100% | Not Observed |
|  | ATCC 25923 | 100% | 100% | Not Observed |
| Staphylococcus aureus (mecA+) | NRS 383 | 100% | 100% | Not Observed |
|  | NRS 384 | 100% | 100% | Not Observed |
|  | NRS 385 | 100% | 100% | Not Observed |
|  | NRS 387 | 100% | 100% | Not Observed |
|  | NRS 483 | 100% | 100% | Not Observed |
|  | NRS 484 | 100% | 100% | Not Observed |
|  | NRS 643 | 100% | 100% | Not Observed |
|  | NRS 645 | 100% | 100% | Not Observed |
|  | NRS 653 | 100% | 100% | Not Observed |
|  | ATCC 700698 | 100% | 100% | Not Observed |
|  | ATCC 700699 | 100% | 100% | Not Observed |
|  | ATCC BAA-1707 | 100% | 100% | Not Observed |
|  | ATCC BAA-40 | 100% | 100% | Not Observed |
|  | ATCC BAA-42 | 100% | 100% | Not Observed |
|  | ATCC BAA-43 | 100% | 100% | Not Observed |
|  | NRS 382 | 100% | 100% | Not Observed |
|  | NRS 386 | 100% | 100% | Not Observed |
|  | NRS 647 | 100% | 100% | Not Observed |
|  | NRS 654 | 100% | 100% | Not Observed |
|  | NRS 655 | 100% | 100% | Not Observed |
|  | NRS 657 | 100% | 100% | Not Observed |
|  | NRS 659 | 100% | 100% | Not Observed |
|  | NRS 648 | 100% | 100% | Not Observed |
|  | NRS 651 | 100% | 100% | Not Observed |
| Staphylococcus epidermidis | ATCC 49134 | 100% | 100% | Not Observed |
|  | ATCC 700583 | 100% | 100% | Not Observed |
|  | NCIMB 8853 | 100% | 100% | Not Observed |
| Staphylococcus epidermidis (mecA+) | ATCC 49461 | 100% | 100% | Not Observed |
| Staphylococcus lugdunensis | ATCC 49576 | 100% | 100% | Not Observed |
| Streptococcus mitis | ATCC 15914 | 100% | 100% | Not Observed |
|  | ATCC 49456 | 100% | 100% | Not Observed |
| Streptococcus dysgalactiae | ATCC 43078 | 100% | 100% | Not Observed |
|  | ATCC 35666 | 100% | 100% | Not Observed |
| Streptococcus equi | ATCC 9528 | 100% | 100% | Not Observed |
| Streptococcus gallolyticus | ATCC 49475 | 100% | 100% | Not Observed |
|  | ATCC 9809 | 100% | 100% | Not Observed |
| Streptococcus infantis | ATCC 700779 | 100% | 100% | Not Observed |
| Streptococcus oralis | ATCC 35037 | 100% | 100% | *Not Observed |
| Streptococcus parasanguinis | ATCC 15909 | 100% | 100% | Not Observed |
| Streptococcus salivarius | ATCC 25975 | 100% | 100% | Not Observed |
|  | ATCC 7073 | 100% | 100% | Not Observed |
| Streptococcus thoraltensis | ATCC 700865 | 100% | 100% | Not Observed |
| Streptococcus gordonii | ATCC 10558 | 100% | 100% | Not Observed |
| Streptococcus agalactiae | ATCC 12403 | 100% | 100% | Not Observed |
|  | ATCC 12973 | 100% | 100% | Not Observed |
|  | ATCC 13813 | 100% | 100% | Not Observed |
| Streptococcus pneumoniae | ATCC 6315 | 100% | 100% | Not Observed |
|  | ATCC 6321 | 100% | 100% | Not Observed |
|  | ATCC 700673 | 100% | 100% | *Not Observed |
|  | ATCC 700674 | 100% | 100% | Not Observed |
|  | ATCC BAA-659 | 100% | 100% | Not Observed |
|  | ATCC BAA-1656 | 100% | 100% | Not Observed |
|  | ATCC BAA-1667 | 100% | 100% | Not Observed |
| Streptococcus pyogenes | ATCC 14289 | 100% | 100% | Not Observed |
|  | ATCC 19615 | 100% | 100% | Not Observed |
| Streptococcus anginosus | NCTC 10713 | 100% | 100% | Not Observed |
| Streptococcus constellatus | ATCC 27513 | 100% | 100% | Not Observed |
| Streptococcus intermedius | ATCC 27335 | 100% | 100% | Not Observed |
| Candida krusei | ATCC 32196 | 100% | 100% | Not Observed |
| Candida parapsilosis | ATCC 58895 | 100% | 100% | Not Observed |
| Acinetobacter baumanii | NCTC 13420 | 100% | 100% | Not Observed |
| Bacteroides fragilis | NCTC 9343 | 100% | 100% | Not Observed |
| Citrobacter freundii | NCTC 9750 | 100% | 100% | Not Observed |
| Enterobacter cloacae | ATCC 13047 | 100% | 100% | Not Observed |
| Fusobacterium necrophorum | ATCC 25286 | 100% | 100% | *Not Observed |
| Haemophilus influenzae | ATCC 4560 | 100% | 100% | Not Observed |
| Klebsiella pneumoniae | ATCC 51503 | 100% | 100% | Not Observed |
| Neisseria meningitides (serogroup B) | ATCC 13113 | 100% | 100% | Not Observed |
| Proteus mirabilis | ATCC 43071 | 100% | 100% | Not Observed |
| Pseudomonas aeruginosa | ATCC 15442 | 100% | 100% | Not Observed |
| Salmonella enterica subsp. enterica | ATCC 51957 | 100% | 100% | Not Observed |
| Serratia marcescens | ATCC 8100 | 100% | 100% | Not Observed |

*One replicate had a low-level signal for Pan-Candida. Repeat testing of three additional replicates showed no false positive signals.

TABLE 13

Cross-reactivity with Targets Not Detected by the BCID-GP Panel (Exclusivity)

| Organism | Strain | Highest Concentration Tested | Cross-Reactivity Result |
|---|---|---|---|
| Aspergillus fumigatus | ATCC 204305 | $1 \times 10^7$ CFU/mL | Not observed |
| Candida orthopsilosis | ATCC 96139 | $1 \times 10^7$ CFU/mL | Not observed |
| Cryptococcus neoformans | ATCC 14116 | $1 \times 10^7$ CFU/mL | Not observed |
| Rhodotorula minuta | ATCC 36236 | $1 \times 10^7$ CFU/mL | Not observed |
| Saccharomyces cerevisiae | ATCC 18824 | $1 \times 10^7$ CFU/mL | Not observed |
| Trichosporon asahii | ATCC 201110 | $1 \times 10^7$ CFU/mL | Not observed |
| Abiotrophia defectiva | ATCC 49176 | $1 \times 10^9$ CFU/mL | Not observed |
| Actinomyces odontolyticus | ATCC 17929 | $1 \times 10^9$ CFU/mL | Not observed |
| Aerococcus urinae | ATCC 700306 | $1 \times 10^9$ CFU/mL | Not observed |
| Aerococcus viridans | ATCC 10400 | $1 \times 10^9$ CFU/mL | Not observed |
| Anaerococcus prevotii | ATCC 9321 | $1 \times 10^9$ CFU/mL | Not observed |
| Arcanobacterium haemolyticum | ATCC BAA-1784 | $4.1 \times 10^8$ CFU/mL | Not observed |
| Arthrobacter psychrolactophilus | ATCC 700733 | $1 \times 10^9$ CFU/mL | Not observed |
| Carnobacterium malt aromaticum | ATCC 27865 | $3.6 \times 10^8$ CFU/mL | Not observed |
| Cellulomonas turbata | ATCC 25835 | $1 \times 10^9$ CFU/mL | Not observed |
| Clostridium clostridioforme | ATCC 25537 | $1 \times 10^9$ CFU/mL | Not observed |
| Granulicatella adiacens | ATCC 43205 | $1 \times 10^9$ CFU/mL | Not observed |
| Granulicatella elegans | ATCC 700633 | $3.6 \times 10^8$ CFU/mL | Not observed |
| Kocuria kristinae | ATCC BAA-752 | $1 \times 10^9$ CFU/mL | Not observed |
| Leuconostoc carnosum | ATCC 49367 | $1 \times 10^9$ CFU/mL | Not observed |
| Leuconostoc citreum | ATCC 13146 | $1 \times 10^9$ CFU/mL | Not observed |
| Leuconostoc mesentero ides | ATCC 8293 | $1 \times 10^9$ CFU/mL | Not observed |
| Macrococcus caseolyticus | ATCC 29750 | $1 \times 10^9$ CFU/mL | Not observed |
| Pediococcus acidilactici | ATCC 8042 | $1 \times 10^9$ CFU/mL | Not observed |
| Peptostreptococcus anaerobius | ATCC 27337 | $1 \times 10^9$ CFU/mL | Not observed |
| Propionibacterium granulosum | ATCC 11829 | $1 \times 10^9$ CFU/mL | Not observed |
| Propionibacterium propionicum | ATCC 14157 | $1 \times 10^9$ CFU/mL | Not observed |
| Rhodococcus equi | ATCC 6939 | $1 \times 10^9$ CFU/mL | Not observed |
| Rothia dentocariosa | ATCC 31918 | $1 \times 10^9$ CFU/mL | Not observed |
| Rothia mucilaginosa | ATCC 25296 | $1 \times 10^9$ CFU/mL | Not observed |

Example 9: Gram-Positive Panel, Competitive Inhibition

Detection of more than one clinically relevant on-panel organism in a sample was evaluated with the BCID-GP Panel using eight selected organisms which were grouped into mixes of two or three organisms per mix in a blood culture matrix. Test case scenarios paired mixes with one mix at approximately ten times the analytically determined limit of detection (10×LoD) and a second at high titer ($1 \times 10^8$ CFU/mL for bacterial targets and $1 \times 10^7$ CFU/mL for Candida albicans) and vice versa. The organism mixes and combined mixes are summarized in Table 14 and Table 15. All targets were detected in the combinations specified in Table 15 with the exception of mecA in combined mix 2. mecA (carried by S. aureus) was not detected and therefore further tested at 10-fold higher levels in order to achieve 100% detection. The results of co-detection testing demonstrate the ability of the BCID-GP to detect two on-panel organisms in a sample at both high and low concentrations.

TABLE 14

Detection of Co-Infections: Organism Mixes

| Organism Mix 1 | Organism Mix 2 | Organism Mix 3 |
|---|---|---|
| Enterococcus faecium (vanA+) | Klebsiella pneumoniae | Enterococcus faecalis (vanB+) |
| Escherichia coli | Lactobacillus casei | Streptococcus pneumoniae |
| Staphylococcus aureus (mecA+) | Candida albicans | |

TABLE 15

Detection of Co-Infections: Organism Mix Pairings

| Combined Mix ID | Concentration | |
|---|---|---|
| | 10X LoD | $1 \times 10^8$ CFU/mL* |
| 1 | Mix 1 | Mix 2 |
| 2 | Mix 1 | Mix 3 |
| 3 | Mix 2 | Mix 1 |
| 4 | Mix 2 | Mix 3 |
| 5 | Mix 3 | Mix 1 |
| 6 | Mix 3 | Mix 2 |

*Candida albicans was tested at 1×107 CFU/mL

Example 10: Gram-Positive Panel, Interfering Substances

Substances

Fifteen substances commonly found in blood culture specimens or as medications commonly used to treat the skin or blood infections which could potentially interfere with the BCID-GP Panel were individually evaluated. Each potentially interfering substance was spiked into negative sample matrix at a medically relevant concentration. Eight organisms representing 13 targets over a broad range of pathogens on the BCID-GP panel were combined in two mixes to achieve a final concentration of 10×LoD each and run in triplicate. No substances tested were found to inhibit the BCID-GP Panel at the concentrations listed in Table 16. The organisms in the test panel and the interfering substances are summarized in Tables 16 and 17, respectively.

TABLE 16

Potentially Interfering Substances: Gram-Positive Organism List

| Mix | Target(s) | Organism | Strain | Concentration |
|---|---|---|---|---|
| 1 | Enterococcus faecium/ vanA | Enterococcus faecium (vanA+) | ATCC BAA-2317 | $1 \times 10^7$ CFU/mL |
|  | Klebsiella pneumoniae | Klebsiella pneumoniae | ATCC 51503 | $1 \times 10^7$ CFU/mL |
|  | Candida albicans | Candida albicans | ATCC 24433 | $1 \times 10^7$ CFU/mL |
|  | Staphylococcus aureus/ mecA | Staphylococcus aureus (mecA+) | NRS 70 | $1 \times 10^6$ CFU/mL |
| 2 | Enterococcus faecalis/ vanB | Enterococcus fizecalis (vanB+) | ATCC 51575 | $1 \times 10^7$ CFU/mL |
|  | Streptococcus pneumoniae | Streptococcus pneumoniae | ATCC BAA-475 | $1 \times 10^6$ CFU/mL |
|  | Lactobacillus | Lactobacillus casei | ATCC 334 | $1 \times 10^6$ CFU/mL |
|  | Staphylococcus epidermidis | Staphylococcus epidermidis | ATCC 49134 | $1 \times 10^6$ CFU/mL |

TABLE 17

Potentially Interfering Substances: Substance List

|  | Testing Concentration |
|---|---|
| Endogenous Substances |  |
| Bilirubin | 20 mg/dL |
| Hemoglobin | 14 g/L |
| Human Genomic DNA | $6.0 \times 10^4$ copies/mL |
| Triglycerides | 3000 mg/dL |
| γ-globulin | 0.75 g/dL |
| Exogenous Substances |  |
| Heparin | 0.4 U/mL |
| Amoxicillin/Clavulanate | 7.5 ug/mL |
| Amphotericin B | 2.0 mg/L |
| Ceftriaxone | 0.152 mg/mL |
| Ciprofloxacin | 7.27 mg/L |
| Fluconazole | 15.6 mg/L |
| Gentamicin sulfate | 0.01 mg/mL |
| Imipenem | 0.083 mg/mL |
| Tetracycline | 5 mg/L |
| Vancomycin | 15 mg/L |

Bottle Types

The potential inhibitory effect of various blood culture bottles were evaluated as part of the interfering substance study. A diverse mix of four of organisms that represent eight targets on the BCID-GP panel, was spiked into sample matrix at a concentration of 10×LoD each based on the analytically determined limit of detection of the species. Thirteen types of blood culture bottles were tested in duplicate for each bottle type. One replicate of each bottle type was inoculated with negative blood only as a negative control. The organisms and bottle types tested are summarized in Table 18 and Table 19, respectively.

All bottle types tested were shown to be compatible with the BCID-GP Panel. None of the bottle types tested were found to inhibit the BCID-GP Panel.

TABLE 18

Potentially Interfering Substances: Bottle Type Gram-Positive Organism List

| Target(s) Evaluated | Organism | Strain | Concentration |
|---|---|---|---|
| Enterococcus Enterococcus faecium vanA | Enterococcus faecium (vanA+) | ATCC BAA-2317 | $1 \times 10^7$ CFU/mL |
| Staphylococcus aureus mecA | Staphylococcus aureus (mecA+) | NRS 70 | $1 \times 10^6$ CFU/mL |
| Klebsiella pneumoniae | Klebsiella pneumoniae | ATCC 51503 | $1 \times 10^7$ CFU/mL |
| Candida albicans | Candida albicans | ATCC 24433 | $1 \times 10^7$ CFU/mL |

TABLE 19

Potentially Interfering Substances: Bottle Types

| Bottle Brand | Bottle Type |
|---|---|
| BACTEC | Plus Aerobic/F |
| BACTEC | Standard/10 Aerobic/F |
| BACTEC | Standard Anaerobic/F |
| BACTEC | Plus Anaerobic/F |
| BACTEC | Pediatric Plus |
| BACTEC | Lytic/10 Anaerobic/F |
| BacT/ALERT | SA Standard Aerobic |
| BacT/ALERT | SN Standard Anaerobic |
| BacT/ALERT | FA Plus |
| BacT/ALERT | FN Plus |
| BacT/ALERT | PF Plus |
| VersaTREK | REDOX 1 EZ Draw Aerobic |
| VersaTREK | REDOX 2 EZ Draw Anaerobic |

Example 11, Gram-Negative Blood Culture Contamination

False positives were also observed in the gram-negative panel. As in Example, 1 above, negative blood matrices (no sample, no blood) listed in Table 20 were screened for contaminants. The rubber sealer of each blood culture bottle was cleaned with ethanol before puncturing it with a needle. 75 uL from each bottle was aspirated. sLRM was performed (BB sample, add 300 uL lysis buffer, 500 uL binding buffer-wait 2 min, and wash with 150 uL wash buffer). Take the washed beads and perform S2A run using 100% beads.

TABLE 20

| Brand | Blood Culture Bottle Types |
|---|---|
| BACTEC | Plus Aerobic/F |
| BACTEC | Standard/10 Aerobic/F |
| BACTEC | Standard Anaerobic/F |
| BACTEC | Plus Anaerobic/F |
| BACTEC | Pediatric Plus |
| BACTEC | Lytic/10 Anaerobic/F |
| BacT/ALERT | SN Standard Anaerobic |
| BacT/ALERT | FA Plus |
| BacT/ALERT | FN Plus |
| BacT/ALERT | PF Plus |
| VersaTREK | REDOX 1 EZ Draw Aerobic |
| VersaTREK | REDOX 2 EZ Draw Anaerobic |

The following organisms were detected as false positives: Stenotrophomonas maltophilia, Klebsiella oxytoca, OXA (OXA-23 and OXA-48), Pseudomonas aeruginosa, Pan Gram-Positive, Enterobacter cloacae/hormaechei, Pan Candida, Fusobacterium nucleatum, Escherichia coli, Serratia, Neisseria meningitides, Citrobacter, Morganella morganii, Klebsiella penumoniae, Proteus mirabilis, Proteus, Haemophilus influenza, Acinetobater baumannii. FIG. 16 shows representative data for the false positives, Proteus mirabilis (FIG. 16a), Proteus (FIG. 16b).

When PCR cycling was reduced from 40 to 30 or 35, no false positives were detected.

TABLE 21

BCID-GN reduction in PCR cycle eliminates false positives

| | 40 Cycles | Reduced Cycles |
|---|---|---|
| Stenotrophomonas maltophilia | Detected | Not detected at 35 cycles[1] |
| OXA-23 | Detected | Not detected at 35 cycles[2] |
| OXA-48 | Detected | Not detected at 30 cycles[3] |
| Pan Gram-Positive (7 assays) | Detected | Not detected at 30 or 35 cycles, some threshold[4] |
| Pan Candida | Detected | Not detected at 35 cycles |
| Escherichia coli | Detected | Not detected at 30 cycles[3] |
| Neisseria meningitides | Detected | Not detected at 30 cycles[7] |
| Morganella morganii | Detected | Not detected at 30 cycles[3] |
| Klebsiella penumoniae | Detected | Not detected at 30 cycles[3] |
| Haemophilus influenza | Detected | Not detected at 30 cycles[3] |
| Klebsiella oxytoca | Detected | Not detected at 30 cycles[3] |
| Pseudomonas aeruginosa | Detected | Not detected at 30 cycles[3] |
| Enterobacter cloacae/hormaechei | Detected | Not detected at 30 cycles[3] |
| Fusobacterium nitcleatum | Detected | Not detected at 30 cycles[3] |
| Serratia | Detected | Not detected at 30 cycles[3] |
| Citrobacter | Detected | Not detected at 30 cycles[3] |
| Proteus | Detected | Not detected at 30 cycles[3] |
| Proteus mirabilis | Detected | Not detected at 30 eyeles[5] |
| Acinetobater baumannii | Detected | Not detected at 30 cycles[6] |

[1]30 nA boundary set point for target
[2]50 nA boundary set point for target
[3]20 nA boundary set point for target
[4]Pan Gram-Positive, Enterococcus faecalis (10 nA); Pan Gram-Positive Bacillus (40 nA); Pan Gram-Positive Streptococcus anginosus (70 nA); Pan Gram-Positive Enterococcus (15 nA); Pan Gram-PositiveStrep_Staph (70 nA) boundary set point for target
[5]25 nA boundary set point for target
[6]10 nA boundary set point for target
[7]70 nA boundary set point for target FIG. 17 shows representative data for the BCID-GN assay with reduced PCR cycling (cycling as indicated in FIG. 18) showing no false positives were detected. Specifically, negative (no blood or bacterial targets) BacT/ALERT bottles were tested (~30 replicates) and the graph in FIG. 17 shows only control signals; no contamination.

Example 12: Gram-Negative Panel, Limit of Detection (Analytical Sensitivity)

The BCID-GN Multiplex primer pool and PCR cycles are shown in FIG. 18. Each of the 8 PCR drops contains an internal control S. pombe is the control target in PCR drops 1-4 (35-cycle PCR) Synthetic Control 1 (SC1) is the control target in PCR drops 5-8 (30-cycle PCR).

The PCR cycling conditions are as follows:

TABLE 22

BCID-GN PCR Cycling

| | Denature | Anneal/Extend | Cycle No. |
|---|---|---|---|
| Hot Start | 30 sec. | | |
| Step 1 | 3 sec. | 27 sec. | 1-10 |
| Step 2 | 3 sec. | 42 sec. | 11-30 or 11-35 |

This primer pool and PCR cycling are used for Examples 12-15. The BCID-GN cartridge layout is shown in FIG. 19 and was also used in Examples 12-15.

The limit of detection (LoD), or analytical sensitivity, was identified and verified for each assay on the BCID-GN Panel using quantified reference strains. Serial dilutions were prepared in simulated blood culture sample matrix which is defined as the matrix from a negative blood culture bottle mixed with whole blood and EDTA in the same ratio as the manufacturer recommends for blood culture. One or more organisms per target were tested, with at least 20 replicates per organism tested. The limit of detection was defined as the lowest concentration of each target that is detected >95% of the time. The confirmed LoD for each BCID-GN Panel organism is shown in Table 23.

TABLE 23

LoD Results Summary

| Target | Organism | Strain | LoD Concentration |
|---|---|---|---|
| Acinetobacter baumannii | Acinetobacter baumannii (OXA-23+) | NCTC 13421 | $1 \times 10^6$ CFU/mL |
| Bacteroides fragilis | Bacteroides fragilis | ATCC 43860 | $1 \times 10^4$ CFU/mL |
| Citrobacter koseri | Citrobacter koseri | ATCC 27156 | $1 \times 10^6$ CFU/mL |
| Cronobacter sakazakii | Cronobacter sakazakii | ATCC 29004 | $1 \times 10^6$ CFU/mL |
| Enterobacter non-cloacae complex | Enterobacter aerogenes (OXA-48+) | CDC #0074 | $1 \times 10^5$ CFU/mL |
| | Enterobacter amnigenus | ATCC 33072 | $1 \times 10^6$ CFU/mL |
| Enterobacter cloacae complex | Enterobacter asburiae | ATCC 35957 | $1 \times 10^6$ CFU/mL |
| | Enterobacter cloacae (VIM+) | CDC #0154 | $1 \times 10^6$ CFU/mL |
| Escherichia coli | Escherichia coli (CTX-M+) | NCTC 13441 | $1 \times 10^6$ CFU/mL |
| Fusobacterium necrophorum | Fusobacterium necrophorum | ATCC 51357 | $1 \times 10^7$ CFU/mL |
| Fusobacterium nucleatum | Fusobacterium nucleatum | ATCC 25586 | $1 \times 10^6$ CFU/mL |
| Haemophilus Influenzae | Haemophilus Influenzae | ATCC 19418 | $1 \times 10^6$ CFU/mL |
| Klebsiella oxytoca | Klebsiella oxytoca | ATCC 8724 | $1 \times 10^7$ CFU/mL |
| Klebsiella pneumoniae | Klebsiella pneumoniae | ATCC 9436 | $1 \times 10^6$ CFU/mL |
| Morganella morganii | Morganella morganii (KPC+) | CDC #0133 | $1 \times 10^6$ CFU/mL |

TABLE 23-continued

LoD Results Summary

| Target | Organism | Strain | LoD Concentration |
|---|---|---|---|
| Neisseria meningitidis | Neisseria meningitidis | ATCC 13102 | $1 \times 10^7$ CFU/mL |
| Proteus mirabilis | Proteus mirabilis (NDM+) | CDC #0159 | $1 \times 10^6$ CFU/mL |
| Proteus | Proteus vulgaris | ATCC 6896 | $1 \times 10^6$ CFU/mL |
| Pseudomonas aeruginosa | Pseudomonas aeruginosa (IMP+) | CDC #0103 | $1 \times 10^7$ CFU/mL |
| Salmonella | Salmonella bongori | ATCC 43975 | $1 \times 10^5$ CFU/mL |
| Serratia marcescens | Serratia marcescens | ATCC 14041 | $1 \times 10^6$ CFU/mL |
| Serratia | Serratia plymuthica | ATCC 53858 | $1 \times 10^7$ CFU/mL |
| Stenotrophomonas maltophilia | Stenotrophomonas maltophilia | ATCC 17666 | $1 \times 10^6$ CFU/mL |
| CTX-M | Escherichia coli (CTX-M+) | NCTC 13441 | $1 \times 10^4$ CFU/mL |
| IMP | Pseudomonas aeruginosa (IMP+) | CDC #0103 | $1 \times 10^5$ CFU/mL |
| KPC | Morganella morganii (KPC+) | CDC #0133 | $1 \times 10^5$ CFU/mL |
| NDM | Proteus mirabilis (NDM+) | CDC #0159 | $1 \times 10^5$ CFU/mL |
| OXA | Acinetobacter baumannii (OXA-23+) | NCTC 13421 | $1 \times 10^5$ CFU/mL |
| OXA | Enterobacter aerogenes (OXA-48+) | CDC #0074 | $1 \times 10^6$ CFU/mL |
| VIM | Enterobacter cloacae (VIM+) | CDC #0154 | $1 \times 10^5$ CFU/mL |
| Pan Candida | Candida albicans | ATCC 10231 | $1 \times 10^5$ CFU/mL |
|  | Candida glabrata | ATCC 15126 | $1 \times 10^5$ CFU/mL |
| Pan Gram-Positive | Bacillus subtilis | ATCC 21008 | $1 \times 10^5$ CFU/mL |
|  | Enterococcus faecium | ATCC 31282 | $1 \times 10^7$ CFU/mL |
|  | Staphylococcus aureus | ATCC BAA-2313 | $1 \times 10^5$ CFU/mL |
|  | Streptococcus agalactiae | ATCC 13813 | $1 \times 10^7$ CFU/mL |

Example 13: Gram-Negative Panel, Analytical Reactivity (Inclusivity and Exclusivity)

Analytical Reactivity (Inclusivity)

A panel of 178 strains/isolates representing the genetic, temporal and geographic diversity of each target on the BCID-GN Panel was evaluated to demonstrate analytical reactivity. Each bacterial strain was tested in triplicate at $1\times10^8$ CFU/mL while each fungus was tested at $1\times10^6$ CFU/mL in simulated sample matrix.

All of the 178 strains/isolates tested for inclusivity were detected by the BCID-GN Panel. Results of analytical reactivity are shown in Table 24.

Analytical Reactivity (Exclusivity)

Cross-reactivity of on-panel analytes was evaluated using data generated from the Analytical Reactivity study. Cross-reactivity of off-panel organisms was evaluated by testing a 44 member panel including three antibiotic resistance markers. Bacterial targets were tested at a concentration of $\geq 1\times10^9$ CFU/mL while fungi were tested at a concentration of $\geq 1\times10^7$ CFU/mL. If the desired final concentration could not be achieved a 2 fold-dilution of the stock organism was used. Table 24 summarizes the results of the on-panel organism strains tested. Each on-panel strain was tested in triplicate. Table 25 summarizes the results of the off-panel fungal and bacterial strains tested. No cross-reactivity was observed for any of the off nor on-panel organisms with any of the assays with a few exceptions. Shigella cross-reacts with Escherichia coli due to complete sequence homology as was expected based on the bioinformatic analysis. Escherichia hermanii may cross-react with at Enterobacter non-cloacae complex at $>1\times10^5$ CFU/mL and with Serratia at $>1\times10^6$ CFU/mL. Acinetobacter anitratus may cross-react with Acinetobacter baumannii at $>1\times10^4$ CFU/mL.

TABLE 24

Analytical Reactivity (Inclusivity and exclusivity) Results

| Target | Organism | Strain | Percent Detection | Highest Concentration Tested | Cross-Reactivity Results |
|---|---|---|---|---|---|
| Acinetobacter baumannii | Acinetobacter baumannii | ATCC BAA-1605 | 100% | $1 \times 10^8$ CFU/mL | Not observed |
|  |  | CDC #0033 | 100% | $1 \times 10^8$ CFU/mL | Not observed |
|  |  | NCTC 13421 | 100% | $1 \times 10^8$ CFU/mL | Not observed |
|  |  | NCTC 13424 | 100% | $1 \times 10^8$ CFU/mL | Not observed |
|  |  | NCTC 13304 | 100% | $1 \times 10^8$ CFU/mL | Not observed |
|  |  | NCTC 13301 | 100% | $1 \times 10^8$ CFU/mL | Not observed |
|  |  | ATCC BAA-2093 | 100% | $1 \times 10^8$ CFU/mL | Not observed |
|  |  | NCIMB 12457 | 100% | $1 \times 10^8$ CFU/mL | Not observed |

TABLE 24-continued

Analytical Reactivity (Inclusivity and exclusivity) Results

| Target | Organism | Strain | Percent Detection | Highest Concentration Tested | Cross-Reactivity Results |
|---|---|---|---|---|---|
| *Bacteroides fragilis* | *Bacteroides fragilis* | ATCC 9343 | 100% | $1 \times 10^8$ CFU/mL | Not observed |
| | | ATCC 25285 | 100% | $1 \times 10^8$ CFU/mL | Not observed |
| | | ATCC 700786 | 100% | $1 \times 10^8$ CFU/mL | Not observed |
| *Citrobacter* | *Citrobacter braakii* | ATCC 43162 | 100% | $1 \times 10^8$ CFU/mL | Not observed |
| | *Citrobacter freundii* | ATCC 8090 | 100% | $1 \times 10^8$ CFU/mL | Not observed |
| | | CDC #0116 | 100% | $1 \times 10^8$ CFU/mL | Not observed |
| | | NCTC 8581 | 100% | $1 \times 10^8$ CFU/mL | Not observed |
| | | JMI 2047 | 100% | $1 \times 10^8$ CFU/mL | Not observed |
| | *Citrobacter koseri* | ATCC 29936 | 100% | $1 \times 10^8$ CFU/mL | Not observed |
| | | ATCC 25409 | 100% | $1 \times 10^8$ CFU/mL | Not observed |
| | | ATCC 29225 | 100% | $1 \times 10^8$ CFU/mL | Not observed |
| | *Citrobacter youngae* | ATCC 29935 | 100% | $1 \times 10^8$ CFU/mL | Not observed |
| | *Citrobacter species* | CDC #0157 | 100% | $1 \times 10^8$ CFU/mL | Not observed |
| *Cronobacter sakazakii* | *Cronobacter sakazakii* | ATCC 29544 | 100% | $1 \times 10^8$ CFU/mL | Not observed |
| *Enterobacter cloacae* complex | *Enterobacter asburiae* | ATCC 35957 | 100% | $1 \times 10^8$ CFU/mL | Not observed |
| | | ATCC 35954 | 100% | $1 \times 10^8$ CFU/mL | Not observed |
| | *Enterobacter cloacae* | NCTC 13464 | 100% | $1 \times 10^8$ CFU/mL | Not observed |
| | | CDC #0163 | 100% | $1 \times 10^8$ CFU/mL | Not observed |
| | | ATCC 35030 | 100% | $1 \times 10^8$ CFU/mL | Not observed |
| | *Enterobacter hormaechei* | ATCC 49163 | 100% | $1 \times 10^8$ CFU/mL | Not observed |
| | | ATCC 700323 | 100% | $1 \times 10^8$ CFU/mL | Not observed |
| | | ATCC BAA-2082 | 100% | $1 \times 10^8$ CFU/mL | Not observed |
| *Enterobacter* non-*cloacae* complex | *Enterobacter aerogenes* | ATCC 13048 | 100% | $1 \times 10^8$ CFU/mL | Not observed |
| | | ATCC 51697 | 100% | $1 \times 10^8$ CFU/mL | Not observed |
| | | ATCC 29010 | 100% | $1 \times 10^8$ CFU/mL | Not observed |
| | *Enterobacter amnigenus* | ATCC 51816 | 100% | $1 \times 10^8$ CFU/mL | Not observed |
| | | ATCC 33731 | 100% | $1 \times 10^8$ CFU/mL | Not observed |
| | *Enterobacter gergoviae* | ATCC 33426 | 100% | $1 \times 10^8$ CFU/mL | Not observed |
| *Escherichia coli* | *Escherichia coli* | NCTC 13353 | 100% | $1 \times 10^8$ CFU/mL | Not observed |
| | | NCTC 13400 | 100% | $1 \times 10^8$ CFU/mL | Not observed |
| | | NCTC 13452 | 100% | $1 \times 10^8$ CFU/mL | Not observed |
| | | CDC #0118 | 100% | $1 \times 10^8$ CFU/mL | Not observed |
| | | CDC #0137 | 100% | $1 \times 10^8$ CFU/mL | Not observed |
| | | CDC #0150 | 100% | $1 \times 10^8$ CFU/mL | Not observed |
| | | ATCC BAA-2340 | 100% | $1 \times 10^8$ CFU/mL | Not observed |
| | | LMC_DR00012 | 100% | $1 \times 10^8$ CFU/mL | Not observed |
| | | ATCC 4157 | 100% | $1 \times 10^8$ CFU/mL | Not observed |

TABLE 24-continued

Analytical Reactivity (Inclusivity and exclusivity) Results

| Target | Organism | Strain | Percent Detection | Highest Concentration Tested | Cross-Reactivity Results |
|---|---|---|---|---|---|
| | | ATCC 51446 | 100% | $1 \times 10^8$ CFU/mL | Not observed |
| | | ATCC 53498 | 100% | $1 \times 10^8$ CFU/mL | Not observed |
| | | ATCC 700728 | 100% | $1 \times 10^8$ CFU/mL | Not observed |
| | | ATCC 8545 | 100% | $1 \times 10^8$ CFU/mL | Not observed |
| | | ATCC 8620 | 100% | $1 \times 10^8$ CFU/mL | Not observed |
| | | ATCC9637 | 100% | $1 \times 10^8$ CFU/mL | Not observed |
| | | ATCC BAA-196 | 100% | $1 \times 10^8$ CFU/mL | Not observed |
| | | ATCC BAA-197 | 100% | $1 \times 10^8$ CFU/mL | Not observed |
| | | ATCC BAA-198 | 100% | $1 \times 10^8$ CFU/mL | Not observed |
| | | ATCC BAA-199 | 100% | $1 \times 10^8$ CFU/mL | Not observed |
| | | ATCC BAA-202 | 100% | $1 \times 10^8$ CFU/mL | Not observed |
| | | ATCC BAA-203 | 100% | $1 \times 10^8$ CFU/mL | Not observed |
| | | ATCC BAA-204 | 100% | $1 \times 10^8$ CFU/mL | Not observed |
| | | ATCC BAA-201 | 100% | $1 \times 10^8$ CFU/mL | Not observed |
| | | NCTC 13462 | 100% | $1 \times 10^8$ CFU/mL | Not observed |
| | | NCTC 13463 | 100% | $1 \times 10^8$ CFU/mL | Not observed |
| | | CDC #0086 | 100% | $1 \times 10^8$ CFU/mL | Not observed |
| | | NCTC 13450 | 100% | $1 \times 10^8$ CFU/mL | Not observed |
| | | NCTC 13476 | 100% | $1 \times 10^8$ CFU/mL | Not observed |
| | | ATCC 13353 | 100% | $1 \times 10^8$ CFU/mL | Not observed |
| | | LMC_24309 4647 | 100% | $1 \times 10^8$ CFU/mL | Not observed |
| Fusobacterium necrophorum | Fusobacterium necrophorum | ATCC 27852 | 100% | $1 \times 10^8$ CFU/mL | Not observed |
| | | NCTC 10575 | 100% | $1 \times 10^8$ CFU/mL | Not observed |
| Fusobacterium nucleatum | Fusobacterium nucleatum | ATCC 31647 | 100% | $1 \times 10^8$ CFU/mL | Not observed |
| | | ATCC 23726 | 100% | $1 \times 10^8$ CFU/mL | Not observed |
| Haemophilus influenzae | Haemophilus influenzae | ATCC 9332 | 100% | $1 \times 10^8$ CFU/mL | Not observed |
| | | NCTC 8472 | 100% | $1 \times 10^8$ CFU/mL | Not observed |
| | | ATCC 9833 | 100% | $1 \times 10^8$ CFU/mL | Not observed |
| Klebsiella oxytoca | Klebsiella oxytoca | ATCC 13182 | 100% | $1 \times 10^8$ CFU/mL | Not observed |
| | | ATCC 43165 | 100% | $1 \times 10^8$ CFU/mL | Not observed |
| | | ATCC 43863 | 100% | $1 \times 10^8$ CFU/mL | Not observed |
| | | ATCC 43086 | 100% | $1 \times 10^8$ CFU/mL | Not observed |
| Klebsiella pneumoniae | Klebsiella pneumoniae | CDC #0112 | 100% | $1 \times 10^8$ CFU/mL | Not observed |
| | | CDC #0113 | 100% | $1 \times 10^8$ CFU/mL | Not observed |
| | | CDC #0125 | 100% | $1 \times 10^8$ CFU/mL | Not observed |
| | | ATCC BAA-1705 | 100% | $1 \times 10^8$ CFU/mL | Not observed |
| | | NCTC 13443 | 100% | $1 \times 10^8$ CFU/mL | Not observed |

TABLE 24-continued

Analytical Reactivity (Inclusivity and exclusivity) Results

| Target | Organism | Strain | Percent Detection | Highest Concentration Tested | Cross-Reactivity Results |
|---|---|---|---|---|---|
| | | CDC #0140 | 100% | $1 \times 10^8$ CFU/mL | Not observed |
| | | CDC #0141 | 100% | $1 \times 10^8$ CFU/mL | Not observed |
| | | NCTC 13440 | 100% | $1 \times 10^8$ CFU/mL | Not observed |
| | | NCTC 13439 | 100% | $1 \times 10^8$ CFU/mL | Not observed |
| | | IMH-C4171868 | 100% | $1 \times 10^8$ CFU/mL | Not observed |
| | | IMH-C2261309 | 100% | $1 \times 10^8$ CFU/mL | Not observed |
| | | IMH-C3020782 | 100% | $1 \times 10^8$ CFU/mL | Not observed |
| | | IMH-C2260742 | 100% | $1 \times 10^8$ CFU/mL | Not observed |
| | | IMH-C4151728 | 100% | $1 \times 10^8$ CFU/mL | Not observed |
| | | ATCC BAA-1706 | 100% | $1 \times 10^8$ CFU/mL | Not observed |
| | | CDC #0075 | 100% | $1 \times 10^8$ CFU/mL | Not observed |
| | | CDC #0142 | 100% | $1 \times 10^8$ CFU/mL | Not observed |
| | | CDC #0135 | 100% | $1 \times 10^8$ CFU/mL | Not observed |
| | | CDC #0153 | 100% | $1 \times 10^8$ CFU/mL | Not observed |
| | | CDC #0160 | 100% | $1 \times 10^8$ CFU/mL | Not observed |
| Morganella morganii | Morganella morganii | CDC #0057 | 100% | $1 \times 10^8$ CFU/mL | Not observed |
| | | GM148-209 | 100% | $1 \times 10^8$ CFU/mL | Not observed |
| | | ATCC 25829 | 100% | $1 \times 10^8$ CFU/mL | Not observed |
| Neisseria meningitidis | Neisseria meningitidis | NCTC 10026 | 100% | $1 \times 10^8$ CFU/mL | Not observed |
| | | ATCC 13077 | 100% | $1 \times 10^8$ CFU/mL | Not observed |
| | | ATCC 35561 | 100% | $1 \times 10^8$ CFU/mL | Not observed |
| Proteus/ Proteus mirabilis | Proteus mirabilis | CDC #0155 | 100% | $1 \times 10^8$ CFU/mL | Not observed |
| | | ATCC 12453 | 100% | $1 \times 10^8$ CFU/mL | Not observed |
| | | ATCC 43071 | 100% | $1 \times 10^8$ CFU/mL | Not observed |
| Proteus | Proteus vulgaris | ATCC 8427 | 100% | $1 \times 10^8$ CFU/mL | Not observed |
| | | NCTC 4636 | 100% | $1 \times 10^8$ CFU/mL | Not observed |
| | | ATCC 49132 | 100% | $1 \times 10^8$ CFU/mL | Not observed |
| Pseudomonas aeruginosa | Pseudomonas aeruginosa | CDC #0090 | 100% | $1 \times 10^8$ CFU/mL | Not observed |
| | | CDC #0100 | 100% | $1 \times 10^8$ CFU/mL | Not observed |
| | | CDC #0054 | 100% | $1 \times 10^8$ CFU/mL | Not observed |
| | | CDC #0092 | 100% | $1 \times 10^8$ CFU/mL | Not observed |
| | | CDC #0103 | 100% | $1 \times 10^8$ CFU/mL | Not observed |
| | | NCTC 13437 | 100% | $1 \times 10^8$ CFU/mL | Not observed |

TABLE 24-continued

Analytical Reactivity (Inclusivity and exclusivity) Results

| Target | Organism | Strain | Percent Detection | Highest Concentration Tested | Cross-Reactivity Results |
|---|---|---|---|---|---|
| *Salmonella* | *Salmonella enterica* serovar Houtenae | ATCC 29834 | 100% | $1 \times 10^8$ CFU/mL | Not observed |
| | *Salmonella enterica* serovar Indica | ATCC BAA-1578 | 100% | $1 \times 10^8$ CFU/mL | Not observed |
| | *Salmonella enterica* serovar Javiana | ATCC 10721 | 100% | $1 \times 10^8$ CFU/mL | Not observed |
| | *Salmonella enterica* serovar Oranienburg | ATCC 9239 | 100% | $1 \times 10^8$ CFU/mL | Not observed |
| | *Salmonella enterica* serovar Saintpaul | ATCC 9712 | 100% | $1 \times 10^8$ CFU/mL | Not observed |
| | *Salmonella enterica* serovar Braenderup | ATCC 700136 | 100% | $1 \times 10^8$ CFU/mL | Not observed |
| | *Salmonella enterica* serovar Enteritidis | ATCC BAA-708 | 100% | $1 \times 10^8$ CFU/mL | Not observed |
| | *Salmonella enterica* serovar Thompson | ATCC 8391 | 100% | $1 \times 10^8$ CFU/mL | Not observed |
| | *Salmonella enterica* serovar Bareilly | ATCC 9115 | 100% | $1 \times 10^8$ CFU/mL | Not observed |
| | *Salmonella enterica* serovar Heidelberg | ATCC8326 | 100% | $1 \times 10^8$ CFU/mL | Not observed |
| | *Salmonella enterica* serovar Newport | ATCC 6962 | 100% | $1 \times 10^8$ CFU/mL | Not observed |
| | *Salmonella enterica* serovar Mississippi | FSL A4-0633 | 100% | $1 \times 10^8$ CFU/mL | Not observed |
| *Serratia*/ *Serratia marcescens* | *Serratia marcescens* | ATCC 43861 | 100% | $1 \times 10^8$ CFU/mL | Not observed |
| | | ATCC 43862 | 100% | $1 \times 10^8$ CFU/mL | Not observed |
| | | ATCC 13880 | 100% | $1 \times 10^8$ CFU/mL | Not observed |
| *Serratia* | *Serratia plymuthica* | ATCC 53858 | 100% | $1 \times 10^8$ CFU/mL | Not observed |
| *Stenotrophomonas maltophilia* | *Stenotrophomonas maltophilia* | ATCC 13636 | 100% | $1 \times 10^8$ CFU/mL | Not observed |
| | | ATCC 13637 | 100% | $1 \times 10^8$ CFU/mL | Not observed |
| | | ATCC 17666 | 100% | $1 \times 10^8$ CFU/mL | Not observed |
| Pan *Candida* | *Candida albicans* | ATCC 24433 | 100% | $1 \times 10^6$ CFU/mL | Not observed |
| | *Candida parapsilosis* | ATCC 22019 | 100% | $1 \times 10^6$ CFU/mL | Not observed |
| | *Candida glabrata* | ATCC 66032 | 100% | $1 \times 10^6$ CFU/mL | Not observed |
| | *Candida krusei* | ATCC 32196 | 100% | $1 \times 10^6$ CFU/mL | Not observed |
| Pan Gram-Positive | *Bacillus cereus* | ATCC 10876 | 100% | $1 \times 10^8$ CFU/mL | Not observed |
| | *Bacillus atrophaeus* | ATCC 49337 | 100% | $1 \times 10^8$ CFU/mL | Not observed |
| | *Bacillus badius* | ATCC 14574 | 100% | $1 \times 10^8$ CFU/mL | Not observed |

TABLE 24-continued

Analytical Reactivity (Inclusivity and exclusivity) Results

| Target | Organism | Strain | Percent Detection | Highest Concentration Tested | Cross-Reactivity Results |
|---|---|---|---|---|---|
| | *Bacillus thuringiensis* | ATCC 35646 | 100% | $1 \times 10^8$ CFU/mL | Not observed |
| | *Bacillus subtilis* | ATCC 55614 | 100% | $1 \times 10^8$ CFU/mL | Not observed |
| | *Enterococcus faecalis* | ATCC 10100 | 100% | $1 \times 10^8$ CFU/mL | Not observed |
| | *Enterococcus raffinosus* | ATCC 49464 | 100% | $1 \times 10^8$ CFU/mL | Not observed |
| | *Enterococcus saccharolyticus* | ATCC 43076 | 100% | $1 \times 10^8$ CFU/mL | Not observed |
| | *Enterococcus faecium* | ATCC BAA-2317 | 100% | $1 \times 10^8$ CFU/mL | Not observed |
| | *Enterococcus casseliflavus* | ATCC 700327 | 100% | $1 \times 10^8$ CFU/mL | Not observed |
| | *Enterococcus gallinarum* | ATCC 49573 | 100% | $1 \times 10^8$ CFU/mL | Not observed |
| | *Enterococcus faecalis* | ATCC 49533 | 100% | $1 \times 10^8$ CFU/mL | Not observed |
| | *Enterococcus faecalis* | ATCC 51299 | 100% | $1 \times 10^8$ CFU/mL | Not observed |
| | *Staphylococcus aureus* | NR-46244 | 100% | $1 \times 10^8$ CFU/mL | Not observed |
| | *Staphylococcus caprae* | ATCC 51548 | 100% | $1 \times 10^8$ CFU/mL | Not observed |
| | *Staphylococcus epidermidis* | ATCC 35984 | 100% | $1 \times 10^8$ CFU/mL | Not observed |
| | *Staphylococcus haemolyticus* | ATCC 29970 | 100% | $1 \times 10^8$ CFU/mL | Not observed |
| | *Staphylococcus lentus* | ATCC 700403 | 100% | $1 \times 10^8$ CFU/mL | Not observed |
| | *Staphylococcus muscae* | ATCC 49910 | 100% | $1 \times 10^8$ CFU/mL | Not observed |
| | *Staphylococcus warneri* | ATCC 27836 | 100% | $1 \times 10^8$ CFU/mL | Not observed |
| | *Staphylococcus arlettae* | ATCC 43957 | 100% | $1 \times 10^8$ CFU/mL | Not observed |
| | *Staphylococcus carnosus* | ATCC 51365 | 100% | $1 \times 10^8$ CFU/mL | Not observed |
| | *Staphylococcus chromogenes* | ATCC 43764 | 100% | $1 \times 10^8$ CFU/mL | Not observed |
| | *Staphylococcus vitulinus* | ATCC 51699 | 100% | $1 \times 10^8$ CFU/mL | Not observed |
| | *Staphylococcus hominis* | ATCC 27844 | 100% | $1 \times 10^8$ CFU/mL | Not observed |
| | *Staphylococcus pseudintermedius* | ATCC 49444 | 100% | $1 \times 10^8$ CFU/mL | Not observed |
| | *Staphylococcus hyicus* | ATCC 11249 | 100% | $1 \times 10^8$ CFU/mL | Not observed |
| | *Staphylococcus saccharolyticus* | ATCC 14953 | 100% | $1 \times 10^8$ CFU/mL | Not observed |
| | *Streptococcus infantis* | ATCC 700779 | 100% | $1 \times 10^8$ CFU/mL | Not observed |
| | *Streptococcus parasanguinis* | ATCC 15909 | 100% | $1 \times 10^8$ CFU/mL | Not observed |
| | *Streptococcus gordonii* | ATCC 35557 | 100% | $1 \times 10^8$ CFU/mL | Not observed |
| | *Streptococcus peroris* | ATCC 700780 | 100% | $1 \times 10^8$ CFU/mL | Not observed |
| | *Streptococcus criceti* | ATCC 19642 | 100% | $1 \times 10^8$ CFU/mL | Not observed |
| | *Streptococcus equi* | ATCC 9528 | 100% | $1 \times 10^8$ CFU/mL | Not observed |
| | *Streptococcus anginosus* | ATCC 33397 | 100% | $1 \times 10^8$ CFU/mL | Not observed |
| | *Streptococcus agalactiae* | ATCC 13813 | 100% | $1 \times 10^8$ CFU/mL | Not observed |
| | *Streptococcus bovis* | ATCC 33317 | 100% | $1 \times 10^8$ CFU/mL | Not observed |
| | *Streptococcus dysgalactiae* | ATCC 35666 | 100% | $1 \times 10^8$ CFU/mL | Not observed |
| | *Streptococcus equinus* | ATCC 15351 | 100% | $1 \times 10^8$ CFU/mL | Not observed |
| | *Streptococcus infantarius* | ATCC BAA-102 | 100% | $1 \times 10^8$ CFU/mL | Not observed |

TABLE 24-continued

Analytical Reactivity (Inclusivity and exclusivity) Results

| Target | Organism | Strain | Percent Detection | Highest Concentration Tested | Cross-Reactivity Results |
|---|---|---|---|---|---|
| CTX-M | *Citrobacter freundii* (CTX-M+) | JMI 2047 | 100% | $1 \times 10^8$ CFU/mL | Not observed |
| | *Enterobacter cloacae* (CTX-M+) | NCTC 13464 | 100% | $1 \times 10^8$ CFU/mL | Not observed |
| | | CDC #0163 | 100% | $1 \times 10^8$ CFU/mL | Not observed |
| | *Escherichia coli* (CTX-M+) | NCTC 13353 | 100% | $1 \times 10^8$ CFU/mL | Not observed |
| | | NCTC 13400 | 100% | $1 \times 10^8$ CFU/mL | Not observed |
| | | NCTC 13452 | 100% | $1 \times 10^8$ CFU/mL | Not observed |
| | | NCTC 13462 | 100% | $1 \times 10^8$ CFU/mL | Not observed |
| | | NCTC 13463 | 100% | $1 \times 10^8$ CFU/mL | Not observed |
| | | CDC #0086 | 100% | $1 \times 10^8$ CFU/mL | Not observed |
| | | NCTC 13450 | 100% | $1 \times 10^8$ CFU/mL | Not observed |
| | | ATCC 13353 | 100% | $1 \times 10^8$ CFU/mL | Not observed |
| | *Klebsiella pneumoniae* (CTX-M+) | NCTC 13443 | 100% | $1 \times 10^8$ CFU/mL | Not observed |
| IMP | *Escherichia coli* (IMP+) | NCTC 13476 | 100% | $1 \times 10^8$ CFU/mL | Not observed |
| | *Pseudomonas aeruginosa* (IMP+) | CDC #0092 | 100% | $1 \times 10^8$ CFU/mL | Not observed |
| | | CDC #0103 | 100% | $1 \times 10^8$ CFU/mL | Not observed |
| KPC | *Citrobacter freundii* (KPC+) | CDC #0116 | 100% | $1 \times 10^8$ CFU/mL | Not observed |
| | *Enterobacter cloacae* (KPC+) | CDC #0163 | 100% | $1 \times 10^8$ CFU/mL | Not observed |
| | *Enterobacter hormaechei* (KPC+) | ATCC BAA-2082 | 100% | $1 \times 10^8$ CFU/mL | Not observed |
| | *Escherichia coli* (KPC+) | ATCC BAA-2340 | 100% | $1 \times 10^8$ CFU/mL | Not observed |
| | *Klebsiella pneumoniae* (KPC+) | CDC #0112 | 100% | $1 \times 10^8$ CFU/mL | Not observed |
| | | CDC #0113 | 100% | $1 \times 10^8$ CFU/mL | Not observed |
| | | CDC #0125 | 100% | $1 \times 10^8$ CFU/mL | Not observed |
| | | ATCC BAA-1705 | 100% | $1 \times 10^8$ CFU/mL | Not observed |
| | *Proteus mirabilis* (KPC+) | CDC #0155 | 100% | $1 \times 10^8$ CFU/mL | Not observed |
| | *Pseudomonas aeruginosa* (KPC+) | CDC #0090 | 100% | $1 \times 10^8$ CFU/mL | Not observed |
| NDM | *Acinetobacter baumannii* (NDM+) | CDC #0033 | 100% | $1 \times 10^8$ CFU/mL | Not observed |
| | *Citrobacter species* (NDM+) | CDC #0157 | 100% | $1 \times 10^8$ CFU/mL | Not observed |
| | *Escherichia coli* (NDM+) | CDC #0118 | 100% | $1 \times 10^8$ CFU/mL | Not observed |
| | | CDC #0137 | 100% | $1 \times 10^8$ CFU/mL | Not observed |
| | | CDC #0150 | 100% | $1 \times 10^8$ CFU/mL | Not observed |
| | *Klebsiella pneumoniae* (NDM+) | NCTC 13443 | 100% | $1 \times 10^8$ CFU/mL | Not observed |

TABLE 24-continued

Analytical Reactivity (Inclusivity and exclusivity) Results

| Target | Organism | Strain | Percent Detection | Highest Concentration Tested | Cross-Reactivity Results |
|---|---|---|---|---|---|
| | Morganella morganii (NDM+) | CDC #0057 | 100% | $1 \times 10^8$ CFU/mL | Not observed |
| | Klebsiella pneumoniae (NDM+) | CDC #0153 | 100% | $1 \times 10^8$ CFU/mL | Not observed |
| OXA | Acinetobacter baumannii (OXA+) | ATCC BAA-1605 | 100% | $1 \times 10^8$ CFU/mL | Not observed |
| | | NCTC 13421 | 100% | $1 \times 10^8$ CFU/mL | Not observed |
| | | NCTC 13424 | 100% | $1 \times 10^8$ CFU/mL | Not observed |
| | | NCTC 13304 | 100% | $1 \times 10^8$ CFU/mL | Not observed |
| | | NCTC 13301 | 100% | $1 \times 10^8$ CFU/mL | Not observed |
| | Escherichia coli (OXA+) | LMC_DR00012 | 100% | $1 \times 10^8$ CFU/mL | Not observed |
| | Klebsiella pneumoniae (OXA+) | CDC #0140 | 100% | $1 \times 10^8$ CFU/mL | Not observed |
| | | CDC #0141 | 100% | $1 \times 10^8$ CFU/mL | Not observed |
| | | CDC #0075 | 100% | $1 \times 10^8$ CFU/mL | Not observed |
| | | CDC #0142 | 100% | $1 \times 10^8$ CFU/mL | Not observed |
| | | CDC #0153 | 100% | $1 \times 10^8$ CFU/mL | Not observed |
| | | CDC #0160 | 100% | $1 \times 10^8$ CFU/mL | Not observed |
| VIM | Klebsiella pneumoniae (VIM+) | NCTC 13440 | 100% | $1 \times 10^8$ CFU/mL | Not observed |
| | | NCTC 13439 | 100% | $1 \times 10^8$ CFU/mL | Not observed |
| | Pseudomonas aeruginosa (VIM+) | CDC #0100 | 100% | $1 \times 10^8$ CFU/mL | Not observed |
| | | CDC #0054 | 100% | $1 \times 10^8$ CFU/mL | Not observed |
| | | NCTC 13437 | 100% | $1 \times 10^8$ CFU/mL | Not observed |
| | Klebsiella pneumoniae (VIM+) | CDC #0135 | 100% | $1 \times 10^8$ CFU/mL | Not observed |

TABLE 25

Cross-reactivity with Organisms Not Detected by the BCID-GN Panel (Exclusivity)

| Organism | Strain | Highest Concentration Tested | Cross-Reactivity Results |
|---|---|---|---|
| Acinetobacter haemolyticus | ATCC 19002 | $1 \times 10^9$ CFU/mL | Not observed |
| Prevotella oralis | ATCC 33269 | $1 \times 10^9$ CFU/mL | Not observed |
| Shigella boydii | ATCC 9207 | $1 \times 10^9$ CFU/mL | Escherichia coli detected |
| Shigella flexneri | ATCC 9199 | $1 \times 10^9$ CFU/mL | Escherichia coli detected |
| Neisseria sicca | ATCC 29193 | $1 \times 10^9$ CFU/mL | Not observed |
| Neisseria gonorrhoeae | ATCC 19424 | $1 \times 10^9$ CFU/mL | Not observed |
| Yersinia enterocolitica subsp. enterocolitica | ATCC 9610 | $1 \times 10^9$ CFU/mL | Not observed |
| Yersinia kristensenii | ATCC 33639 | $1 \times 10^9$ CFU/mL | Not observed |
| Bacteroides ovatus | ATCC BAA-1296 | $1 \times 10^9$ CFU/mL | Not observed |
| Haemophilus haemolyticus | ATCC 33390 | $1 \times 10^9$ CFU/mL | Not observed |
| Ralstonia insidiosa | ATCC 49129 | $1 \times 10^9$ CFU/mL | Not observed |
| Vibrio alginolyticus | ATCC 17749 | $1 \times 10^9$ CFU/mL | Not observed |
| Vibrio furnissii | NCTC 11218 | $1 \times 10^9$ CFU/mL | Not observed |
| Prevotella intermedia | ATCC 15032 | $1 \times 10^9$ CFU/mL | Not observed |
| Prevotella corporis | ATCC 33547 | $1 \times 10^9$ CFU/mL | Not observed |
| Pantoea agglomerans | ATCC 14537 | $1 \times 10^9$ CFU/mL | Not observed |
| Escherichia hermanii | ATCC 700368 | $1 \times 10^9$ CFU/mL | Enterobacter amnigenus and Serratia detected [A] |
| Acinetobacter anitratus | ATCC 49139 | $1 \times 10^9$ CFU/mL | Acinetobacter baumanii detected [B] |
| Escherichia fergusonii | ATCC 35469 | $1 \times 10^9$ CFU/mL | Not observed |
| Bacteroides merdae | ATCC 43184 | $1 \times 10^9$ CFU/mL | Not observed |
| Bacteroides distasonis (Parabacteroides) | ATCC 8503 | $1 \times 10^9$ CFU/mL | Not observed |
| Bacteroides eggerthii | ATCC 27754 | $1 \times 10^9$ CFU/mL | Not observed |

TABLE 25-continued

Cross-reactivity with Organisms Not Detected by the BCID-GN Panel (Exclusivity)

| Organism | Strain | Highest Concentration Tested | Cross-Reactivity Results |
|---|---|---|---|
| Prevotella nigrescens | ATCC 33563 | $1 \times 10^9$ CFU/mL | Not observed |
| Bordetella pertussis | ATCC 9797 | $1 \times 10^9$ CFU/mL | Not observed |
| Pseudomonas mosselii | ATCC 49838 | $1 \times 10^9$ CFU/mL | Not observed |
| Pseudomonas fluorescens | ATCC 13525 | $1 \times 10^9$ CFU/mL | Not observed |
| Neisseria flavescens | ATCC 13115 | $1 \times 10^9$ CFU/mL | Not observed |
| Pasteurella aerogenes | ATCC 27883 | $1 \times 10^9$ CFU/mL | Not observed |
| Providencia alcalifaciens | ATCC 9886 | $1 \times 10^9$ CFU/mL | Not observed |
| Escherichia coli (TEM) | CTC 13351 | $1 \times 10^9$ CFU/mL | Not observed [C] |
| Klebsiella pneumoniae (SHV) | CDC#0087 | $1 \times 10^9$ CFU/mL | Not observed [C] |
| Serratia marcescens (SME) | CDC#0091 | $1 \times 10^9$ CFU/mL | Not observed [C] |
| Lactococcus lactis | ATCC 49032 | $1 \times 10^9$ CFU/mL | Not observed |
| Lactobacillus acidophilus | ATCC 314 | $1 \times 10^9$ CFU/mL | Not observed |
| Corynebacterium renale | ATCC 19412 | $1 \times 10^9$ CFU/mL | Not observed |
| Corynebacterium jeikeium | ATCC BAA-949 | $1 \times 10^9$ CFU/mL | Not observed |
| Corynebacterium diphtheriae | ATCC 13812 | $1 \times 10^9$ CFU/mL | Not observed |
| Listeria innocua | ATCC 33090 | $1 \times 10^9$ CFU/mL | Not observed |
| Lactobacillus casei | ATCC 39392 | $1 \times 10^9$ CFU/mL | Not observed |
| Micrococcus luteus | ATCC 10240 | $1 \times 10^9$ CFU/mL | Not observed |
| Corynebacterium ulcerans | ATCC 51799 | $1 \times 10^9$ CFU/mL | Not observed |
| Candida tropicalis | ATCC 1369 | $1 \times 10^7$ CFU/mL | Not observed |
| Candida orthopsilosis | ATCC 96139 | $1 \times 10^7$ CFU/mL | Not observed |
| Trichosporon asahii | ATCC 201110 | $1 \times 10^7$ CFU/mL | Not observed |
| Prevotella intermedia | ATCC 15032 | $9 \times 10^8$ CFU/mL | Not observed |
| Prevotella corporis | ATCC 33547 | $6 \times 10^8$ CFU/mL | Not observed |
| Pseudomonas mosselii | ATCC 49838 | $1 \times 10^9$ CFU/mL | Not observed |
| Prevotella oralis | ATCC 33269 | $5 \times 10^8$ CFU/mL | Not observed |
| Bacteroides ovatus | ATCC BAA-1296 | $6 \times 10^8$ CFU/mL | Not observed |
| Haemophilus haemolyticus | ATCC 33390 | $4 \times 10^8$ CFU/mL | Not observed |
| Prevotella nigrescens | ATCC 33563 | $4 \times 10^8$ CFU/mL | Not observed |
| Lactobacillus acidophilus | ATCC 314 | $3 \times 10^8$ CFU/mL | Not observed |
| Corynebacterium diphtheriae | ATCC 13812 | $5 \times 10^8$ CFU/mL | Not observed |

[A] Enterobacter amnigenus detected at $> 1 \times 10^5$ CFU/mL, Serratia detected at $> 1 \times 10^6$ CFU/mL
[B] Acinetobacter baumanii detected at $> 1 \times 10^4$ CFU/mL
[C] Cross-reactivity was not observed for the resistance marker. The on-panel organism was detected as expected.

Example 14: Gram-Negative Panel Competitive Inhibition

Detection of more than one clinically relevant on-panel organism in a sample was evaluated with the BCID-GN Panel using nine selected organisms which were grouped into mixes of three organisms per mix in a blood culture matrix. Test case scenarios paired mixes with one mix at approximately ten times the analytically determined limit of detection for the species (10×LoD) and a second at high titer ($1\times10^8$ CFU/mL for bacterial targets and $1\times10^7$ CFU/mL for Candida albicans) and vice versa. The organism mixes and combined mixes are summarized in Table 26 and Table 27. All targets were detected in the combinations specified in Table 27. The results of co-detection testing demonstrate the ability of the BCID-GN to detect two on-panel organisms in a sample at both high and low concentrations.

TABLE 26

Detection of Co-Infections: Organism Mixes

| Organism Mix | Target(s) | Organism | Strain |
|---|---|---|---|
| 1 | Pan Candida | Candida albicans | ATCC 10231 |
| | Escherichia coli/CTX-M | Escherichia coli (CTX-M+) | NCTC 13441 |
| | Pan Gram-Positive | Staphylococcus aureus | ATCC BAA-2313 |
| 2 | Enterobacter cloacae complex/VIM | Enterobacter cloacae (VIM+) | CDC #0154 |
| | Klebsiella pneumoniae | Klebsiella pneumoniae | ATCC 9436 |
| | Serratia/Serratia marcescens | Serratia marcescens | ATCC 14041 |
| 3 | Klebsiella oxytoca | Klebsiella oxytoca | ATCC 8724 |
| | Proteus/Proteus mirabilis/NDM | Proteus mirabilis (NDM+) | CDC #0159 |
| | Pseudomonas aeruginosa | Pseudomonas aeruginosa | CDC #0103 |

TABLE 27

Detection of Co-Infections: Organism Mix Pairings

| | Combined Concentration | |
|---|---|---|
| Mix ID | 10 × LoD | $1 \times 10^8$ CFU/mL* |
| 1 | Mix 1 | Mix 2 |
| 2 | Mix 1 | Mix 3 |
| 3 | Mix 2 | Mix 1 |
| 4 | Mix 2 | Mix 3 |
| 5 | Mix 3 | Mix 1 |
| 6 | Mix 3 | Mix 2 |

*Candida albicans was tested at $1 \times 10^7$ CFU/mL.

Example 15: Interfering Substances

Substances

Fifteen substances commonly found in blood culture specimens or as medications commonly used to treat the skin or blood infections which could potentially interfere with the BCID-GN Panel were individually evaluated. Each potentially interfering substance was spiked into negative sample matrix at a medically relevant concentration. Six organisms representing 9 targets covering a broad range of pathogens on the BCID-GN Panel were spiked into negative blood matrix to achieve a final concentration of 10×LoD for each species and run in triplicate. No substances tested were found to inhibit the BCID-GN Panel at the organism concentrations listed in Table 28 and the substance concentrations listed in Table 29.

TABLE 28

Potentially Interfering Substances: Gram-Negative Organism List

| Target(s) | Organism | Strain | Concentration |
|---|---|---|---|
| Enterobacter cloacae/VIM | Enterobacter cloacae (VIM+) | CDC #0154 | $1 \times 10^7$ CFU/mL |
| Escherichia coli/CTX-M | Escherichia coli (CTX-M+) | NCTC 13441 | $1 \times 10^7$ CFU/mL |
| Klebsiella pneumoniae | Klebsiella pneumoniae | ATCC 9436 | $1 \times 10^7$ CFU/mL |
| Serratia/Serratia marcescens | Serratia marcescens | ATCC 14041 | $1 \times 10^7$ CFU/mL |
| Pan Candida | Candida glabrata | ATCC 15126 | $1 \times 10^6$ CFU/mL |

TABLE 28-continued

Potentially Interfering Substances:
Gram-Negative Organism List

| Target(s) | Organism | Strain | Concentration |
|---|---|---|---|
| Pan Gram-Positive | Staphylococcus aureus | ATCC BAA-2313 | $1 \times 10^6$ CFU/mL |

TABLE 29

Potentially Interfering Substances: Substance List

| | Testing Concentration |
|---|---|
| Endogenous Substances | |
| Bilirubin | 20 mg/dL |
| Hemoglobin | 14 g/L |
| Human Genomic DNA | $6.0 \times 10^4$ copies/mL |
| Triglycerides | 3000 mg/dL |
| γ-globulin | 0.75 g/dL |
| Exogenous Substances | |
| Heparin | 0.4 U/mL |
| Amoxicillin/Clavulanate | 7.5 ug/mL |
| Amphotericin B | 2.0 mg/L |
| Ceftriaxone | 0.152 mg/mL |
| Ciprofloxacin | 7.27 mg/L |
| Fluconazole | 15.6 mg/L |
| Gentamicin sulfate | 0.01 mg/mL |
| Imipenem | 0.083 mg/mL |
| Tetracycline | 5 mg/L |
| Vancomycin | 15 mg/L |

Bottle Types

The potential inhibitory effect of various blood culture bottles were evaluated as part of the interfering substance study. Six organisms representing 9 targets covering a broad range of pathogens on the BCID-GN Panel, were spiked into sample matrix at a concentration of 10×LoD each based on the analytically determined limit of detection of the species. Thirteen types of blood culture bottles were tested in duplicate for each bottle type. One replicate of each bottle type was inoculated with negative blood only as a negative control. The organisms and bottle types tested are summarized in Table 30 and Table 31, respectively.

All bottle types tested were shown to be compatible with the BCID-GN Panel. None of the bottle types tested were found to inhibit the BCID-GN Panel.

TABLE 30

Potentially Interfering Substances: Bottle Type Gram-Negative Organism List

| Target(s) | Organism | Strain | Concentration |
|---|---|---|---|
| Escherichia coli/CTX-M | Escherichia coli (CTX-M+) | NCTC 13441 | $1 \times 10^7$ CFU/mL |
| Enterobacter cloacae complex/VIM | Enterobacter cloacae (VIM+) | CDC #0154 | $1 \times 10^7$ CFU/mL |
| Klebsiella pneumoniae | Klebsiella pneumoniae | ATCC 9436 | $1 \times 10^7$ CFU/mL |
| Serratia/Serratia marcescens | Serratia marcescens | ATCC 14041 | $1 \times 10^7$ CFU/mL |
| Pan Candida | Candida glabrata | ATCC 15126 | $1 \times 10^6$ CFU/mL |
| Pan Gram-Positive | Staphylococcus aureus | ATCC BAA-2313 | $1 \times 10^6$ CFU/mL |

TABLE 31

Potentially Interfering Substances: Bottle Types

| Bottle Brand | Bottle Type |
|---|---|
| BACTEC | Plus Aerobic/F |
| BACTEC | Standard/10 Aerobic/F |
| BACTEC | Standard Anaerobic/F |
| BACTEC | Plus Anaerobic /F |
| BACTEC | Pediatric Plus |
| BACTEC | Lytic/10 Anaerobic/F |
| BacT/ALERT | SA Standard Aerobic |
| BacT/ALERT | SN Standard Anaerobic |
| BacT/ALERT | FA Plus |
| BacT/ALERT | FN Plus |
| BacT/ALERT | PF Plus |
| VersaTREK | REDOX 1 EZ Draw Aerobic |
| VersaTREK | REDOX 2 EZ Draw Anaerobic |

Example 16, Fungal Blood Culture Contamination

False positives were also observed in the BCID-FP panel.

Unlike for the BCID-GP and GN panels, false positives were reduced/eliminated in the BCID-FP panel by introducing mismatched primers.

Figure 20B:
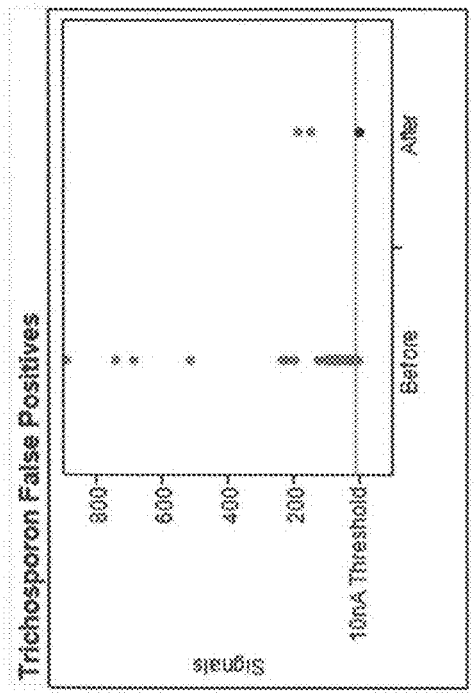
FIG. 20A and FIG. 20B: Shows the signals obtained before and after detuning, for *Rhodotorula* (FIG. 20A) and *Trichosporon* (FIG. 20B).
Figure 20A:
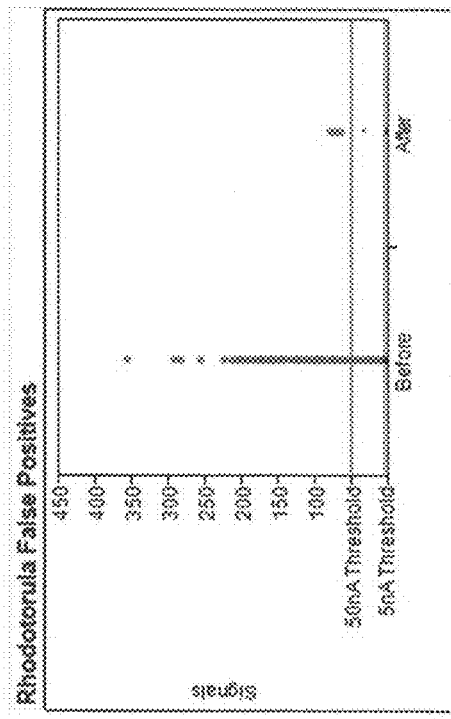

Table 32 shows the percentage of false positives obtained before mismatching and thresholding and the percentage of false positives after mismatching and thresholding. FIG. 20 shows the signals obtained before and after detuning, i.e., before and after mismatching and thresholding for two targets Rhodotorula (FIG. 20a) and Trichosporon (FIG. 20b).

TABLE 32

BCID-FP, Percentage false positives before detuning and after detuning

| Assay (threshold) | False positives before mismatch, threshold | False positives after mismatch, thresholding |
|---|---|---|
| Rhodotorula (≥50 nA) | 30/782 (3.8%) | 2/1254 (0.16%) |
| Trichosporon (≥10 nA) | 11/2042 (0.54%) | 1/1371 (0.07%) |

Example 17, Fungal Panel, Two Zone, One Target

An additional approach to overcome false positives was applied to two targets of the BCID-FP assay. Rather than changing the PCR cycle number or primer concentrations, primers to amplify a single target were placed in two multiplex primer pools. The target is amplified in two PCR lanes and is detected in two different detection zones. A positive detection call is only made when the target is detected in both detection zones. If the target is detected in one zone but not the other, a non-detection call is made. Without dual zone detection, low level contamination may trigger amplification and detection at low frequencies. With dual zone detection, which requires two amplifications and detections, the frequency of background contamination detection is reduced.

Table 33 shows the percentage of false positive before dual zone detection and after dual zone detection.

TABLE 33

BCID-FP Dual Zone detection

| Target | % False Positives Before Dual Zone | % False Positives After Dual Zone |
|---|---|---|
| C. parapsilosis | 0.4% (4/926) | 0.1% (2/1826) |
| C. tropicalis | 0.6% (8/1280) | 0.1% (2/1877) |

Table 34 shows which targets were falsely detected before detuning (primer mismatch or dual zone detection and thresholding) and after as well as the thresholding for each target.

TABLE 34

BCID-FP, Detection of false positives before detuning and after detuning

| Target Name | Before Detuning | After Detuning | Threshold (nA) |
|---|---|---|---|
| Candida auris | Not Detected | Not Detected | 5 |
| Candida albicans | Not Detected | Not Detected | 5 |
| Candida dubliniensis | Not Detected | Not Detected | 25 |
| Candida famata | Not Detected | Not Detected | 100 |
| Candida glabrata | Not Detected | Not Detected | 25 |
| Candida guilliermondii | Not Detected | Not Detected | 25 |
| Candida kefyr | Not Detected | Not Detected | 25 |
| Candida krusei | Not Detected | Not Detected | 25 |
| Candida lusitaniae | Not Detected | Not Detected | 25 |
| Candida parapsilosis[2] | Detected | Not Detected | 25 |
| Candida tropicalis[2] | Detected | Not Detected | 25 |
| Cryptococcus gattii | Not Detected | Not Detected | 25 |
| Cryptococcus neoformans var. grubii | Not Detected | Not Detected | 25 |
| Cryptococcus neoformans var. neoformans | Not Detected | Not Detected | 25 |
| Fusarium | Not Detected | Not Detected | 25 |
| Malassezia furfur | Not Detected | Not Detected | 400 |
| Rhodotorula[1] | Detected | Not Detected | 50 |
| Trichosporon[1] | Detected | Not Detected | 10 |

[1]With primer mismatch.
[2]With dual zone detection

Example 18, Fungal Panel, Limit of Detection (Analytical Sensitivity)

The BCID-FP Multiplex primer pool and PCR cycles are shown in FIG. 21. S. pombe is the control target in PCR drops 1-4 (40-cycle PCR).

The PCR cycling conditions are as follows:

TABLE 35

BCID-FP PCR cycling

| | Denature 96.3° C. | Anneal/Extend 62.5° C. | Cycle No. |
|---|---|---|---|
| Hot Start | 30 | | |
| Step 1 | 3 sec | 27 sec | 1-15 |
| Step 2 | 3 sec | 40 sec | 16-40 |

This primer pool and PCR cycling are used for Examples 18-21. The BCID-FP cartridge layout is shown in FIG. 22 and was also used in Examples 18-21 below.

The limit of detection (LoD) or analytical sensitivity was identified and verified for each fungal target on the BCID-FP Panel using quantified reference strains. Serial dilutions were prepared in simulated blood culture sample matrix (sample matrix), which is defined as the matrix from a negative blood culture bottle mixed with whole blood and EDTA in the same ratio as the manufacturer recommends for blood culture. Organisms were tested with at least 20 replicates split between two cartridge lots. The limit of detection was defined as the lowest concentration of each target that is detected >95% of the time. The confirmed LoD for each BCID-FP Panel organism is shown in Table 36.

TABLE 36

LoD Results Summary

| Target | Organism | Strain | LoD Concentration |
|---|---|---|---|
| Candida albicans | Candida albicans | ATCC 14053 | $1.0 \times 10^4$ CFU/mL |
| Candida dubliniensis | Candida dubliniensis | ATCC MYA-577 | $3.0 \times 10^4$ CFU/mL |
| Candida famata | Candida famata | CBS 767 | $3.0 \times 10^3$ CFU/mL |
| Candida glabrata | Candida glabrata | ATCC 2001 | $1.0 \times 10^4$ CFU/mL |
| Candida guilliermondii | Candida guilliermondii | ATCC 22017 | $1.0 \times 10^4$ CFU/mL |
| Candida kefyr | Candida kefyr | ATCC 4135 | $2.0 \times 10^2$ CFU/mL |
| Candida lusitaniae | Candida lusitaniae | ATCC 34449 | $1.0 \times 10^4$ CFU/mL |
| Candid krusei | Candid krusei | ATCC 22985 | $2.0 \times 10^4$ CFU/mL |
| Candida parapsilosis | Candida parapsilosis | ATCC 28475 | $3.0 \times 10^4$ CFU/mL |
| Candida tropicalis | Candida tropicalis | ATCC 13803 | $5.0 \times 10^4$ CFU/mL |
| Cryptococcus neoformans | Cryptococcus neoformans var grubii | ATCC 208821 | $3.0 \times 10^3$ CFU/mL |
| Cryptococcus gattii | Cryptococcus gattii | ATCC MYA-4877 | $1.0 \times 10^3$ CFU/mL |
| Fusarium | Fusarium verticillioides | CBS 100312 | $3.0 \times 10^7$ CFU/mL |
| Malassezia furfur | Malassezia furfur | CBS 7710 | $3.0 \times 10^4$ CFU/mL |
| Rhodotorula | Rhodotorula mucilaginosa | ATCC 4058 | $3.0 \times 10^3$ CFU/mL |
| Trichosporon | Trichosporon dermatis | ATCC 204094 | $1.0 \times 10^5$ CFU/mL |

Example 19, Fungal Panel, Analytical Reactivity (Inclusivity, Cross-Reactivity and Exclusivity)

Analytical reactivity (inclusivity) for the BCID-FP Panel was evaluated using a collection of 48 fungal isolates covering the genetic diversity of the organisms detected on the BCID-FP Panel. Negative sample matrix was spiked with the organism at a concentration of 10×LoD, with a total of 3 replicates tested for each isolate. The results of the BCID-FP Panel Analytical Reactivity (Inclusivity) Study is shown in Table 37. Cross-Reactivity and Exclusivity Cross-reactivity of on-panel analytes was evaluated using data generated from the Analytical Reactivity study. Cross-reactivity of off-panel organisms was evaluated by testing a 36 member panel, containing clinically-relevant bacteria and fungi. Bacterial targets were tested at a concentration of $\geq 1\times 10^9$ CFU/mL while fungi were tested at a concentration of $\geq 1\times 10^7$ CFU/mL whenever possible. Table 38 summarizes the results of the on-panel fungal strains tested. Each on-panel strain was tested in triplicate. Table 39 summarizes the results of the off-panel fungal and bacterial strains tested. No cross-reactivity was observed for any of the off- or on-panel organisms.

TABLE 37

Analytical Reactivity (Inclusivity, Cross-Reactivity, and Exclusivity) Results

| Organism | Strain | Concentration | Multiple of LoD Detected |
|---|---|---|---|
| Candida albicans | ATCC MYA-4441 | $1.0 \times 10^5$ CFU/mL | 10× |
| Candida albicans | ATCC 90028 | $1.0 \times 10^5$ CFU/mL | 10× |
| Candida dubliniensis | NCPF 3949 | $3.0 \times 10^5$ CFU/mL | 10× |
| Candida dubliniensis | ATCC MYA-582 | $3.0 \times 10^5$ CFU/mL | 10× |
| Candida famata | CBS 1961 | $3.0 \times 10^4$ CFU/mL | 10× |
| Candida famata | CBS 766 | $3.0 \times 10^4$ CFU/mL | 10× |
| Candida glabrata | ATCC MYA-2950 | $1.0 \times 10^5$ CFU/mL | 10× |
| Candida glabrata | ATCC 15545 | $1.0 \times 10^5$ CFU/mL | 10× |
| Candida guilliermondii | ATCC 6260 | $1.0 \times 10^5$ CFU/mL | 10× |
| Candida guilliermondii | ATCC 90197 | $1.0 \times 10^5$ CFU/mL | 10× |
| Candida kefyr | ATCC 204093 | $2.0 \times 10^3$ CFU/mL | 10× |
| Candida kefyr | ATCC 8553 | $2.0 \times 10^3$ CFU/mL | 10× |
| Candida krusei | ATCC 28870 | $2.0 \times 10^5$ CFU/mL | 10× |
| Candida krusei | ATCC 14243 | $2.0 \times 10^5$ CFU/mL | 10× |
| Candid lusitaniae | ATCC 42720 | $1.0 \times 10^5$ CFU/mL | 10× |
| Candid lusitaniae | ATCC 66035 | $1.0 \times 10^5$ CFU/mL | 10× |
| Candida parapsilosis | ATCC 28474 | $3.0 \times 10^5$ CFU/mL | 10× |
| Candida parapsilosis | ATCC 22019 | $3.0 \times 10^5$ CFU/mL | 10× |
| Candida tropicalis | ATCC 201381 | $5.0 \times 10^5$ CFU/mL | 10× |
| Candida tropicalis | ATCC 1369 | $5.0 \times 10^5$ CFU/mL | 10× |
| Cryptococcus gattii | ATCC MYA-4138 | $1.0 \times 10^4$ CFU/mL | 10× |
| Cryptococcus gattii | ATCC 4560 | $1.0 \times 10^4$ CFU/mL | 10× |
| Cryptococcus neoformans | ATCC MYA-565 | $3.0 \times 10^4$ CFU/mL | 10× |
| Cryptococcus neoformans | ATCC 14116 | $3.0 \times 10^4$ CFU/mL | 10× |
| Fusarium oxysporum | CBS 116611 | $3.0 \times 10^5$ CFU/mL | 10× |
| Fusarium sacchari | CBS 119828 | $3.0 \times 10^5$ CFU/mL | 10× |
| Malassezia furfur | ATCC 14521 | $3.0 \times 10^5$ CFU/mL | 10× |
| Malassezia furfur | ATCC 44345 | $3.0 \times 10^5$ CFU/mL | 10× |
| Rhodotorula mucilaginosa | ATCC 4058 | $3.0 \times 10^4$ CFU/mL | 10× |
| Rhodotorula glutinis | ATCC 96365 | $3.0 \times 10^4$ CFU/mL | 10× |
| Trichosporon asahii | ATCC 201110 | $1.0 \times 10^6$ CFU/mL | 10× |
| Trichosporon asteroides | ATCC 90043 | $1.0 \times 10^6$ CFU/mL | 10× |

TABLE 38

Cross-reactivity with BCID-FP Panel On-Panel Organisms

| Organism | Strain | Highest Concentration Tested | Cross-Reactivity Results |
|---|---|---|---|
| Candida albicans | ATCC 14053 | $1.0 \times 10^7$ CFU/mL | Not observed |
| Candida dubliniensis | ATCC MYA-577 | $1.0 \times 10^7$ CFU/mL | Not observed |
| Candida dubliniensis | ATCC MYA-578 | $1.0 \times 10^7$ CFU/mL | Not observed |
| Candida dubliniensis | ATCC MYA-582 | $1.0 \times 10^7$ CFU/mL | Not observed |
| Candida famata | CBS 767 | $1.0 \times 10^7$ CFU/mL | Not observed |
| Candida glabrata | ATCC 2001 | $1.0 \times 10^7$ CFU/mL | Not observed |
| Candida guilliermondii | ATCC 22017 | $1.0 \times 10^7$ CFU/mL | Not observed |
| Candida kefyr | ATCC 4135 | $1.0 \times 10^7$ CFU/mL | Not observed |
| Candida lusitaniae | ATCC 34449 | $1.0 \times 10^7$ CFU/mL | Not observed |
| Candid krusei | ATCC 22985 | $1.0 \times 10^7$ CFU/mL | Not observed |
| Candida parapsilosis | ATCC 28475 | $1.0 \times 10^7$ CFU/mL | Not observed |
| Candida tropicalis | ATCC 13803 | $1.0 \times 10^7$ CFU/mL | Not observed |
| Cryptococcus gattii | ATCC MYA-4877 | $1.0 \times 10^7$ CFU/mL | Not observed |
| Cryptococcus neoformans | ATCC 208821 | $1.0 \times 10^7$ CFU/mL | Not observed |
| Fusarium verticillioides | ATCC 100312 | $1.0 \times 10^7$ CFU/mL | Not observed |
| Malassezia furfur | CBS 7710 | $1.0 \times 10^7$ CFU/mL | Not observed |
| Rhodotorula mucilaginosa | ATCC 4058 | $1.0 \times 10^7$ CFU/mL | Not observed |
| Trichosporon dermatis | ATCC 204094 | $1.0 \times 10^7$ CFU/mL | Not observed |

TABLE 39

Cross-reactivity with Organisms Not Detected by the BCID-FP Panel (Exclusivity)

| Organism | Classification | Strain | Highest Concentration Tested | Cross-Reactivity Results |
|---|---|---|---|---|
| Aspergillus fumigatus | Fungus | ATCC 204305 | $2.6 \times 10^6$ CFU/mL | Not observed |
| Candida bracarensis | Fungus | CBS 10154 | $1.0 \times 10^7$ CFU/mL | Not observed |
| Candida metapsilosis | Fungus | ATCC 96144 | $1.0 \times 10^7$ CFU/mL | Not observed |
| Candida orthopsilosis | Fungus | ATCC 96139 | $1.0 \times 10^7$ CFU/mL | Not observed |
| Candida rugosa | Fungus | CBS 96275 | $1.0 \times 10^7$ CFU/mL | Not observed |
| Filobasidium elegans | Fungus | CBS 7637 | $1.0 \times 10^7$ CFU/mL | Not observed |
| Filobasidium globisporum | Fungus | CBS 7642 | $1.0 \times 10^7$ CFU/mL | Not observed |
| Kluyveromyces lactis | Fungus | ATCC 10689 | $1.0 \times 10^7$ CFU/mL | Not observed |
| Malassezia globosa | Fungus | ATCC MYA-4612 | $1.0 \times 10^7$ CFU/mL | Not observed |
| Malassezia restricta | Fungus | ATCC MYA-4611 | $1.0 \times 10^7$ CFU/mL | Not observed |
| Malassezia sympodialis | Fungus | ATCC 44031 | $1.0 \times 10^7$ CFU/mL | Not observed |
| Saccharomyces cerevisiae | Fungus | ATCC 18824 | $1.0 \times 10^7$ CFU/mL | Not observed |
| Schizosaccharomyces pombe | Fungus | LPY 02387 | $4.9 \times 10^6$ CFU/mL | Not observed |
| Sporidiobolus salmonicolor | Fungus | ATCC 24217 | $1.0 \times 10^7$ CFU/mL | Not observed |
| Acinetobacter lwoffii | Gram-negative | ATCC 15309 | $1.0 \times 10^9$ CFU/mL | Not observed |
| Bacteroides fragilis | Gram-negative | ATCC 25285 | $1.0 \times 10^9$ CFU/mL | Not observed |
| Bordetella pertussis | Gram-negative | ATCC 9340 | $1.0 \times 10^9$ CFU/mL | Not observed |
| Citrobacter freundii | Gram-negative | ATCC 6879 | $1.0 \times 10^9$ CFU/mL | Not observed |
| Enterobacter aerogenes | Gram-negative | ATCC 29751 | $3.5 \times 10^8$ CFU/mL | Not observed |
| Enterobacter cloacae | Gram-negative | ATCC 23373 | $1.0 \times 10^9$ CFU/mL | Not observed |
| Klebsiella oxytoca | Gram-negative | ATCC 43165 | $1.0 \times 10^9$ CFU/mL | Not observed |
| Morganella morganii | Gram-negative | ATCC 25830 | $1.0 \times 10^9$ CFU/mL | Not observed |
| Proteus mirabilis | Gram-negative | ATCC 35659 | $1.0 \times 10^9$ CFU/mL | Not observed |
| Salmonella enterica Typhi | Gram-negative | ATCC 19430 | $1.0 \times 10^9$ CFU/mL | Not observed |
| Serratia marcescens | Gram-negative | ATCC 43861 | $1.0 \times 10^9$ CFU/mL | Not observed |
| Clostridium perfringens | Gram-positive | ATCC 13124 | $1.0 \times 10^9$ CFU/mL | Not observed |
| Corynebacterium striatum | Gram-positive | ATCC 7094 | $1.0 \times 10^9$ CFU/mL | Not observed |
| Enterococcus faecium | Gram-positive | ATCC 31282 | $1.0 \times 10^9$ CFU/mL | Not observed |
| Lactobacillus rhamnosus | Gram-positive | ATCC 53103 | $1.0 \times 10^9$ CFU/mL | Not observed |
| Micrococcus luteus | Gram-positive | ATCC 19212 | $1.0 \times 10^9$ CFU/mL | Not observed |
| Staphylococcus hominis (CoNS) | Gram-positive | ATCC 27844 | $1.0 \times 10^9$ CFU/mL | Not observed |
| Staphylococcus intermedius (CoPS) | Gram-positive | ATCC 29663 | $1.0 \times 10^9$ CFU/mL | Not observed |
| Staphylococcus saprophyticus (CoNS) | Gram-positive | ATCC 15305 | $1.0 \times 10^9$ CFU/mL | Not observed |
| Streptococcus agalactiae (Group B) | Gram-positive | ATCC 12401 | $1.0 \times 10^9$ CFU/mL | Not observed |
| Streptococcus anginosus (Group F) | Gram-positive | ATCC 9895 | $1.0 \times 10^9$ CFU/mL | Not observed |
| Streptococcus pyogenes (Group A) | Gram-positive | ATCC 12384 | $1.0 \times 10^9$ CFU/mL | Not observed |

Example 20, Fungal Panel, Competitive Inhibition

Detection of more than one clinically relevant fungal organism in a sample was evaluated with the BCID-FP Panel using sample matrix spiked with *Candida albicans* paired with *Candida glabrata* or *Candida parapsilosis*. *Candida albicans* was tested at $1 \times 10^7$ CFU/mL in conjunction with the other two *Candida* species at 10×LoD, and both *Candida glabrata* and *Candida parapsilosis* were tested at $1 \times 10^7$ CFU/mL in combination with *Candida albicans* at 10×LoD. Additionally, *Candida albicans* was tested at 10×LoD in combination with nine off-panel bacteria each at $>1 \times 10^9$ CFU/mL. If *Candida albicans* was not detected in triplicate at 10×LoD in the presence of any off-panel bacteria, testing was repeated at 30×LoD. These results, summarized in Table 40, demonstrate the ability of the BCID-FP Panel to detect two organisms in a sample at both high and low concentrations as well as the ability to detect low concentrations of clinically relevant fungi in the presence of a high concentration of off-panel organism.

TABLE 40

Detection of Co-Infections

| Organism 1 | Organism 1 Concentration | Organism 2 | Organism 2 Concentration | Results Organism 1/Organism 2 |
|---|---|---|---|---|
| Candida albicans[1] | 10× LoD | Candida glabrata[1] | $1.0 \times 10^7$ CFU/mL | Positive/Positive |
| Candida albicans[1] | 10× LOD | Candida parapsilosis[1] | $1.0 \times 10^7$ CFU/mL | Positive/Positive |
| Candida glabrata[1] | 10× LOD | Candida albicans[1] | $1.0 \times 10^7$ CFU/mL | Positive/Positive |
| Candida parapsilosis[1] | 10× LOD | Candida albicans[1] | $1.0 \times 10^7$ CFU/mL | Positive/Positive |
| Candida albicans[1] | 30× LoD | Acinetobacter baumannii | $1.0 \times 10^9$ CFU/mL | Positive/N/A |

TABLE 40-continued

Detection of Co-Infections

| Organism 1 | Organism 1 Concentration | Organism 2 | Organism 2 Concentration | Results Organism 1/ Organism 2 |
|---|---|---|---|---|
| *Candida albicans*[1] | 10× LoD | *Enterococcus faecalis* | 1.0 × 10$^9$ CFU/mL | Positive/N/A |
| *Candida albicans*[1] | 10× LoD | *Escherichia coli* | 1.0 × 10$^9$ CFU/mL | Positive/N/A |
| *Candida albicans*[1] | 10× LoD | *Klebsiella pneumoniae* | 1.0 × 10$^9$ CFU/mL | Positive/N/A |
| *Candida albicans*[1] | 10× LoD | *Pseudomonas aeruginosa* | 1.0 × 10$^9$ CFU/mL | Positive/N/A |
| *Candida albicans*[1] | 10× LoD | *Staphylococcus aureus* | 1.0 × 10$^9$ CFU/mL | Positive/N/A |
| *Candida albicans*[1] | 10× LoD | *Staphylococcus epidermidis* | 1.0 × 10$^9$ CFU/mL | Positive/N/A |
| *Candida albicans*[1] | 10× LoD | *Streptococcus pneumoniae* | 1.0 × 10$^9$ CFU/mL | Positive/N/A |
| *Candida albicans*[1] | 10× LoD | *Propionibacterium acnes* | 1.0 × 10$^9$ CFU/mL | Positive/N/A |

[1]On-panel organism

Example 21, Fungal Panel, Interfering Substances

Substances

Fifteen substances commonly found in blood culture specimens or as medications commonly used to treat the skin or bloodstream infections which could potentially interfere with the BCID-FP Panel were individually evaluated. Each potentially interfering substance was spiked into negative sample matrix at a medically relevant concentration. Five organisms representing a broad range of fungal pathogens were combined to achieve a final concentration of 10× each and run in triplicate. The organisms on the test panel and the interfering substances are summarized in Tables 42 and 43, respectively.

Blood Culture Bottles

The potential inhibitory effect of various blood culture bottle types were evaluated as part of the interfering substance study. A diverse sub-panel containing 5 fungi, including the most prevalent fungal organisms identified in positive blood culture, was spiked into sample matrix at a concentration of 10×LoD each, in fifteen types of blood culture bottles. Two replicates were tested per bottle type. One replicate of each bottle type was inoculated with negative blood only as a negative control. The study is summarized in Table 41.

All substances and organisms tested for interference were shown to be compatible with the BCID-FP Panel. No potentially interfering substances or bottle types were found to inhibit the BCID-FP Panel at the concentrations tested.

TABLE 41

Potentially Interfering Substances: Fungal Organism List

| Assay Evaluated | Organism | Strain | Concentration |
|---|---|---|---|
| *Candida kefyr* | *Candida kefyr* | ATCC 4135 | 10× LoD |
| *Cryptococcus neoformans* | *Cryptococcus neoformans grubii* | ATCC 208821 | 10× LoD |
| *Fusarium* | *Fusarium verticillioides* | CBS 100312 | 10× LoD |
| *Rhodotorula* | *Rhodotorula mucilaginosa* | ATCC 4058 | 10× LoD |
| *Candida albicans* | *Candida albicans* | ATCC 14053 | 10× LoD |

TABLE 42

Potentially Interfering Substances: Substance List

| | Testing Concentration |
|---|---|
| Endogenous Substances | |
| Bilirubin | 20 mg/dL |
| Hemoglobin | 14 g/L |
| Human Genomic DNA | 6.0 × 10$^4$ copies/mL |
| Triglycerides | 3000 mg/dL |
| γ-globulin | 5.4 g/dL |
| Exogenous Substances | |
| Heparin | 0.4 U/mL |
| Amoxicillin/Clavulanate | 7.5 ug/mL |
| Amphotericin B | 2.0 mg/L |
| Ceftriaxone | 0.152 mg/mL |
| Ciprofloxacin | 7.27 mg/L |
| Fluconazole | 15.6 mg/L |
| Gentamicin sulfate | 0.01 mg/mL |
| Imipenem | 0.083 mg/mL |
| Tetracycline | 5 mg/L |
| Vancomycin | 15 mg/L |

TABLE 43

Potentially Interfering Substances: Bottle Types

| Bottle Brand | Bottle Type |
|---|---|
| BACTEC | Plus Aerobic/F |
| BACTEC | Standard/10 Aerobic/F |
| BACTEC | Standard Anaerobic/F |
| BACTEC | Plus Anaerobic/F |
| BACTEC | Pediatric Plus |
| BACTEC | Lytic/10 Anaerobic/F |
| BACTEC | MYCO/F Lytic |
| BacT/ALERT | SA Standard Aerobic |
| BacT/ALERT | SN Standard Anaerobic |
| BacT/ALERT | FA Aerobic FAN |

TABLE 43-continued

Potentially Interfering Substances: Bottle Types

| Bottle Brand | Bottle Type |
|---|---|
| BacT/ALERT | FN Anaerobic FAN |
| BacT/ALERT | PF Pediatric FAN |
| BacT/ALERT | MP Mycobacteria for yeast/fungi |
| VersaTREK | REDOX 1 EZ Draw Aerobic |
| VersaTREK | REDOX 2 EZ Draw Anaerobic |

What is claimed is:

1. An in vitro method for detecting a viable gram-positive microorganism comprising:
   a) subjecting a sample in blood culture medium, i) the sample comprising or suspected of comprising, the viable pram-positive microorganism and ii) the blood culture medium comprising nucleic acid from a non-viable gram-positive microorganism, wherein the non-viable cram-positive microorganism is the same pram-positive microorganism as the viable gram-positive microorganism, and is present in the sample at a lower concentration than the viable gram-positive microorganism, to a single detuned multiplex end-point polymerase chain reaction (PCR) to produce amplicons, the PCR comprising about 30 to about 35 cycles;
   b) contacting amplicons from step a with a plurality of signal probes and a plurality of capture probes, one of the signal probes and one of the capture probes is specific for the amplicons to form a hybridization complex; and
   c) electrochemically detecting an amount of hybridization complex above a threshold thereby detecting the viable gram-positive microorganism, and not detecting the nucleic acid from the non-viable gram-positive microorganism present in the blood culture medium.

2. The method of claim 1, further comprising, prior to step a, contacting the sample with a compound which hydrolyzes nucleic acids and extracting the nucleic acids.

3. The method of claim 1, wherein if four or more microorganisms are detected by the method, the method is repeated.

4. The method of claim 1, further comprising generating an epidemiology report on a clinical instrument.

5. The method of claim 1, further comprising reporting the detected viable gram-positive microorganism to a hospital's laboratory information system (LIS).

6. The method of claim 1, wherein the viable gram-positive microorganism is a *Bacillus cereus*, a *Micrococcus*, a *Bacillus subtilis*, a *Staphylococcus*, a *Staphylococcus aureus*, a *Propionibacterium acnes*, a *Staphylococcus epidermidis*, a *Staphylococcus lugdunensis*, a *Enterococcus faecalis*, a *Streptococcus*, a *Enterococcus faecium*, a *Streptococcus agalactiae*, a *Lactobacillus*, a *Listeria*, a *Streptococcus pneumoniae*, a *Listeria monocytogenes*, or a *Streptococcus pyogenes*.

7. The method of claim 1, wherein the viable gram-positive microorganism is a *S. anginosus*, a *Enterococcus* spp., or a *Corynebacterium* and the single detuned multiplex end-point PCR comprises primers at a primer concentration of about 250 nM.

8. The method of claim 1, wherein the single multiplex PCR comprises shuttling, by electrowetting manipulation, the sample across thermal zones comprising a denature heater and an anneal/extension heater.

9. The method of claim 1, wherein a *Streptococcus* spp., a *P. acnes* and a *Streptococcus pneumoniae* gram-positive microorganism are amplified together in a multiplex pool.

10. The method of claim 1, further comprising detecting a viable gram-negative microorganism, fungal microorganism or antimicrobial resistance gene.

11. The method of claim 1, wherein false positives from the non-viable microorganism is less than 5%.

12. The method of claim 1, wherein the method has a limit of detection of $1\times10^5$ CFU/mL, $1\times10^4$ CFU/mL, or $1\times10^6$ CFU/mL.

13. An in vitro method for detecting a viable gram-negative microorganism comprising:
   a) subjecting a sample in blood culture medium, i) the sample comprising or suspected of comprising, the viable gram-negative microorganism and ii) the blood culture medium comprising nucleic acid from a non-viable gram-negative microorganism, the non-viable gram-negative microorganism is the same gram-negative microorganism as the viable gram-negative microorganism, and is present in the sample at a lower concentration than the viable gram-negative microorganism, to a single detuned multiplex end-point polymerase chain reaction (PCR) comprising about 30 cycles to produce amplicons;
   b) contacting amplicons from step a with a plurality of signal probes and a plurality of capture probes, one of the signal probes and one of the capture probes is specific for the amplicons to form a hybridization complex; and
   c) electrochemically detecting an amount of hybridization complex above a threshold thereby detecting the viable gram-negative microorganism, and not detecting the nucleic acid from the non-viable gram-negative microorganism present in the blood culture medium.

14. The method of claim 13, wherein the viable gram-negative microorganism is a *Acinetobacter baumannii*, a *Klebsiella pneumoniae*, a *Bacteroides fragilis*, a *Morganella morganii*, a *Citrobacter*, a *Neisseria meningitides*, a *Cronobacter sakazakii*, a *Proteus*, a *Enterobacter cloacae* complex, a *Proteus mirabilis*, a *Enterobacter*, a *Pseudomonas aeruginosa*, a *Escherichia coli*, a *Salmonella*, a *Fusobacterium necrophorum*, a *Serratia*, a *Fusobacterium nucleatum*, a *Serratia marcescens*, a *Haemophilus* influenza, a *Stenotrophomonas maltophilia*, or a *Klebsiella oxytoca*.

15. The method of claim 13, further comprising detecting a viable gram-positive microorganism, fungal microorganism or antimicrobial resistance gene.

16. An in vitro method for detecting a viable fungal microorganism comprising:
   a) subjecting a sample in blood culture medium, i) the sample comprising or suspected of comprising, the viable fungal microorganism and ii) the blood culture medium comprising nucleic acid from a non-viable fungal microorganism, the non-viable fungal microorganism is the same fungal microorganism as the viable fungal microorganism, and is present in the sample at a lower concentration than the viable fungal microorganism, to a single detuned multiplex end-point polymerase chain reaction (PCR) to produce amplicons wherein the PCR comprises multiple pairs of primers and at least one pair of primers comprises mismatches compared to a gene of the viable fungal microorganism;
   b) contacting amplicons from step a with a plurality of signal probes and a plurality of capture probes, one of the signal probes and one of the capture probes is specific for the amplicons to form a hybridization complex; and
   c) electrochemically detecting an amount of hybridization complex above a threshold thereby detecting the viable fungal microorganism, and not detecting the nucleic acid from the non-viable fungal microorganism present in the blood culture medium.

17. The method of claim 16, wherein the viable fungal microorganism is a *Candida albicans*, a *Candida lusitaniae*, a *Candida auris*, a *Candida dubliniensis*, a *Candida famata*, a *Cryptococcus gattii*, a *Candida glabrata*, a *Cryptococcus neoformans*, a *Candida guilliermondii*, a *Fusarium*, a *Candida kefyr*, a *Malassezia furfur*, or a *Candida krusei*.

18. The method of claim 16, wherein the hybridization complex comprising a *Candida parapsilosis* or a *Candida tropicalis* fungal microorganism is detected in two detection zones.

19. The method of claim 16, wherein the viable fungal microorganism is a *Rhodotorula* or a *Trichosporon* and the primers for the *Rhodotorula* or the *Trichosporon* viable fungal microorganism contain mismatches compared to a wildtype gene for *Rhodotorula* or *Trichosporon*.

20. The method of claim 16, wherein the single detuned multiplex end-point PCR comprises primers consisting of the nucleic acid sequence of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, or SEQ ID NO: 9.

* * * * *

UNITED STATES PATENT AND TRADEMARK OFFICE
CERTIFICATE OF CORRECTION

| | | |
|---|---|---|
| PATENT NO. | : 10,106,847 B1 | Page 1 of 1 |
| APPLICATION NO. | : 15/828074 | |
| DATED | : October 23, 2018 | |
| INVENTOR(S) | : Brown et al. | |

It is certified that error appears in the above-identified patent and that said Letters Patent is hereby corrected as shown below:

On the Title Page

<u>In the Abstract:</u>
Item (57), beginning at Line 7, "fungal infection as wells as identify antimicrobial resistance genes," should read --fungal infection as well as identify antimicrobial resistance genes.--

In the Claims

Column 103, beginning at Line 45, Claim 1, "viable pram-positive microorganism and ii) the blood" should read --the viable gram-positive microorganism and ii) the blood--

Column 103, beginning at Line 48, Claim 1, "viable cram-positive microorganism is the same pram-positive microorganism," should read --viable gram-positive microorganism is the same gram-positive microorganism.--

Signed and Sealed this
Nineteenth Day of February, 2019

Andrei Iancu
*Director of the United States Patent and Trademark Office*

```
                         SEQUENCE LISTING

<160> NUMBER OF SEQ ID NOS: 9

<210> SEQ ID NO 1
<211> LENGTH: 25
<212> TYPE: DNA
<213> ORGANISM: Rhodotorula
<220> FEATURE:
<221> NAME/KEY: misc_feature
<222> LOCATION: (1)..(1)
<223> OTHER INFORMATION: n is a, c, g, or t

<400> SEQUENCE: 1
nactagcact acacgagcac ggaag                                            25

<210> SEQ ID NO 2
<211> LENGTH: 25
<212> TYPE: DNA
<213> ORGANISM: rhodotorula
<220> FEATURE:
<221> NAME/KEY: misc_feature
<222> LOCATION: (1)..(1)
<223> OTHER INFORMATION: n is a, c, g, or t

<400> SEQUENCE: 2
nagcacggaa gtagtaaccc attag                                            25

<210> SEQ ID NO 3
<211> LENGTH: 26
<212> TYPE: DNA
<213> ORGANISM: trichosporon

<400> SEQUENCE: 3
actctacacc gattcttcta acttca                                           26

<210> SEQ ID NO 4
<211> LENGTH: 26
<212> TYPE: DNA
<213> ORGANISM: trichosporon

<400> SEQUENCE: 4
acacttcacc gattcttcta acttca                                           26

<210> SEQ ID NO 5
<211> LENGTH: 24
<212> TYPE: DNA
<213> ORGANISM: rhodotorula

<400> SEQUENCE: 5
ggtagttcgg agcgtggaat acca                                             24

<210> SEQ ID NO 6
<211> LENGTH: 24
<212> TYPE: DNA
<213> ORGANISM: rhodotorula

<400> SEQUENCE: 6
```

```
ggtcgtttgg tacgtagaat acca                                          24

<210> SEQ ID NO 7
<211> LENGTH: 27
<212> TYPE: DNA
<213> ORGANISM: trichosporon
<220> FEATURE:
<221> NAME/KEY: misc_feature
<222> LOCATION: (1)..(1)
<223> OTHER INFORMATION: n is a, c, g, or t

<400> SEQUENCE: 7
natgtaatat ggatgcattg gaactcg                                       27

<210> SEQ ID NO 8
<211> LENGTH: 27
<212> TYPE: DNA
<213> ORGANISM: trichosporon
<220> FEATURE:
<221> NAME/KEY: misc_feature
<222> LOCATION: (1)..(1)
<223> OTHER INFORMATION: n is a, c, g, or t

<400> SEQUENCE: 8
natgtaatat ggatgcattg gcactcg                                       27

<210> SEQ ID NO 9
<211> LENGTH: 27
<212> TYPE: DNA
<213> ORGANISM: trichosporon
<220> FEATURE:
<221> NAME/KEY: misc_feature
<222> LOCATION: (1)..(1)
<223> OTHER INFORMATION: n is a, c, g, or t

<400> SEQUENCE: 9
natataataa ggatgcattg gaattcg                                       27
```